US010918391B2

(12) United States Patent
Miller et al.

(10) Patent No.: US 10,918,391 B2
(45) Date of Patent: *Feb. 16, 2021

(54) METHOD AND APPARATUS FOR CLAMPING TISSUE AND OCCLUDING TUBULAR BODY LUMENS

(71) Applicant: Amsel Medical Corporation, Cambridge, MA (US)

(72) Inventors: Arnold Miller, Cambridge, MA (US); Nir Lilach, Kfar Yehoshua (IL)

(73) Assignee: AMSEL MEDICAL CORPORATION, Cambridge, MA (US)

( * ) Notice: Subject to any disclaimer, the term of this patent is extended or adjusted under 35 U.S.C. 154(b) by 162 days.

This patent is subject to a terminal disclaimer.

(21) Appl. No.: 16/049,422

(22) Filed: Jul. 30, 2018

(65) Prior Publication Data

US 2019/0083098 A1  Mar. 21, 2019

Related U.S. Application Data

(63) Continuation-in-part of application No. 14/272,304, filed on May 7, 2014, now Pat. No. 10,076,339, (Continued)

(51) Int. Cl.
*A61B 17/122* (2006.01)
*A61B 17/12* (2006.01)
(Continued)

(52) U.S. Cl.
CPC ...... *A61B 17/122* (2013.01); *A61B 17/00008* (2013.01); *A61B 17/0643* (2013.01);
(Continued)

(58) Field of Classification Search
CPC .............. A61B 17/0057; A61B 17/122; A61B 17/1227; A61B 17/064; A61B 17/0643; A61B 2017/00575; A61B 2017/00584; A61B 2017/00592; A61B 2017/00606; A61B 2017/00619; A61B 2017/00646; A61B 2017/0645; A61B 17/08; A61B 17/083; A61F 5/0086; A61F 6/206;
(Continued)

(56) References Cited

U.S. PATENT DOCUMENTS 3,971,284 A  7/1976  Hasson
4,007,743 A  2/1977  Blake
(Continued)

FOREIGN PATENT DOCUMENTS

EP  1745750     1/2007
EP  1908419 A1  4/2008
(Continued)

*Primary Examiner* — Melanie R Tyson

(57) ABSTRACT

A fastener or clamp for securing a tissue layer to another tissue or non-tissue layer has a proximal implant and a separate distal implant, connectible to each other, each implant having radially deployable legs that can engage the layers between the deployed legs, the legs being configured so that when the implants are connected, the legs of the proximal and distal implants are interdigitated in the absence of tissue.

27 Claims, 72 Drawing Sheets

Related U.S. Application Data which is a continuation-in-part of application No. 13/857,424, filed on Apr. 5, 2013, now abandoned, which is a continuation-in-part of application No. 13/348,416, filed on Jan. 11, 2012, now abandoned.

(60) Provisional application No. 61/820,589, filed on May 7, 2013, provisional application No. 61/620,787, filed on Apr. 5, 2012, provisional application No. 61/431,609, filed on Jan. 11, 2011.

(51) Int. Cl.
*A61B 17/064* (2006.01)
*A61B 17/128* (2006.01)
*A61B 17/00* (2006.01)
*A61B 17/08* (2006.01)

(52) U.S. Cl.
CPC ........ *A61B 17/12* (2013.01); *A61B 17/12009* (2013.01); *A61B 17/12013* (2013.01); *A61B 17/1214* (2013.01); *A61B 17/12022* (2013.01); *A61B 17/1227* (2013.01); *A61B 17/12031* (2013.01); *A61B 17/1285* (2013.01); *A61B 17/12109* (2013.01); *A61B 17/12145* (2013.01); *A61B 17/08* (2013.01); *A61B 17/12036* (2013.01); *A61B 2017/00862* (2013.01); *A61B 2017/00867* (2013.01); *A61B 2017/00986* (2013.01); *A61B 2017/12054* (2013.01)

(58) Field of Classification Search
CPC .. A61F 6/20; A61F 6/202; A61F 6/204; A61F 6/208; A61F 6/22; A61F 6/225
See application file for complete search history.

(56) References Cited

U.S. PATENT DOCUMENTS

| | | | |
|---|---|---|---|
| 4,235,238 A | 11/1980 | Ogiu |
| 4,326,531 A | 4/1982 | Shimonaka |
| 4,532,926 A | 8/1985 | O'Holla |
| 4,548,202 A | 10/1985 | Duncan |
| 4,573,469 A | 3/1986 | Golden |
| 4,800,879 A | 1/1989 | Golyakhovsky |
| 5,026,379 A | 6/1991 | Yoon |
| 5,217,484 A | 6/1993 | Marks |
| 5,282,811 A | 2/1994 | Booker |
| 5,290,299 A | 3/1994 | Fain |
| 5,334,217 A | 8/1994 | Das |
| 5,536,275 A | 7/1996 | Neuss |
| 5,601,557 A | 2/1997 | Hayhurst |
| 5,709,224 A | 1/1998 | Behl |
| 5,865,791 A | 2/1999 | Whayne |
| 5,947,994 A | 9/1999 | Louw |
| 5,976,127 A | 11/1999 | Lax |
| 6,071,292 A | 6/2000 | Makower |
| 6,113,611 A | 9/2000 | Miller |
| 6,132,438 A | 10/2000 | Fleischman |
| 6,156,044 A | 12/2000 | Kammerer |
| 6,312,446 B1 | 11/2001 | Huebsch |
| 6,319,278 B1 | 11/2001 | Quinn |
| 6,387,104 B1 | 5/2002 | Pugsley |
| 6,458,153 B1 | 10/2002 | Bailey |
| 6,485,504 B1 | 11/2002 | Johnson |
| 6,491,707 B2 | 12/2002 | Makowerr |
| 6,540,782 B1 | 4/2003 | Snyders |
| 6,551,533 B1 | 4/2003 | Kuhn |
| 6,565,581 B1 | 5/2003 | Spence |
| 6,616,684 B1 | 9/2003 | Vidland |
| 6,645,242 B1 | 11/2003 | Quinn |
| 6,776,754 B1 | 8/2004 | Wilk |
| 6,827,736 B2 | 12/2004 | Perouse |
| 6,951,571 B1 | 4/2005 | Snvastava |
| 6,913,607 B2 | 7/2005 | Ainsworth |
| 6,960,220 B2 | 11/2005 | Marino |
| 7,041,132 B2 | 5/2006 | Quijano |
| 7,101,366 B2 | 9/2006 | Trout |
| 7,149,587 B2 | 12/2006 | Wardle |
| 7,220,274 B1 | 5/2007 | Quinn |
| 7,416,554 B2 | 8/2008 | Lam |
| 7,462,183 B2 | 12/2008 | Behl |
| 7,766,816 B2 | 8/2010 | Chin |
| 7,766,962 B1 | 8/2010 | Quinn |
| 7,798,953 B1 | 9/2010 | Wilk |
| 7,942,884 B2 | 5/2011 | Vahid |
| 8,133,242 B1 | 3/2012 | Quinn |
| 8,211,121 B1 | 7/2012 | Quinn |
| 8,257,389 B2 | 9/2012 | Chanduszko |
| 8,556,961 B2 | 10/2013 | Quinn |
| 8,579,935 B2 | 11/2013 | DeVries |
| 8,632,520 B2 | 1/2014 | Otley |
| 8,870,946 B1 | 10/2014 | Quinn |
| 9,173,712 B2 | 11/2015 | Annest |
| 10,076,339 B2 * | 9/2018 | Miller .................... A61B 17/12 |
| 2003/0004568 A1 | 1/2003 | Ken |
| 2003/0105473 A1 | 6/2003 | Miller |
| 2003/0120286 A1 | 6/2003 | Burbank |
| 2003/0139819 A1 | 7/2003 | De Beer |
| 2003/0171771 A1 | 9/2003 | Anderson |
| 2003/0199963 A1 | 10/2003 | Tower |
| 2003/0199972 A1 | 10/2003 | Zadno-Azizi |
| 2004/0044364 A1 | 3/2004 | DeVries |
| 2004/0138684 A1 | 7/2004 | Elon |
| 2004/0215339 A1 | 10/2004 | Drasler |
| 2005/0004652 A1 | 1/2005 | Van Der Burg |
| 2005/0038460 A1 | 2/2005 | Jayaraman |
| 2005/0137682 A1 | 6/2005 | Justino |
| 2005/0267524 A1 | 12/2005 | Chanduszko |
| 2005/0267529 A1 | 12/2005 | Crockett |
| 2005/0277966 A1 | 12/2005 | Ewers |
| 2005/0288786 A1 | 12/2005 | Chanduszko |
| 2006/0264987 A1 | 11/2006 | Sgro |
| 2006/0271103 A1 | 11/2006 | Ferrari |
| 2007/0027466 A1 | 2/2007 | Ortiz |
| 2007/0043349 A1 | 2/2007 | Swanson |
| 2007/0073337 A1 | 3/2007 | Abbott |
| 2007/0106328 A1 | 5/2007 | Wardle |
| 2007/0135826 A1 | 6/2007 | Zaver |
| 2007/0144539 A1 | 6/2007 | Van der Burg |
| 2007/0179527 A1 | 8/2007 | Eskuri |
| 2007/0265658 A1 | 11/2007 | Nelson |
| 2008/0004640 A1 | 1/2008 | Ellingwood |
| 2008/0077180 A1 | 3/2008 | Kladakis |
| 2008/0109066 A1 | 5/2008 | Quinn |
| 2008/0208226 A1 | 8/2008 | Seibold |
| 2008/0306495 A1 | 12/2008 | Thompson |
| 2009/0084386 A1 | 4/2009 | McClellan |
| 2009/0114233 A1 | 5/2009 | Edoga |
| 2009/0157174 A1 | 6/2009 | Yoganathan |
| 2010/0004740 A1 | 1/2010 | Seguin |
| 2010/0198254 A1 | 8/2010 | Schaeffer |
| 2010/0228269 A1 | 9/2010 | Gamson |
| 2010/0234880 A1 | 9/2010 | Abbott |
| 2011/0082495 A1 | 4/2011 | Ruiz |
| 2011/0108039 A1 | 5/2011 | Frigstad |
| 2011/0152902 A1 | 6/2011 | Kurrus |
| 2011/0295302 A1 | 12/2011 | Mohl |
| 2011/0319906 A1 | 12/2011 | Rudakov |
| 2012/0232569 A1 | 9/2012 | Wright |
| 2012/0283758 A1 | 11/2012 | Miller |
| 2013/0046331 A1 | 2/2013 | Christensen |
| 2013/0218259 A1 | 8/2013 | Quinn |
| 2013/0274857 A1 | 10/2013 | Quinn |
| 2014/0100460 A1 | 4/2014 | Otley |
| 2015/0094740 A1 | 4/2015 | Gagne |
| 2015/0201947 A1 | 7/2015 | Hill |

FOREIGN PATENT DOCUMENTS

| | | |
|---|---|---|
| EP | 2311381 | 4/2011 |
| WO | WO 2005/006990 | 1/2005 |
| WO | WO 2006/130836 | 7/2006 |

(56) References Cited

FOREIGN PATENT DOCUMENTS

| WO | WO 2007/006286 | 1/2007 |
|---|---|---|
| WO | WO 2008/115922 | 9/2008 |
| WO | WO 2009/029914 | 3/2009 |
| WO | WO 2010/127083 | 11/2010 |

* cited by examiner

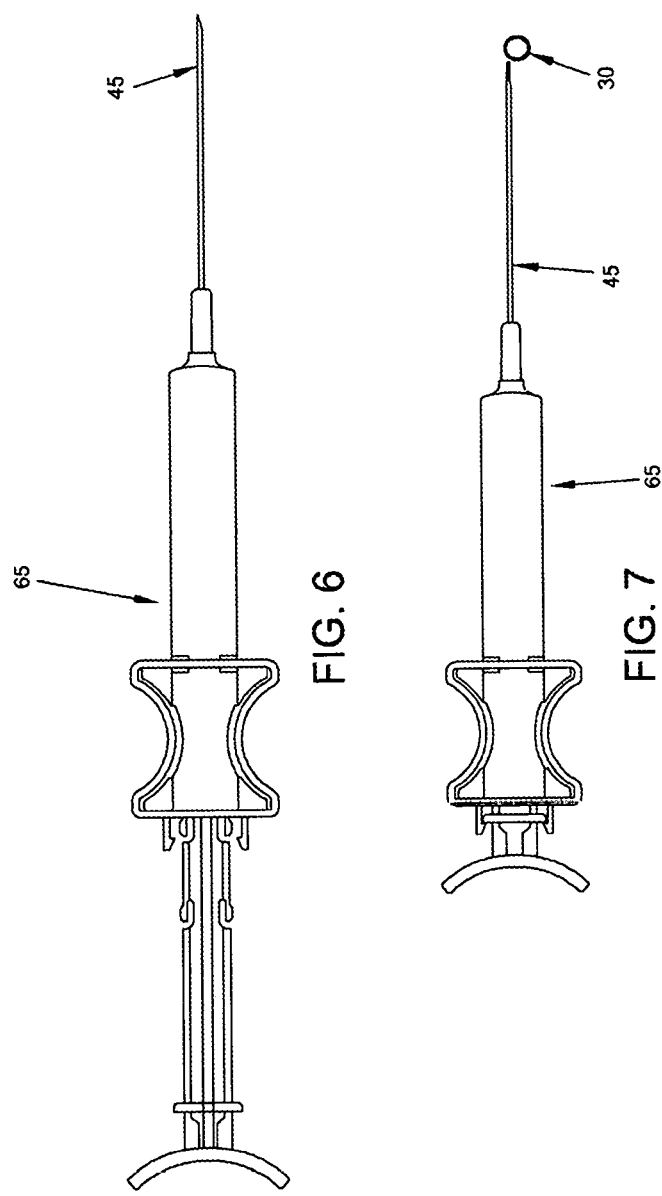

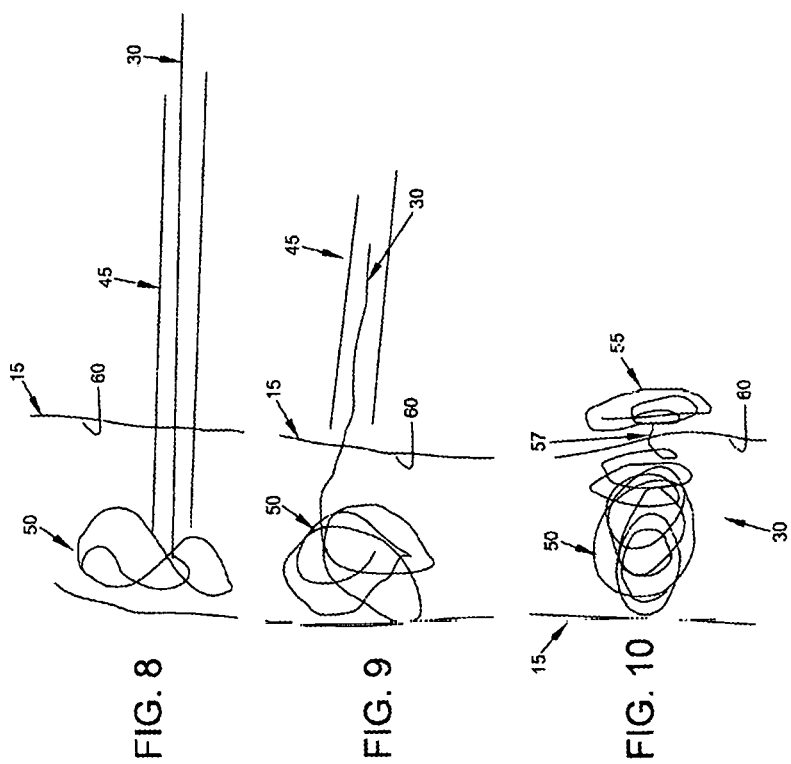

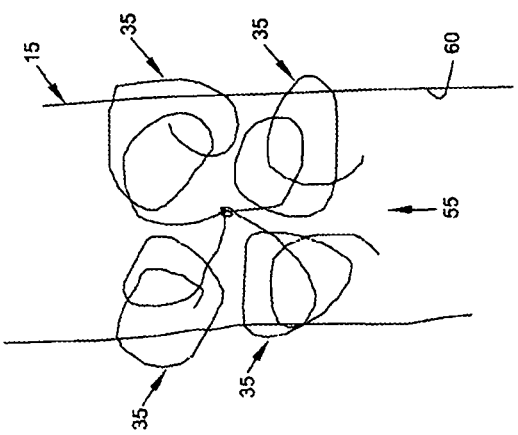
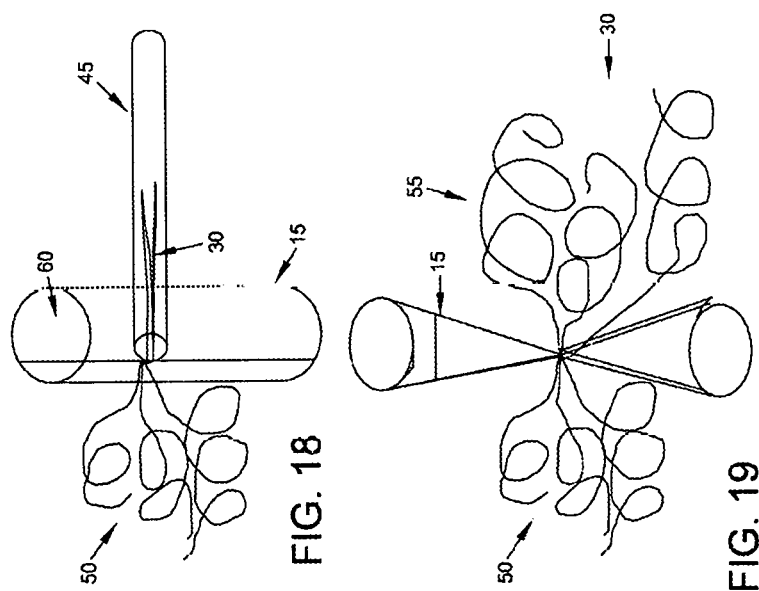

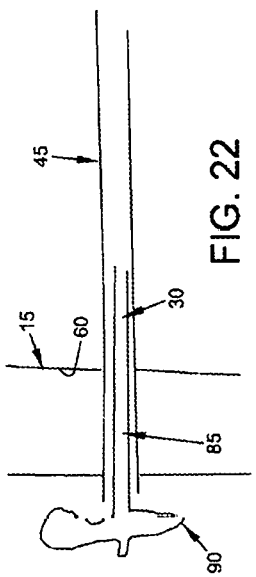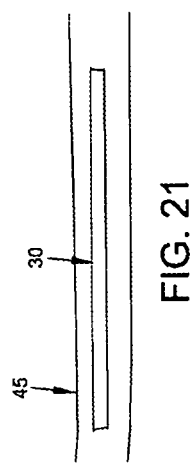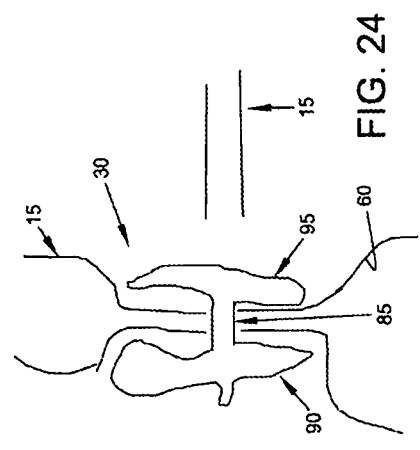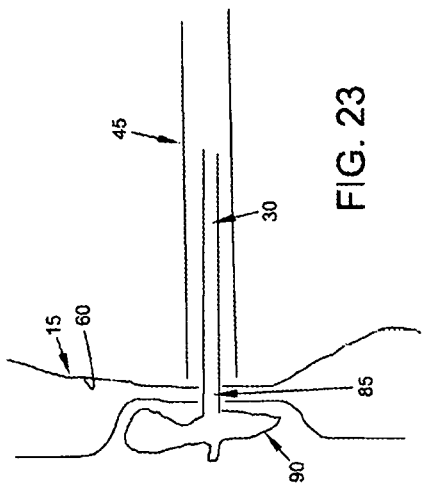

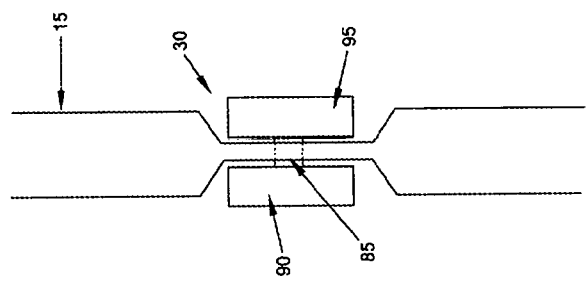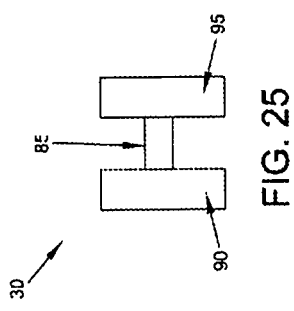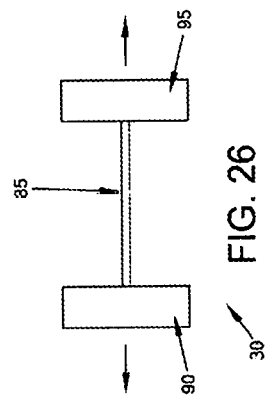

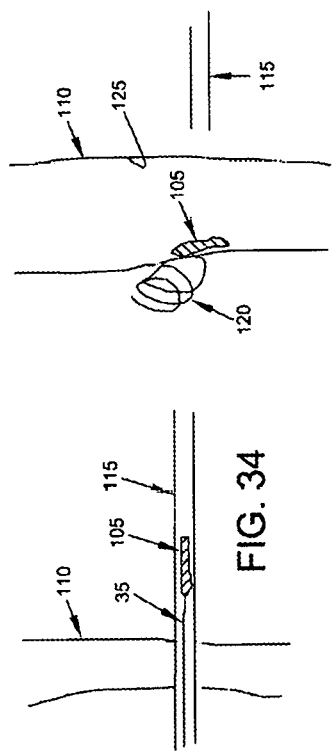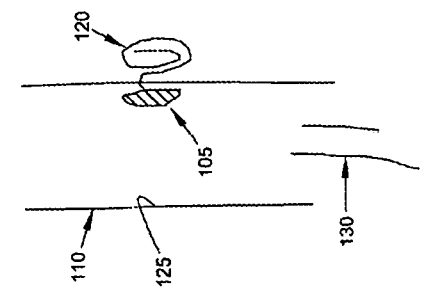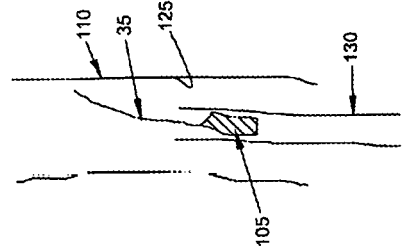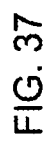

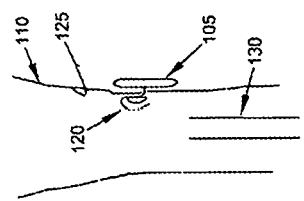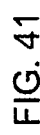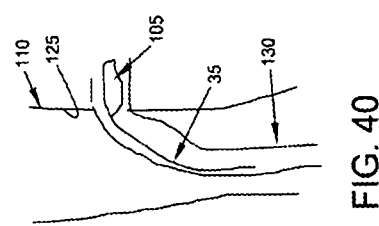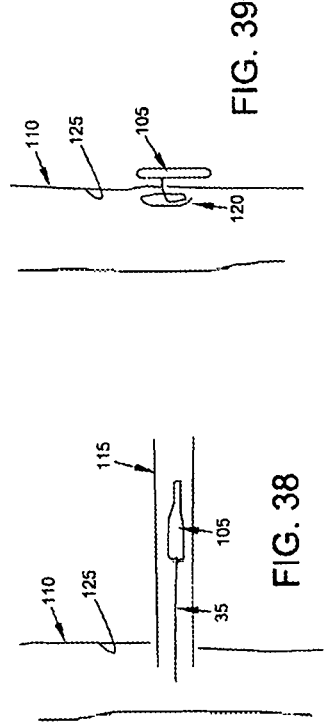

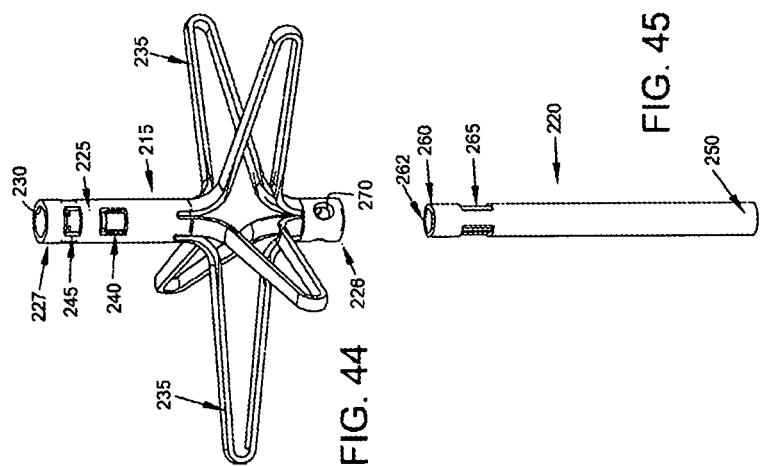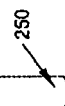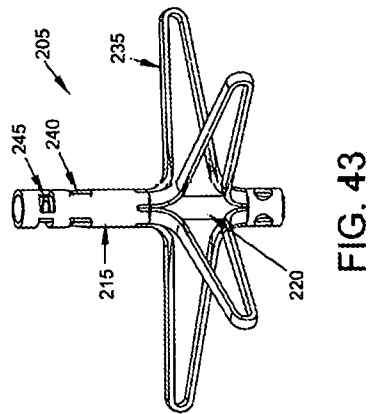

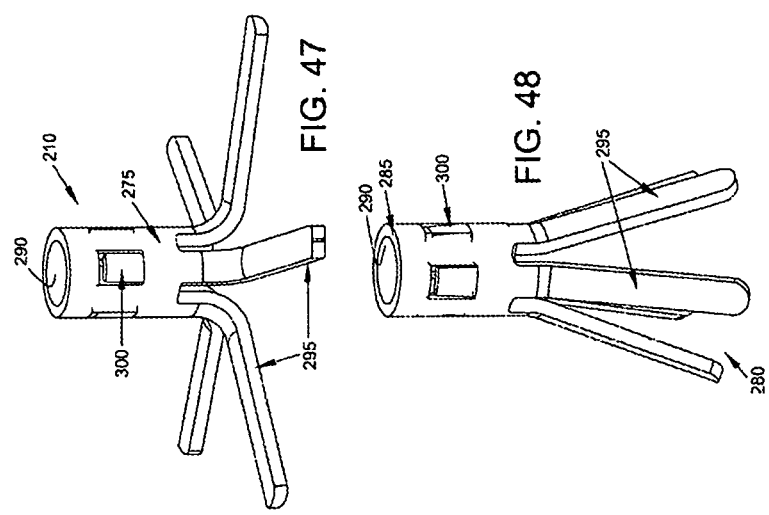
FIG. 47
FIG. 48
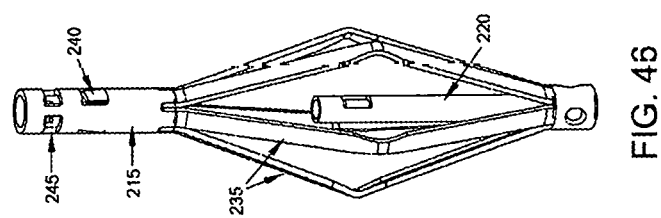
FIG. 46

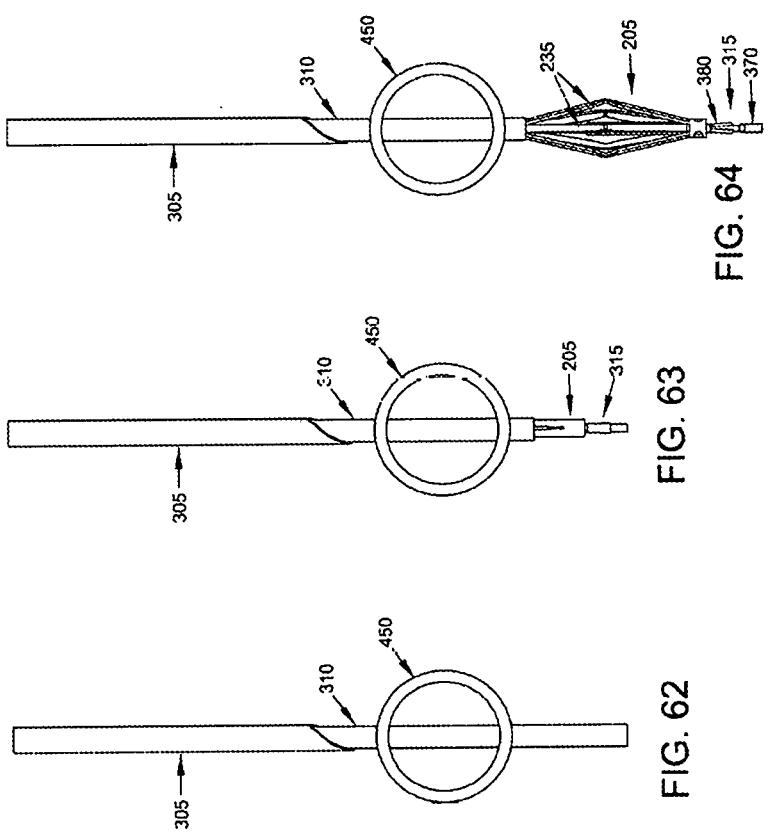

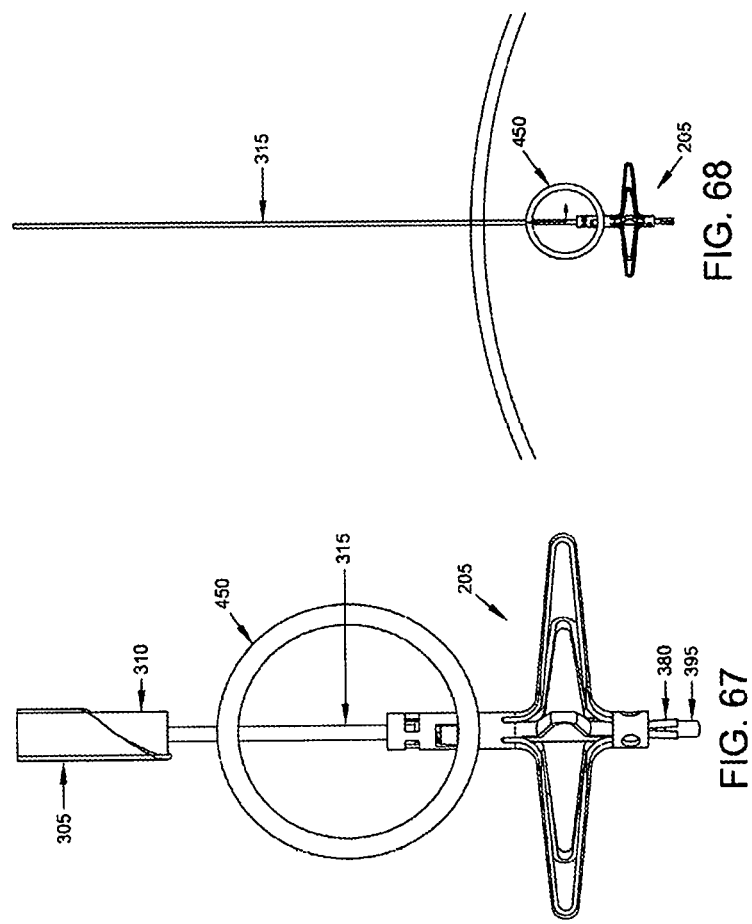

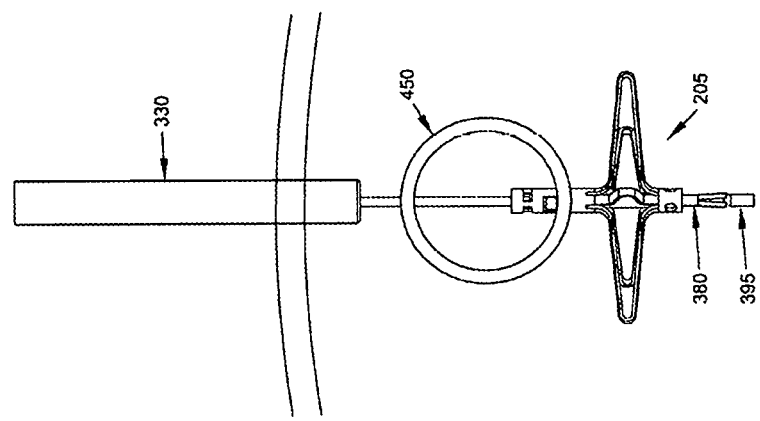
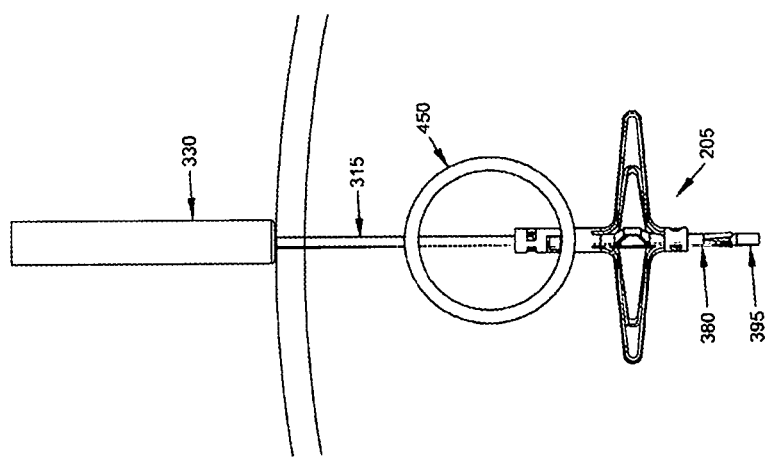

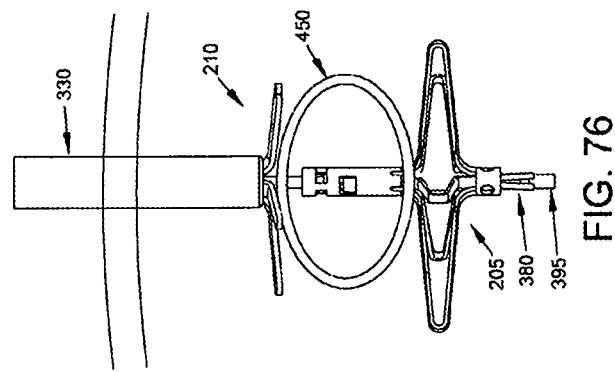
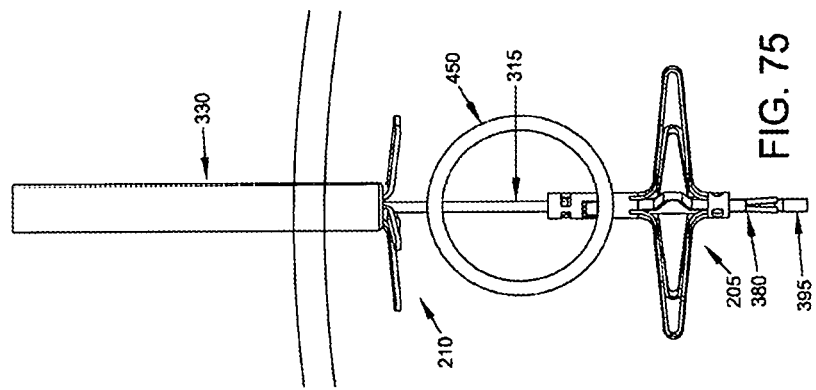

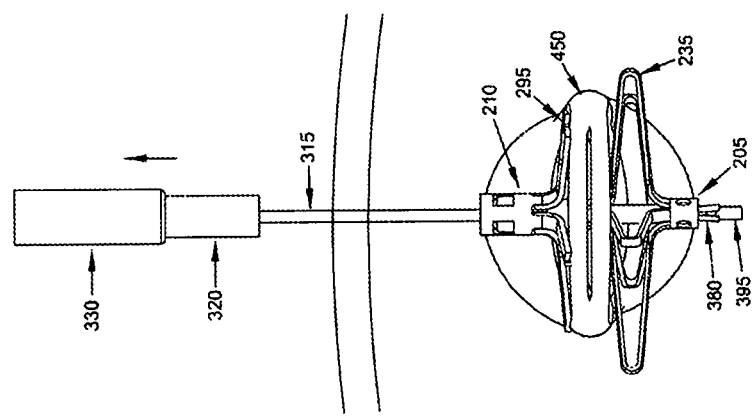
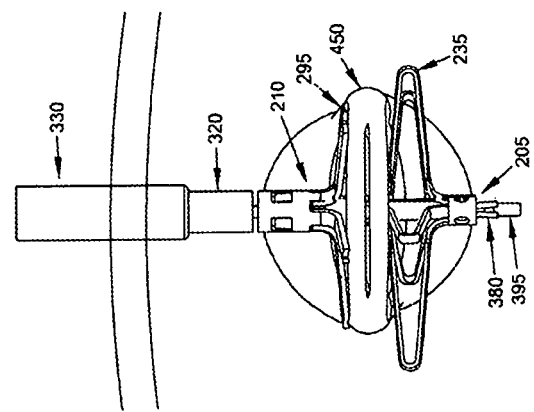

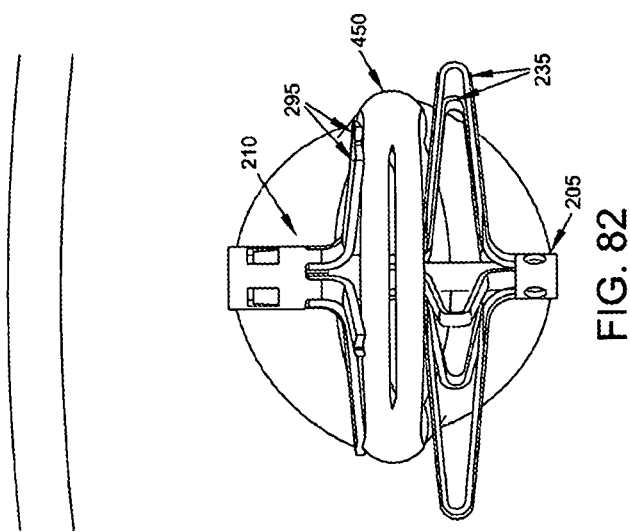
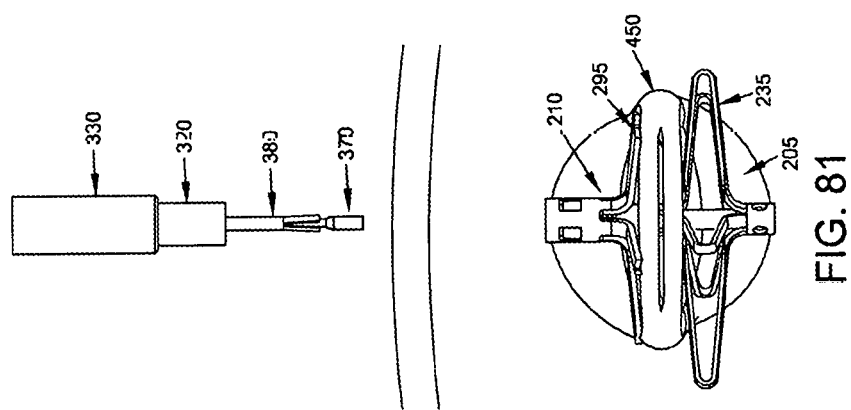

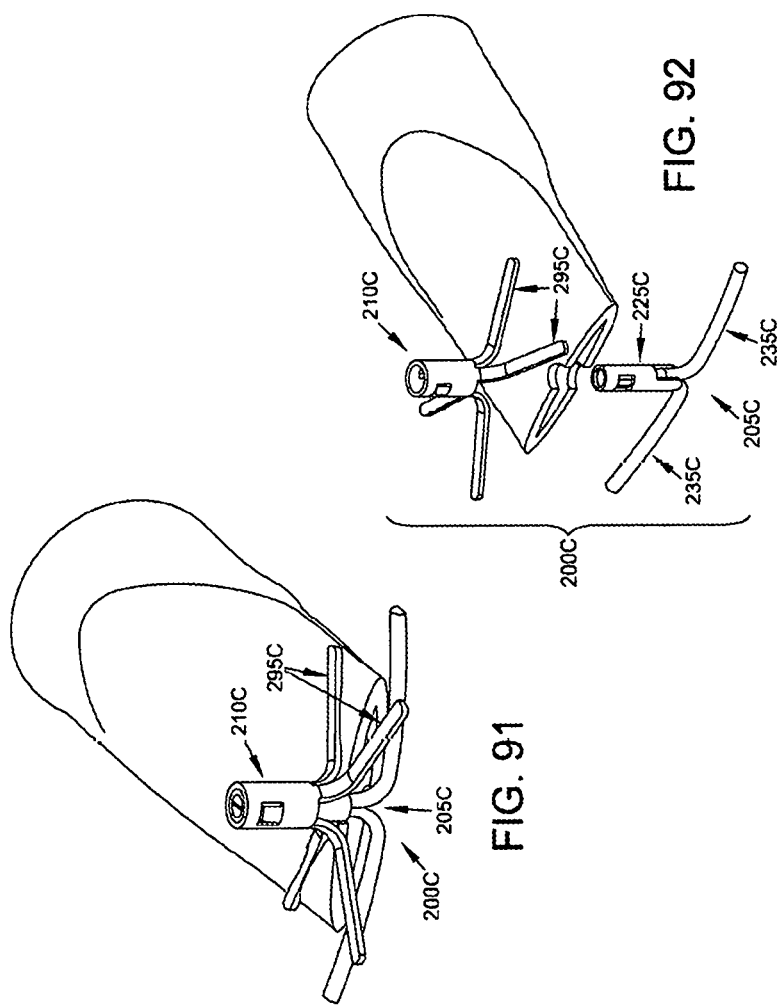

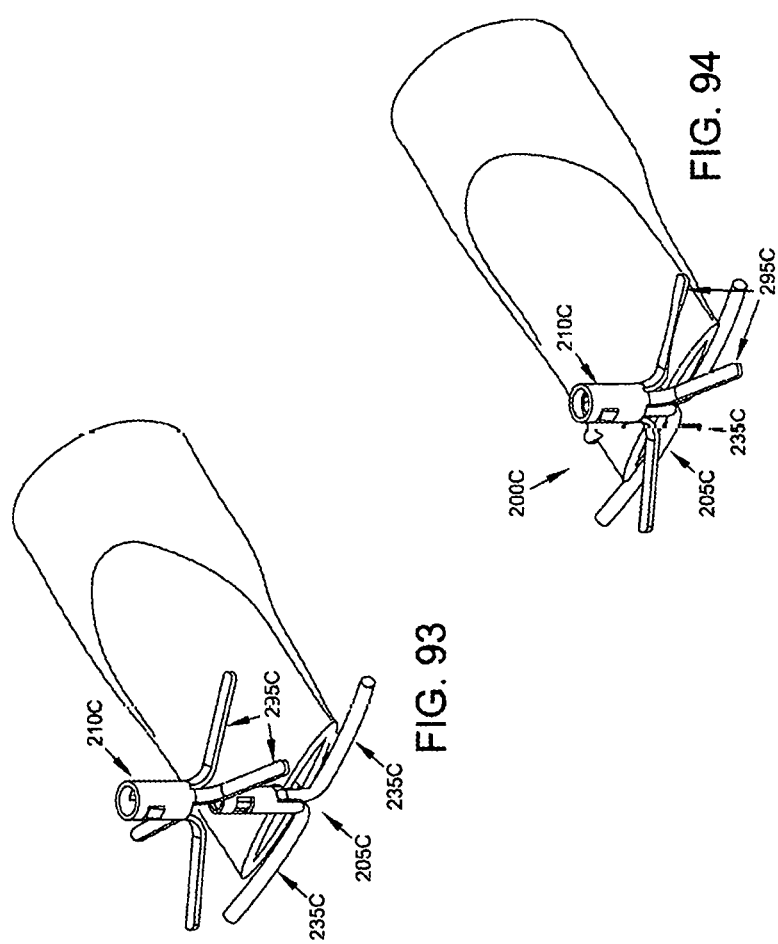

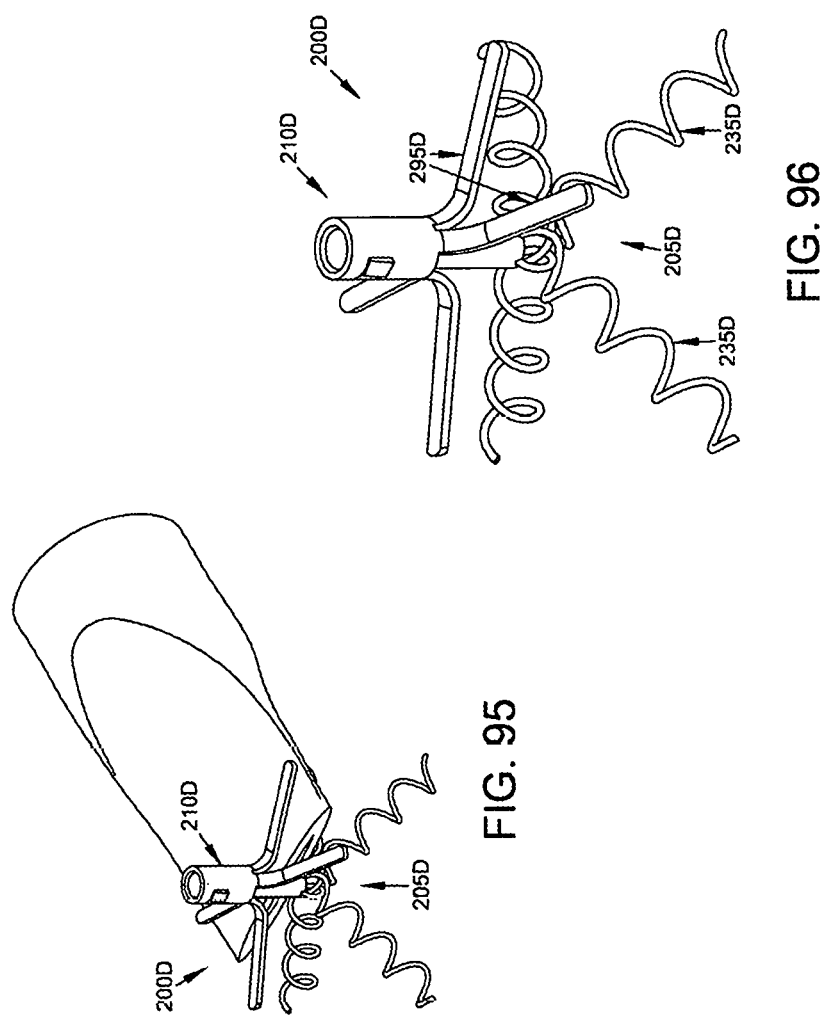

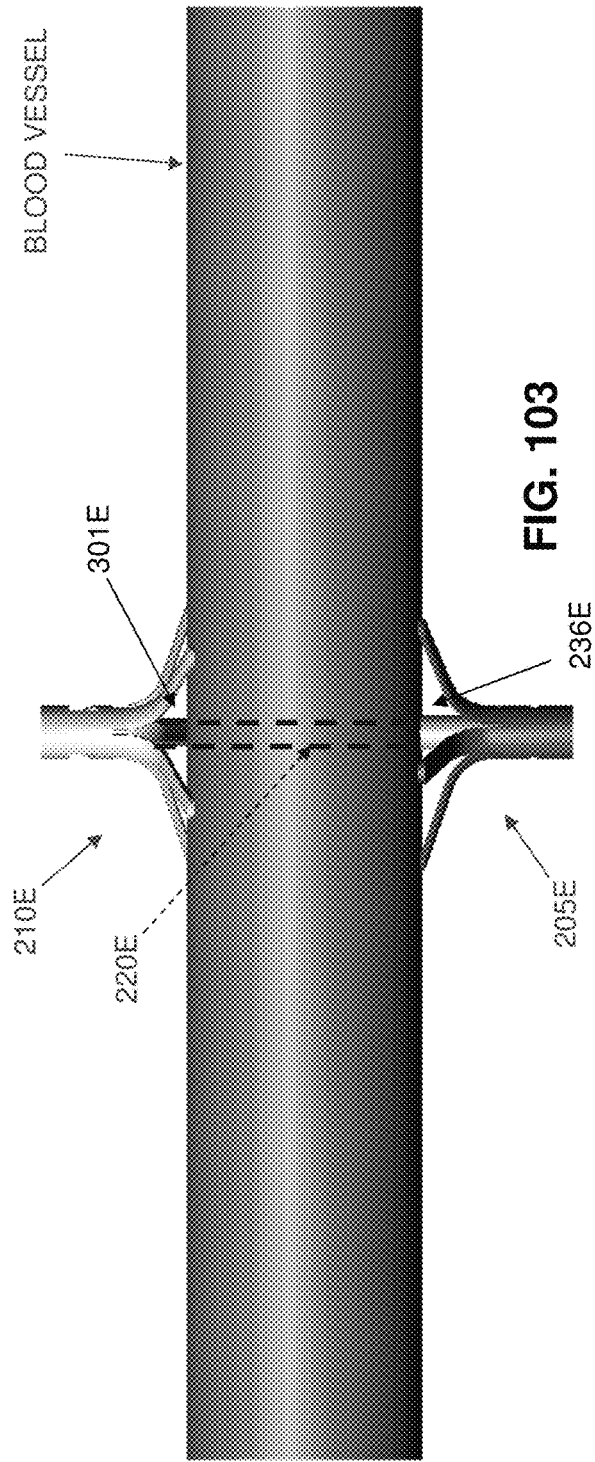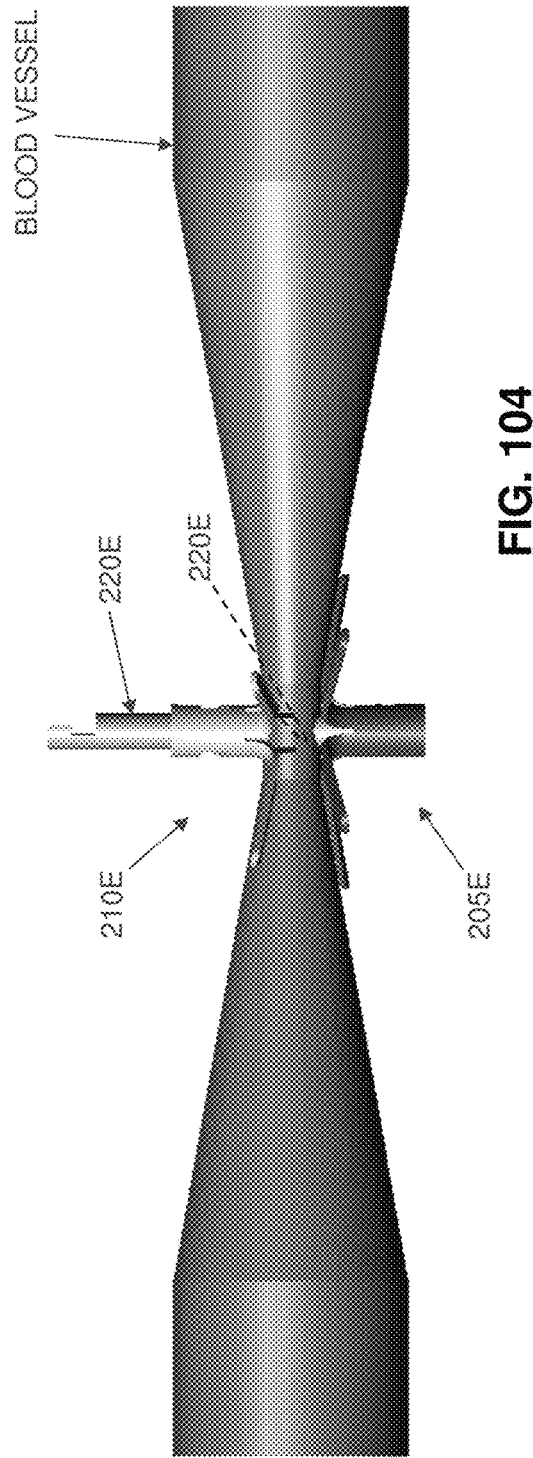

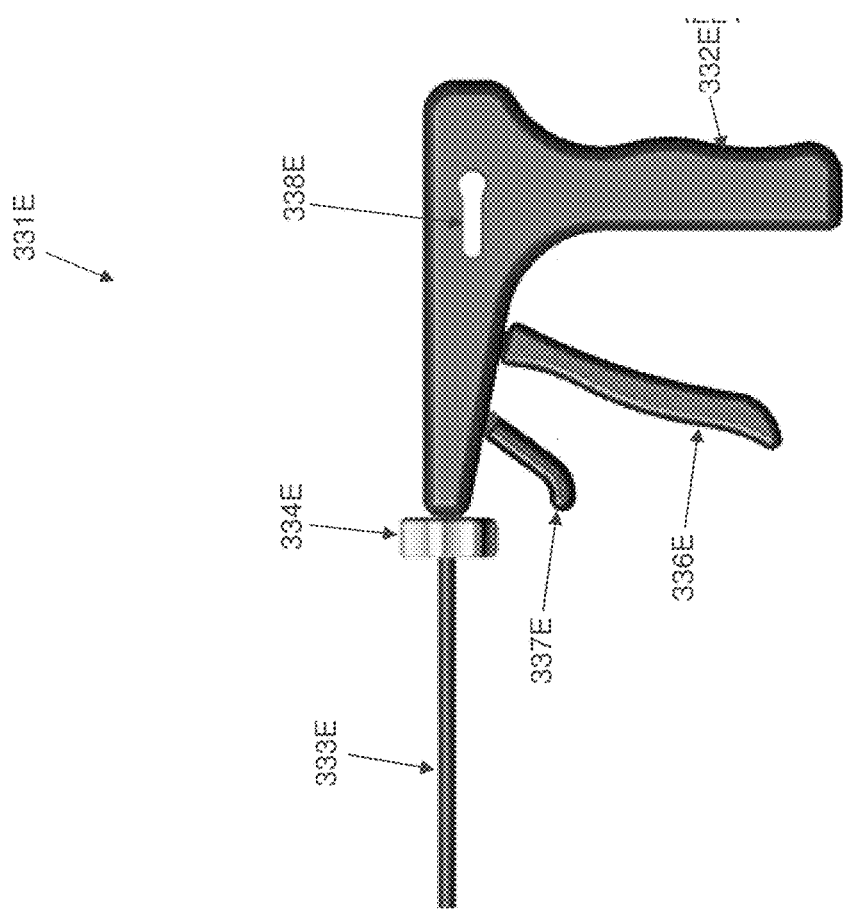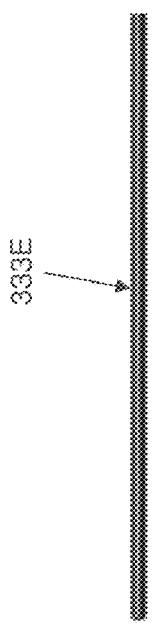
FIG. 107

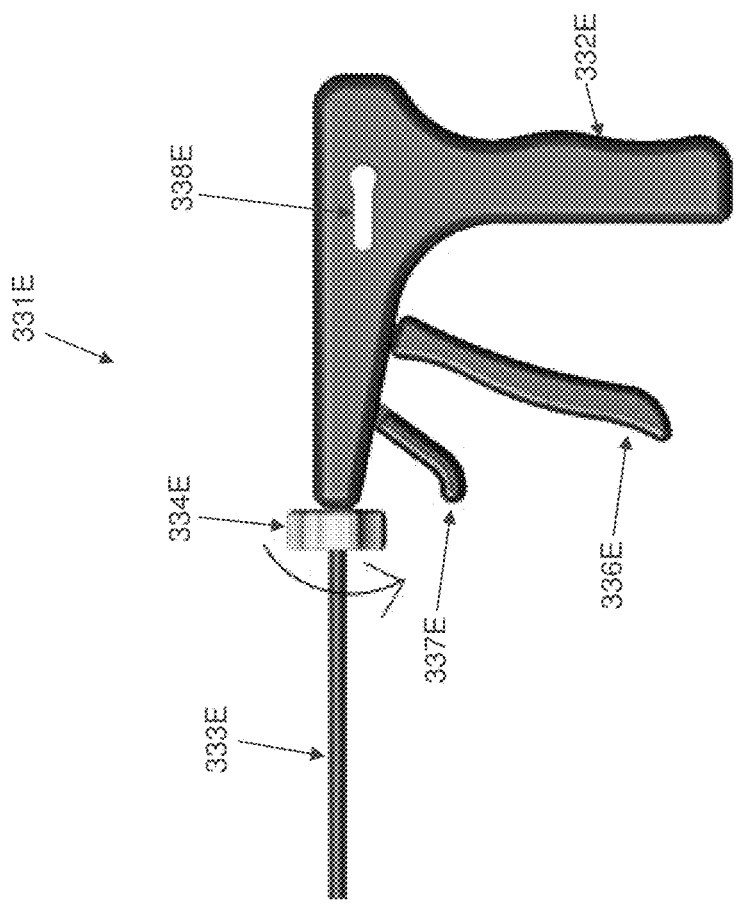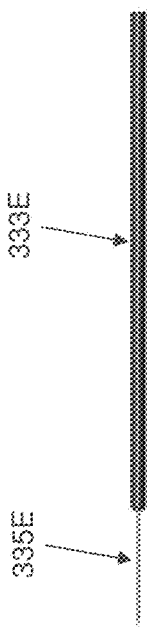
FIG. 108

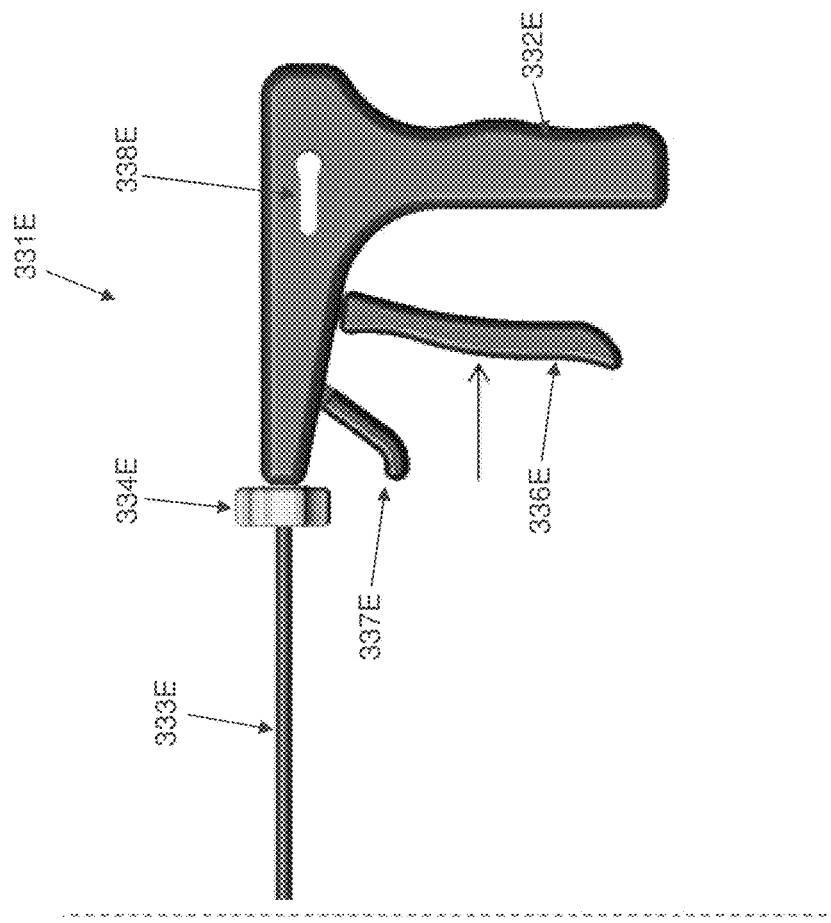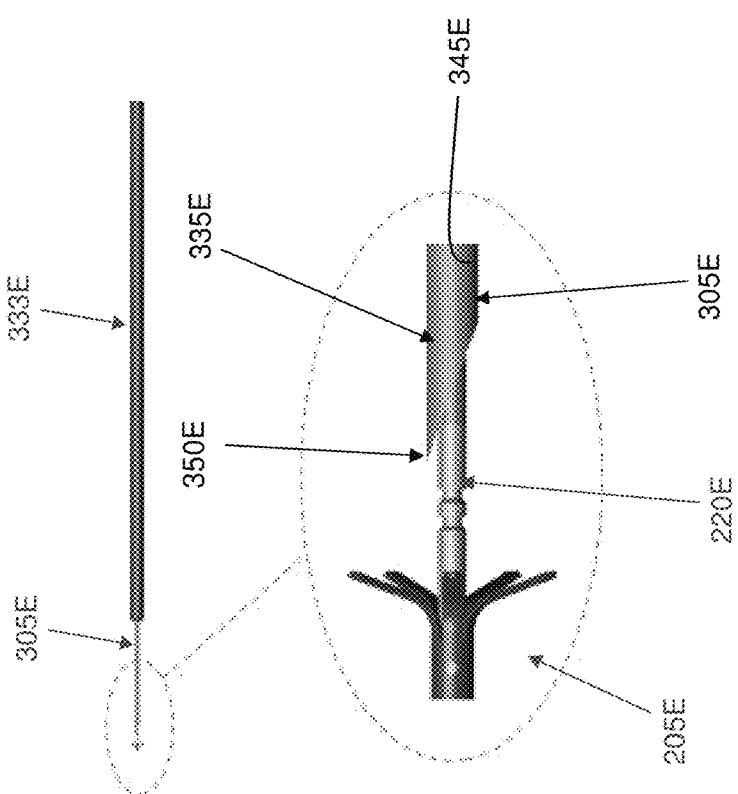
FIG. 109

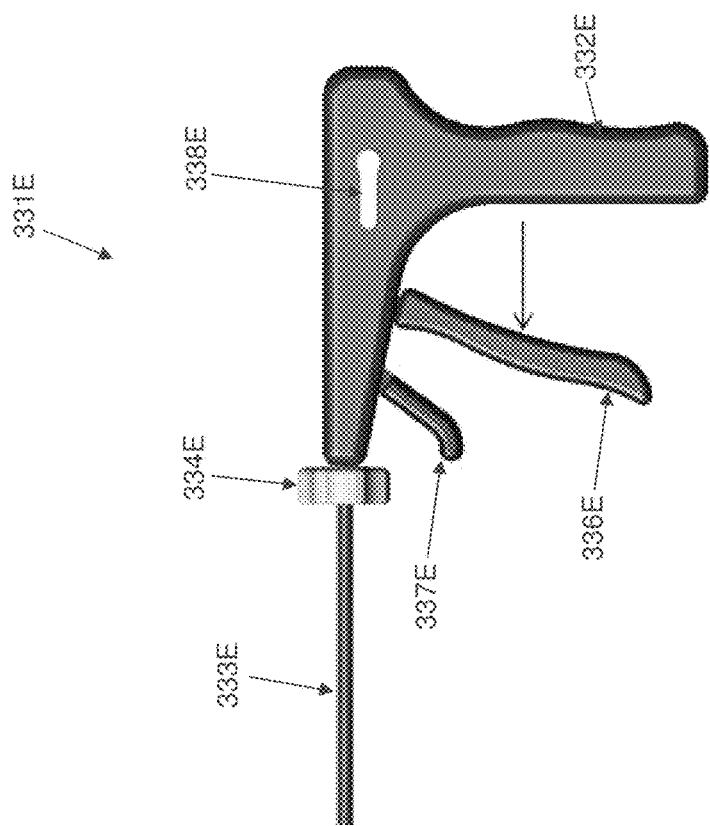
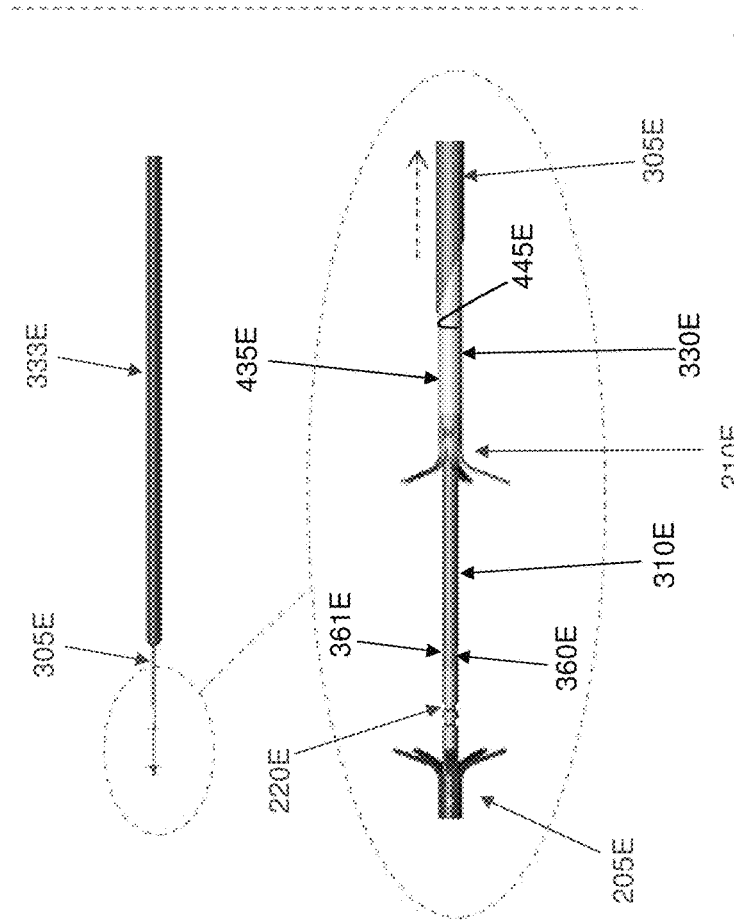
FIG. 110

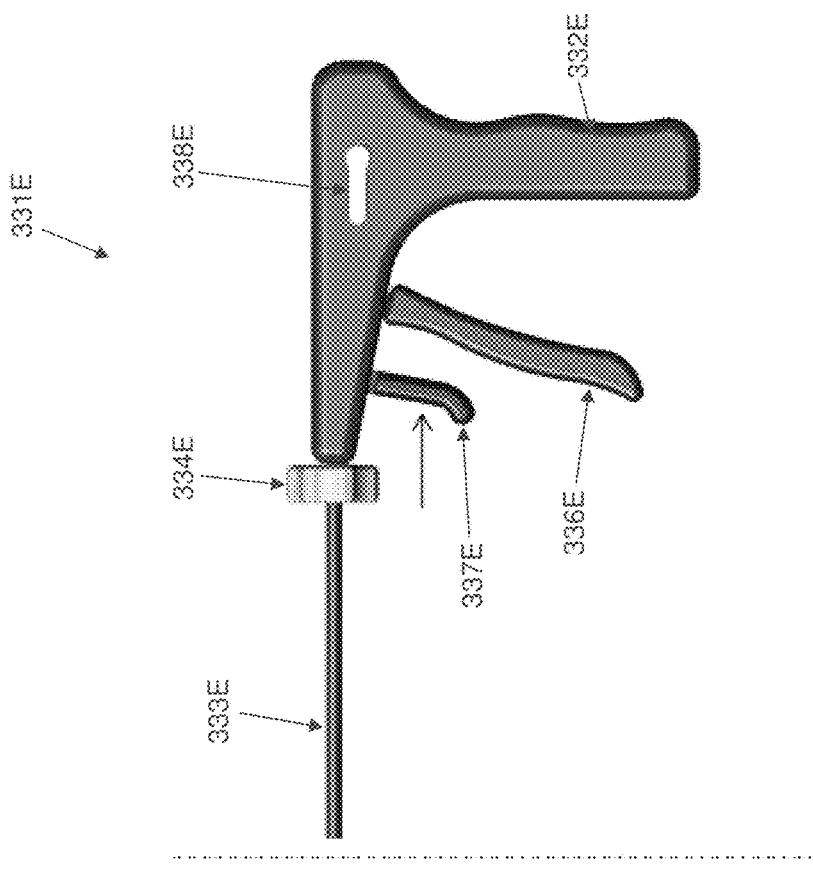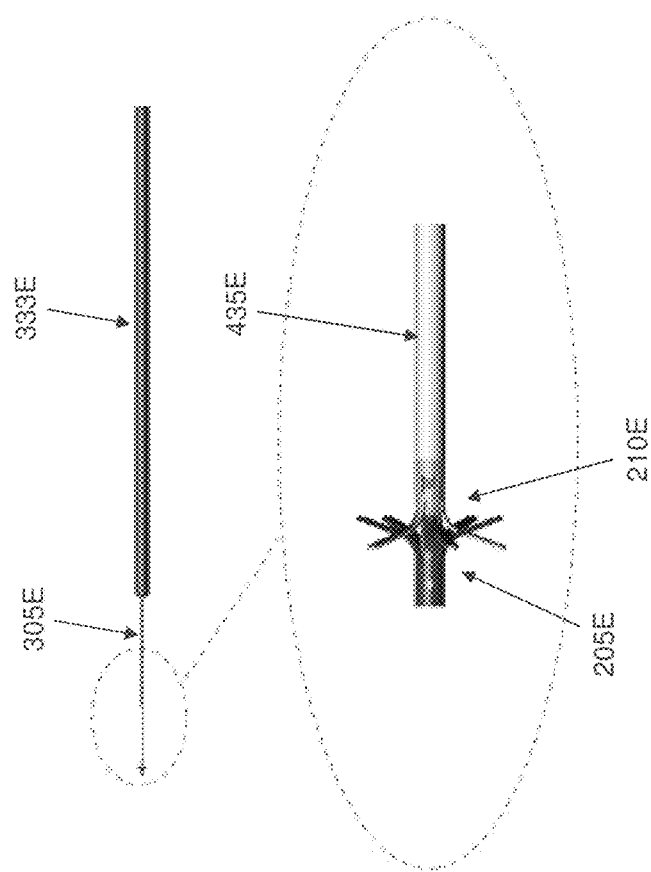
FIG. 111

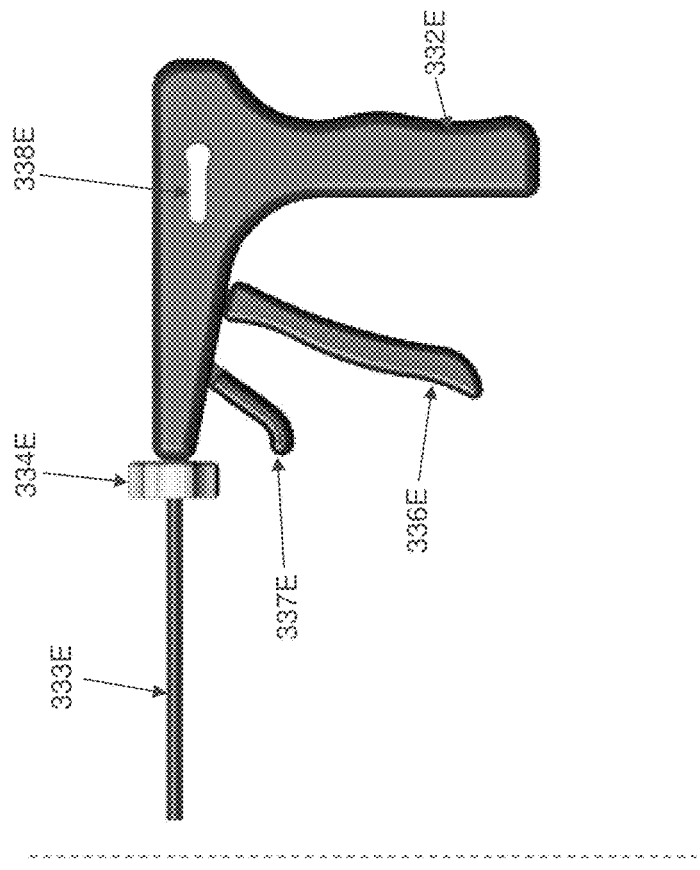
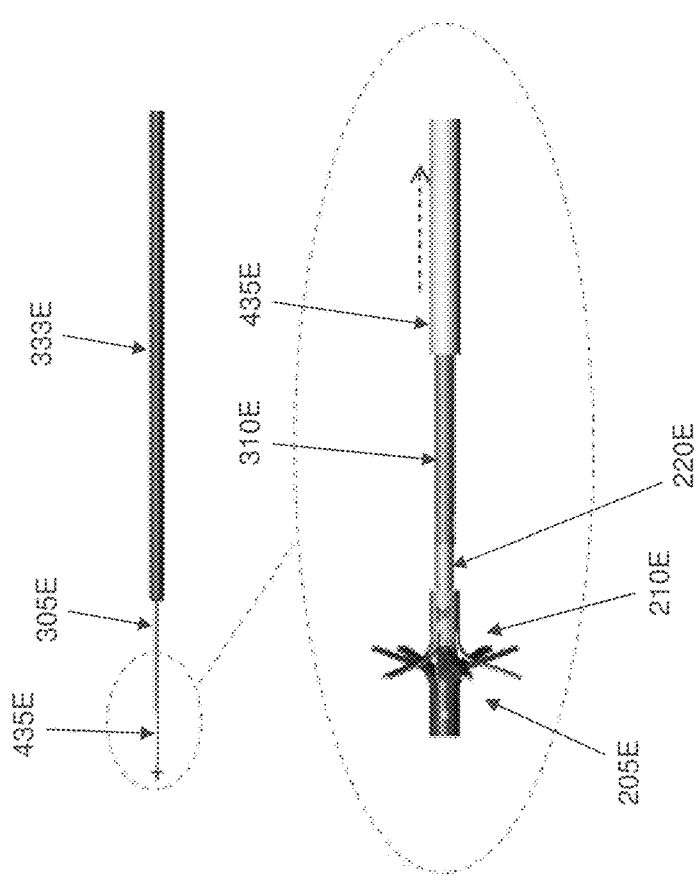
FIG. 112

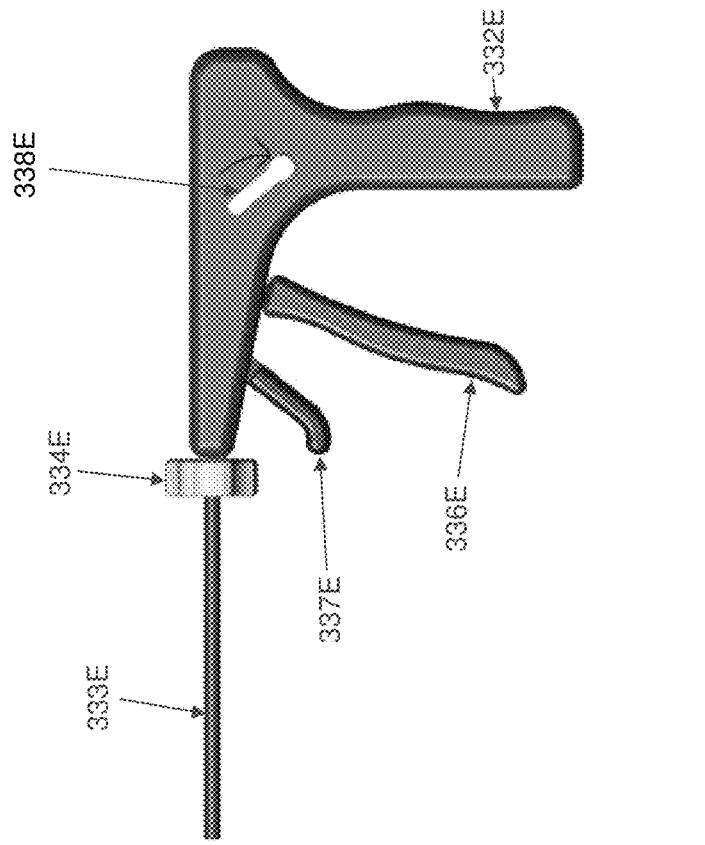
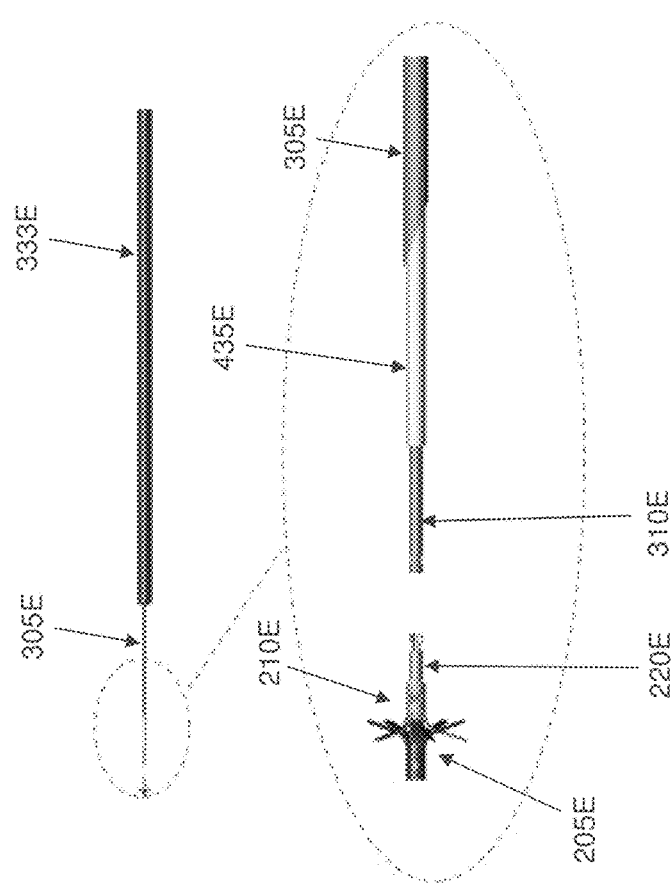
FIG. 113

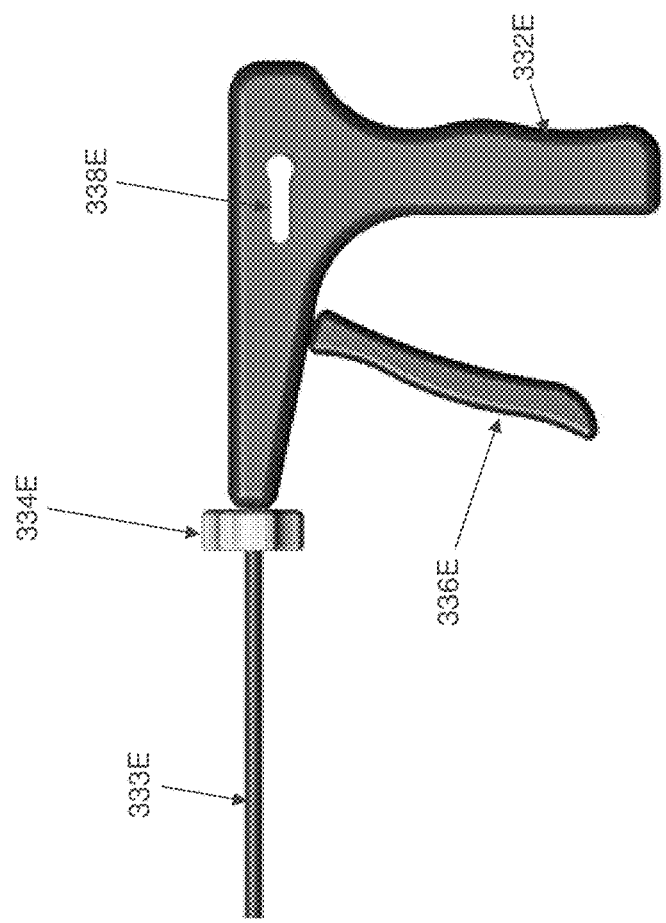
FIG. 115

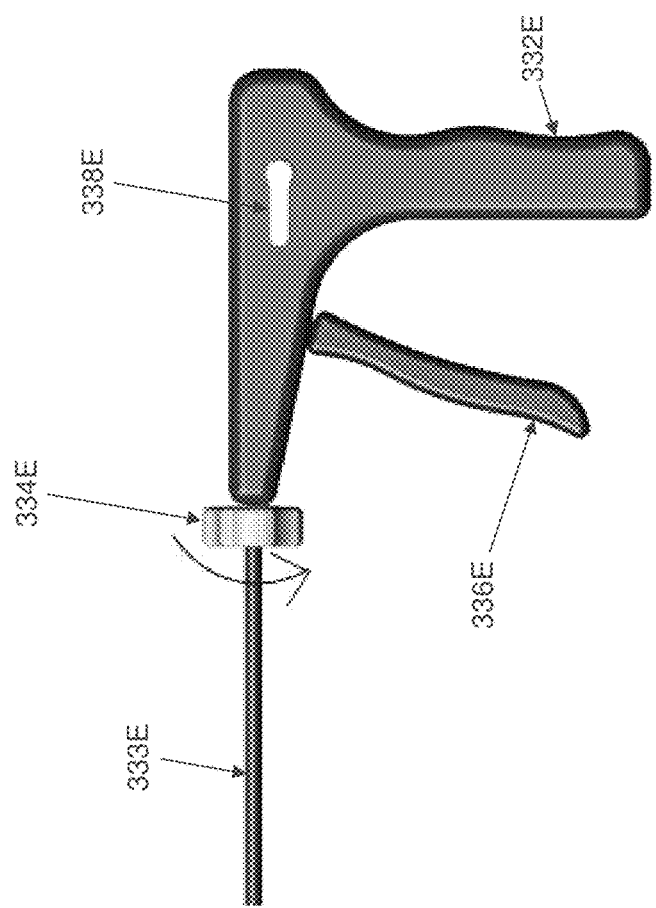
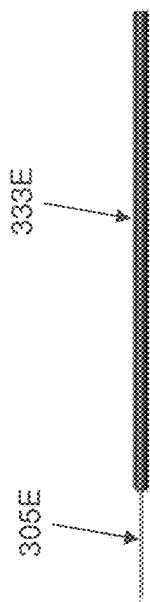
FIG. 116

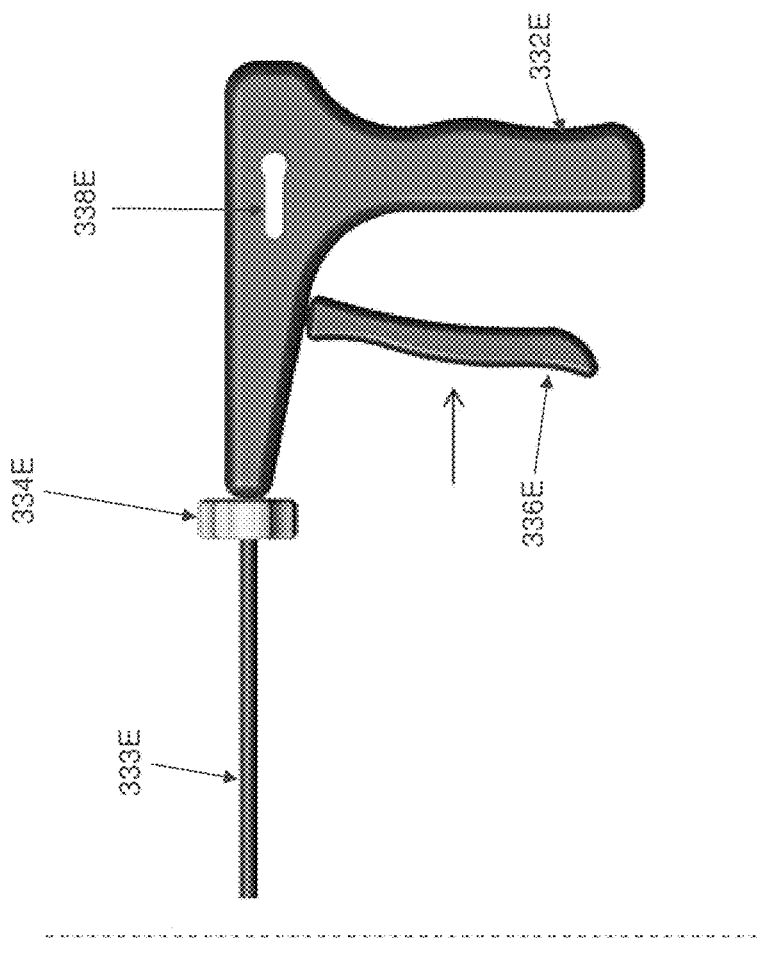
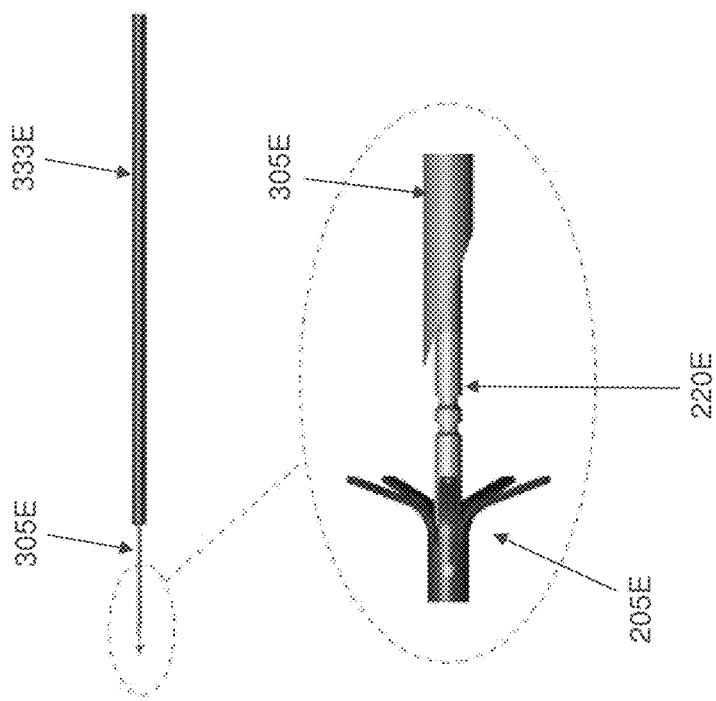
FIG. 117

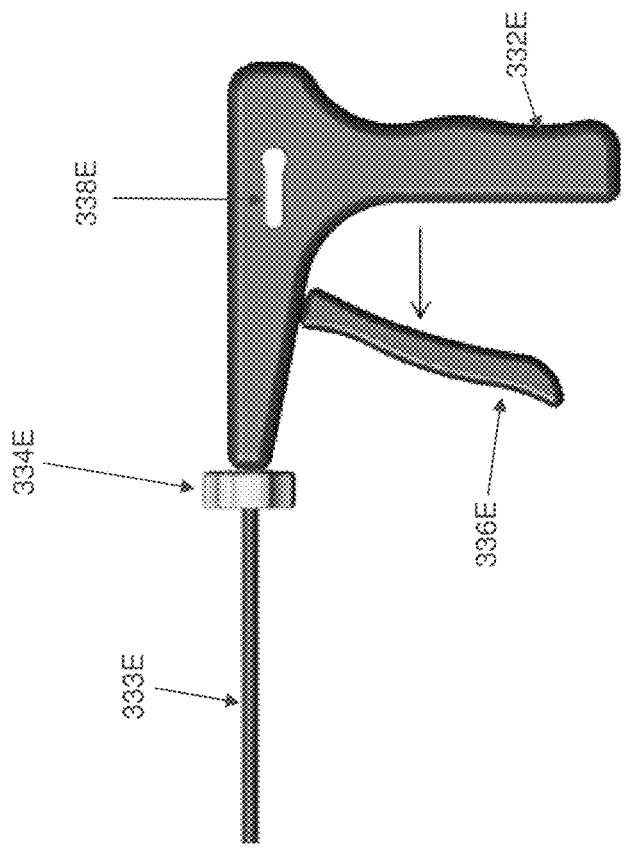
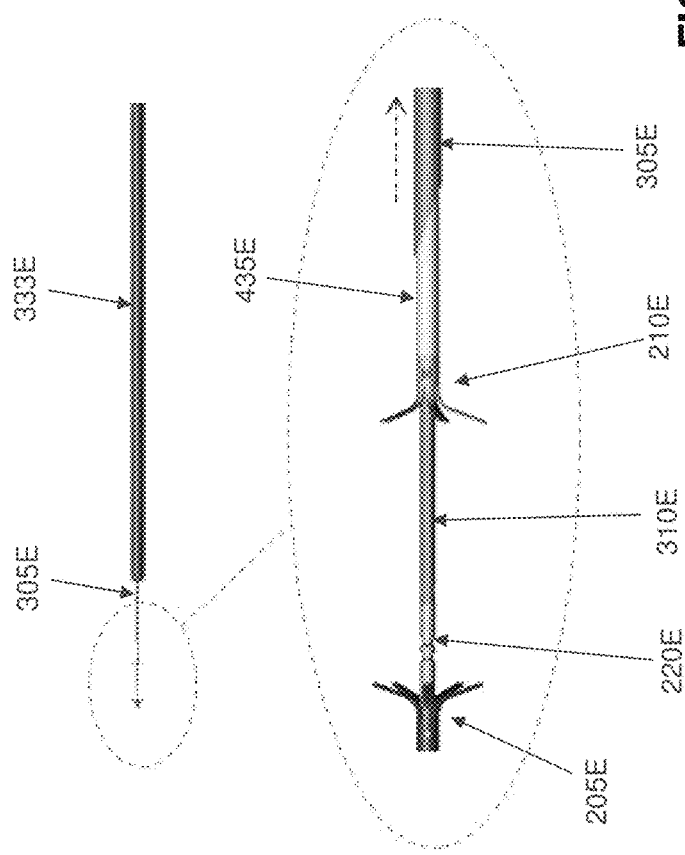
FIG. 118

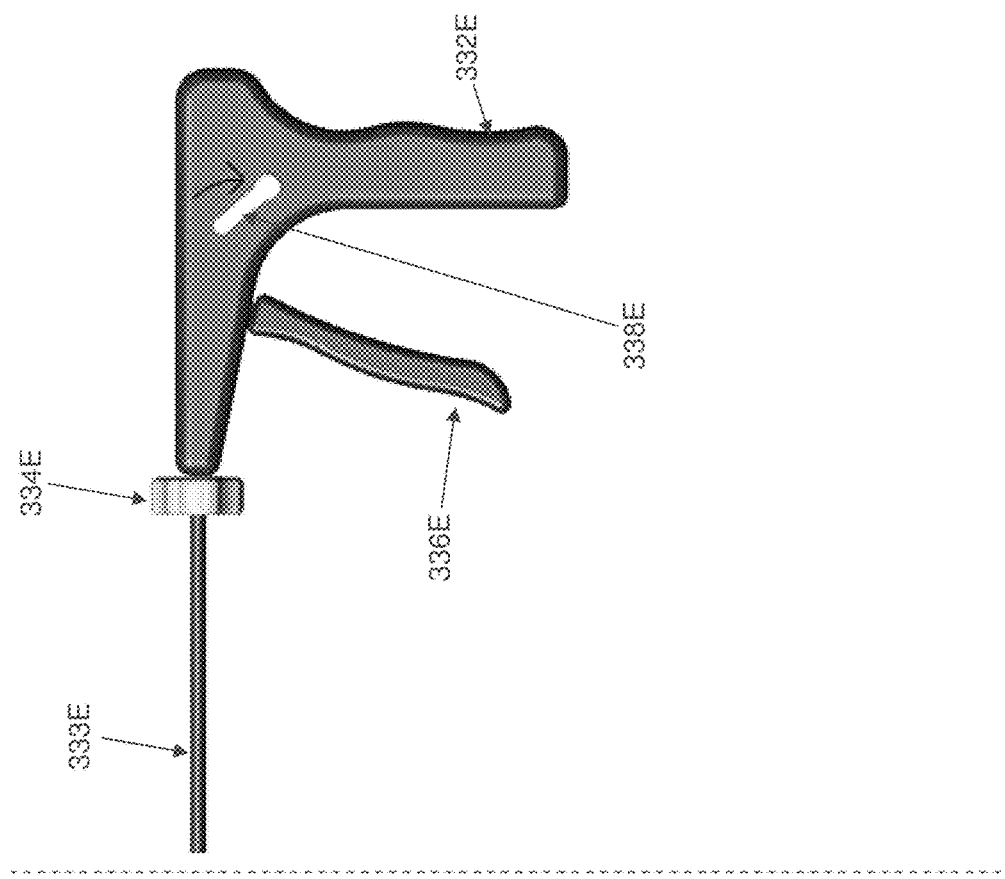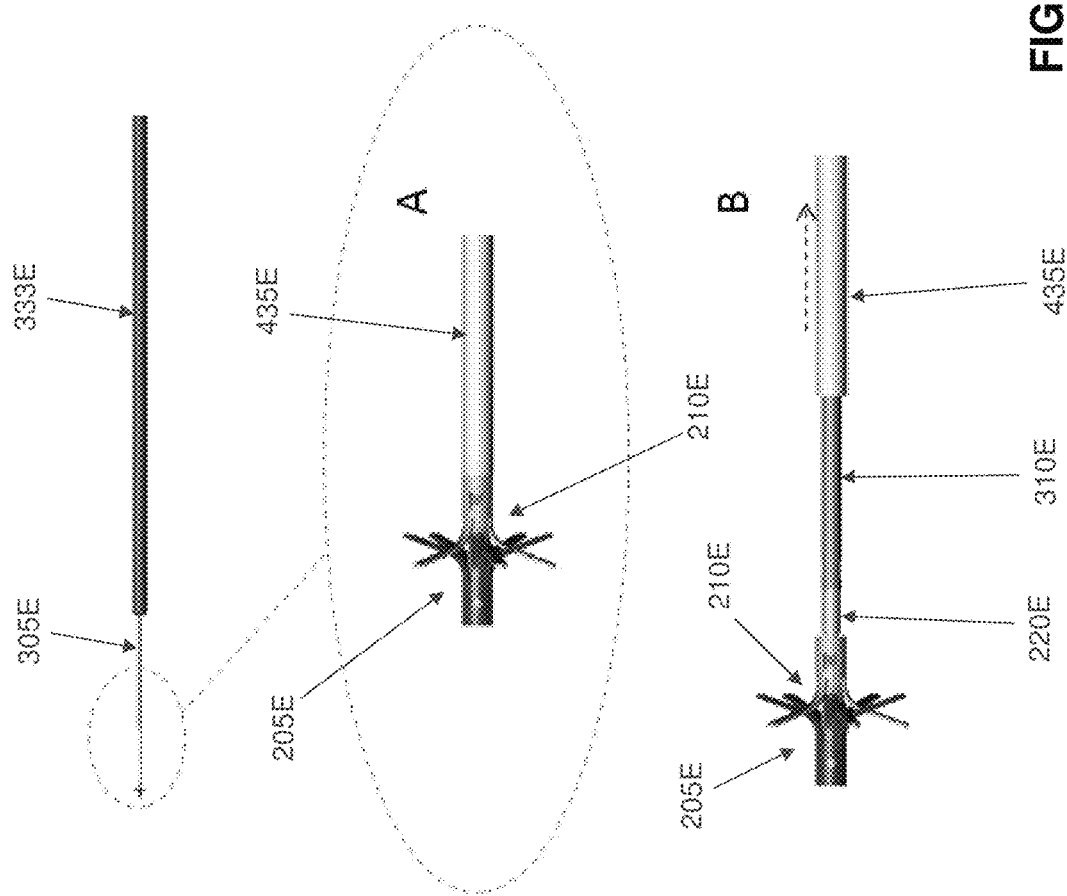
FIG. 119

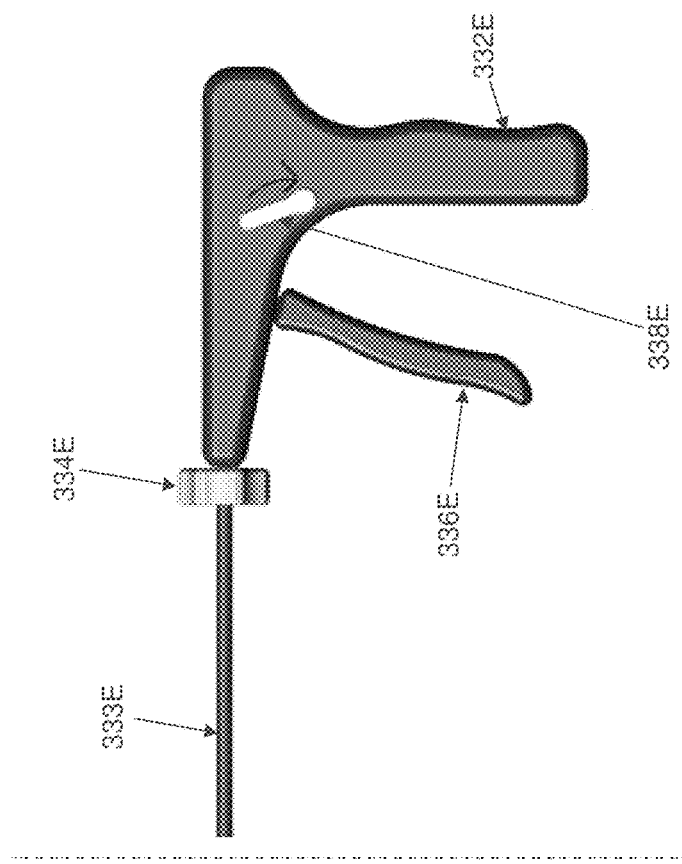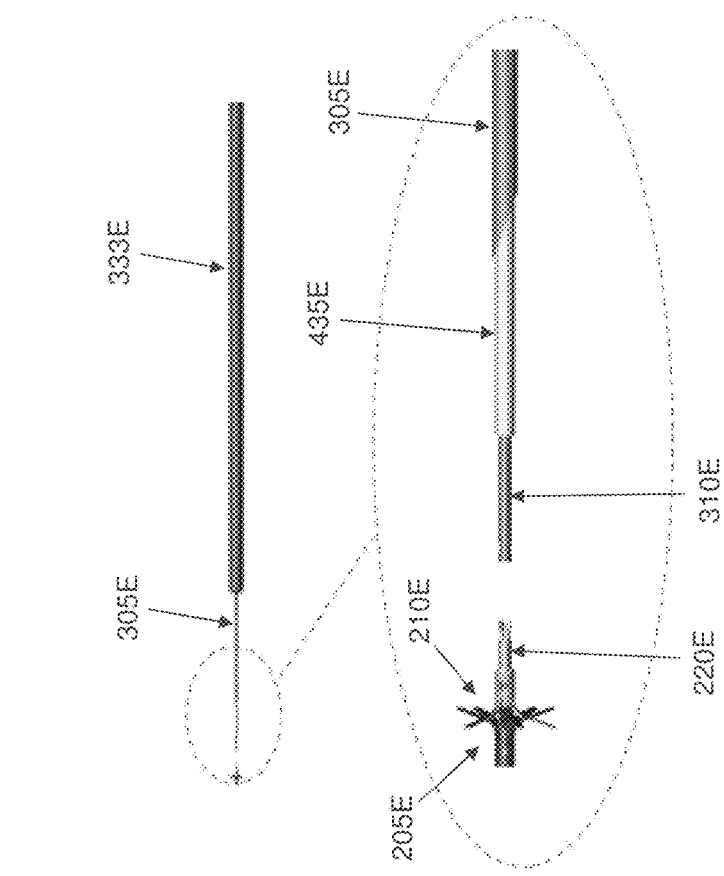
FIG. 120

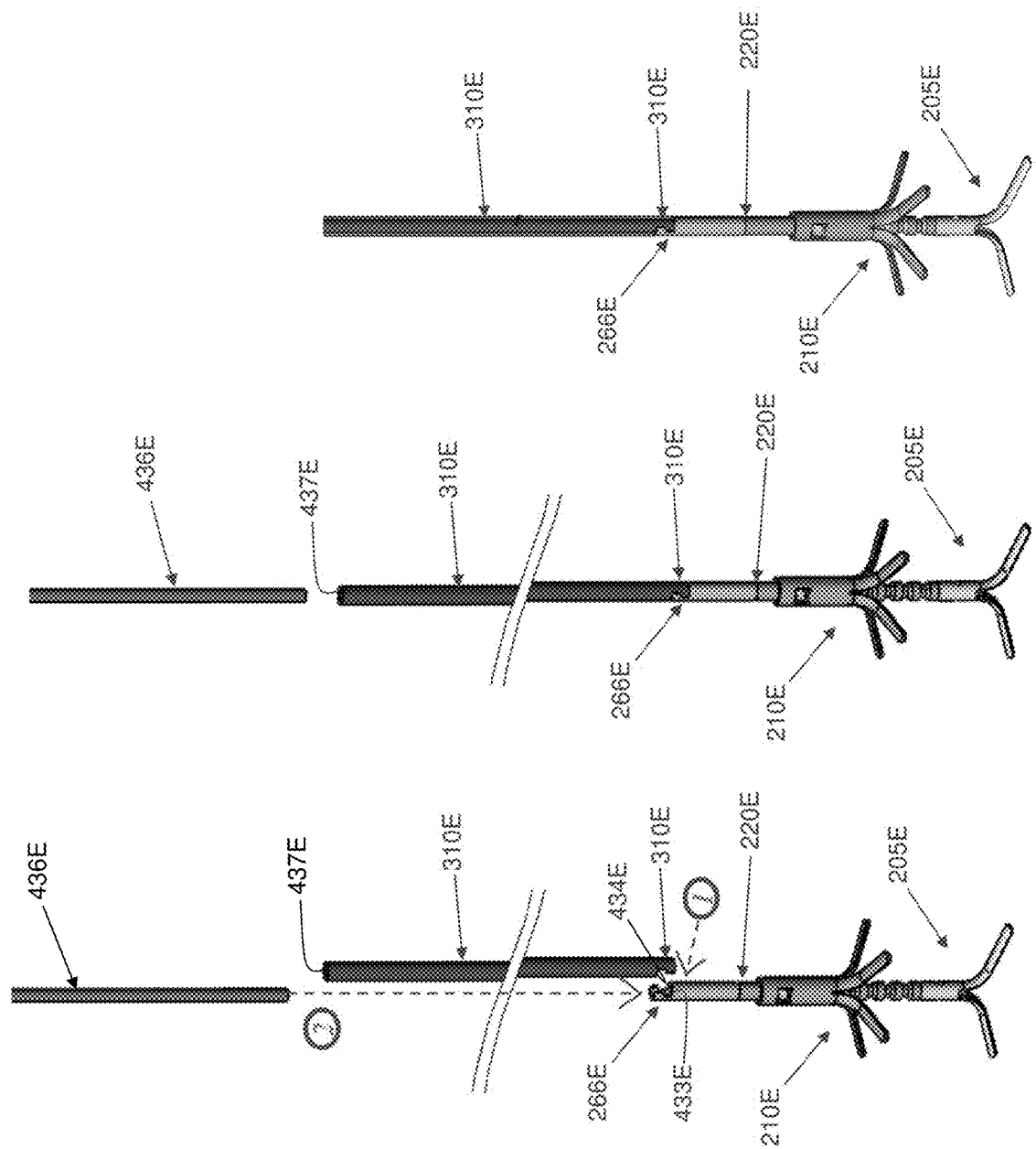

METHOD AND APPARATUS FOR CLAMPING TISSUE AND OCCLUDING TUBULAR BODY LUMENS

REFERENCE TO PENDING PRIOR PATENT APPLICATIONS

This patent application is a continuation of co-pending application Ser. No. 14/272,304, filed May 7, 2014 and claims priority to that application as well as to the other patent applications listed in the Application Data Sheet filed together with this application, all of which are hereby incorporated by reference.

FIELD OF THE INVENTION

This invention relates to surgical methods and apparatus in general, and more particularly to surgical methods and apparatus for fastening tissue to tissue or non-tissue, for example, for the occlusion of blood vessels, the treatment of varicose veins, and/or for occluding other tubular structures and/or for closing openings in tissue and/or for drug delivery. The invention also relates to a minimally invasive means for deploying such fasteners.

BACKGROUND OF THE INVENTION

Varicose Veins in General

There are three sets of veins in the legs: (i) superficial veins that lie under the skin and may be seen and felt when standing; (ii) deep veins that lie within the muscles and are not seen or felt; and (iii) perforating or connecting veins that join the two systems (i.e., the superficial veins and the deep veins).

Veins lie within all tissues. Veins return blood to the heart. When muscles in the leg contract, blood is pumped back to the heart. Valves inside the veins direct the flow of blood back to the heart.

The veins are relatively weak tubes. Under the skin there is no support for these veins, so that when the pressure in the veins is elevated, areas of weakness occur and the veins enlarge, both in size and length. In some cases the veins can become twisty and bulge significantly. This condition is commonly referred to as varicose veins.

Very small varicose veins are sometimes called spider veins. Unlike the larger varicose veins, these spider veins lie in the skin.

The cause of the increased pressure in the veins is due to the occurrence of "leaky" valves within the veins. The main valve is in the groin region, i.e., in the great sapheous vein near the sapheno-femoral junction. See FIG. 1, which shows a leg 5 of a patient, the femoral vein 10, the great saphenous vein 15, the sapheno-femoral junction 20, and the main valve 25 in the great saphenous vein near the sapheno-femoral junction. Once this main valve in the saphenous vein becomes leaky, the pressure in the vein increases and the veins below the saphenous vein start to enlarge. This causes the next set of valves in the saphenous vein to leak. The raised pressure caused by the leaky valves in the saphenous vein is transmitted to the feeder veins, which distend and their valves also malfunction and become leaky. As this process carries on down the leg, many of the valves in the leg veins become incompetent, with high pressures occurring in the veins, especially on standing.

Initially, the problem is primarily cosmetic. The veins bulge and look unsightly. However, there is commonly also discomfort in the legs upon standing. This discomfort is the result of the veins distending due to the increased pressure.

With time, the high pressure in the veins is transmitted to the surrounding tissues and skin. Small veins within the skin (i.e., spider veins) enlarge and become visible. Blood cells may escape into the tissues and break down, causing areas of discoloration. Because the pressure in the tissues is high, the skin swells and the nutrition of the skin deteriorates. This lowers the local tissue resistance and allows infection to occur. Eventually skin may break down with the development of sores (i.e., ulcers).

Incidence of Varicose Veins

Nearly 40 percent of women and 25 percent of men suffer from lower extremity venous insufficiency and associated visible varicose veins. Primary risk factors include heredity, gender, pregnancy and age. Most of these patients have long-standing leg symptoms which compromise their daily routine, with symptoms worsening during the day while the patients are at work or simply living their lives. Without varicose vein treatment, these symptoms can progress to a lifestyle-limiting condition.

Treatment of Varicose Veins

Treatment of varicose veins is undertaken for relief of the symptoms, i.e., the removal of the unsightly veins and the prevention of the discomfort and late-stage manifestations described above.

1. Non-Surgical Treatment.

The simplest treatment is a non-surgical treatment directed against the high pressure in the varicose veins. More particularly, fitted elastic stockings, strong enough to overcome the increased pressure caused by the "leaky" valves, are used. These fitted elastic stockings control the symptoms and may prevent the veins from further enlargement, however, they are not curative. Good results require consistent, every-day use of the stockings.

2. Surgical/Interventional Treatment.

The aim of the surgical/interventional treatment is (i) the elimination of the cause of the high venous pressure (i.e., the "leaky" valves at the groin); and (ii) the removal of the unsightly veins.

The early approach of "stripping" the saphenous vein (the main vein in the leg) as the sole manner of treatment has now been largely abandoned. This is because the "stripping" approach caused too much trauma and did not remove all of the superficial varicose veins: many of the superficial varicose veins were tributaries of the main superficial vein of the leg (i.e., the saphenous vein) that was stripped, and these tributary veins were not removed by this procedure.

There are currently three basic approaches for treating varicose veins: chemical—sclerorosants and glues; venous ablation using thermal treatments; and open surgery.

A. Sclerotherapy.

Sclerotherapy (the use of sclerosants) is generally used for treating the smaller varicose veins and spider veins that do not appear to be directly associated with "leaky" valves. It is primarily a cosmetic procedure.

In this approach, a sclerosant (i.e., a substance irritating to the tissues) is injected into the smaller varicose veins and spider veins, causing inflammation of the walls of these veins. As a result of this inflammation, the walls of the vein stick together and occlude the lumen of the vein so that no blood can pass through the vein. Eventually these veins shrink and disappear.

The disadvantages of sclerotherapy include: (i) in the presence of high venous pressure (i.e., with leaky valves and the larger varicose veins), the results are uncertain and the recurrence rate is high; and (ii) the erroneous injection of the sclerosant into the surrounding tissues can result in damage to the surrounding tissues, with areas of discoloration of the skin and even ulceration.

Recently, mixing the sclerosant with air to form a "foam" has been used to destroy the lining of the main vein (i.e., the saphenous vein) of the leg. To date, the results are somewhat unpredictable and there is a danger of the sclerosant escaping through the saphenous vein and into the deep veins and then embolizing into the lungs, which is harmful and dangerous for the patient.

B. Venous Ablation.

Venous ablation for varicose veins can be effected in two ways, i.e. percutaneously and endovenously.

With the percutaneous approach, the superficial smaller varicose veins and spider veins are "heated" and coagulated by shining an external laser light through the skin. However, if the veins are too large, the amount of energy needed to destroy the veins may result in damage to the surrounding tissues. Percutaneous laser treatment is primarily an alternative to the sclerotherapy discussed above, and generally suffers from the same disadvantages described above with respect to sclerotherapy.

With endovenous ablation, a special laser or radio-frequency (RF) catheter is introduced, with local anesthesia, through a needle puncture into the main superficial vein (i.e., the saphenous vein) of the leg. Entry is made in the region around the knee, and the catheter is passed up towards the groin, advancing to the site where the saphenous vein joins the deep veins at the site of the main "leaky" valves. Then, as the catheter is slowly withdrawn back through the vein, the laser light or radio-frequency (RF) energy heats up the wall of the vein, endoluminally coagulating the proteins and destroying the lining surface of the vein. The destruction of the lining surface of the vein causes the vein walls to adhere to one another, thereby eliminating the lumen within the vein and thus preventing the flow of blood. This is a process somewhat similar to sclerotherapy, but no substance is injected into the vein. This procedure takes care of the "leaky" valves and high venous pressures, however, the larger superficial varicose veins in the leg may still need to be removed. This may be done at the same time as the endovenous ablation or at a later time, either by open surgery (phlebectomy) or sclerotherapy. Placement of the laser or radio-frequency (RF) catheter is guided by ultrasound.

The advantages of endovenous laser/radio-frequency (RF) therapy include: (i) it is a minimally invasive procedure and can be done with local anesthesia, either in an operating room or a physician's office; (ii) it does not require hospitalization; (iii) it does not require open surgery with incisions; (iv) recovery is easier than with open surgery, inasmuch as most patients are back at work within a day or two; and (v) some of the prominent varicosities may disappear and may not require a secondary procedure (i.e., either phlebectomy or sclerotherapy).

The disadvantages of endovenous laser/radio-frequency (RF) therapy include: (i) generally, only one leg is done at a time; (ii) the procedure typically requires significant volumes of local anesthetic to be injected into the patient in order to prevent the complications of the heat necessary to destroy the lining of the vein; (iii) if too much heat is applied to the tissue, there can be burning in the overlying skin, with possible disfiguring, including scarring; (iv) prior to the performance of a subsequent phlebectomy procedure, an interval of up to 8 weeks is required in order to evaluate the effectiveness of the venous ablation procedure; and (v) varicosities that remain after this interval procedure still require separate procedures (i.e., phlebectomy or sclerothapy).

C. Open Surgery.

The aim of open surgery is to eliminate the "leaky" valve at the junction of the superficial and deep veins (the cause of the high venous pressure in the leg), as well as the leaky valves in the tributaries of the saphenous vein that may enlarge over the years and result in a recurrence of the varicose veins. This open surgery is directed to removal of some or all of the affected veins.

There is still some controversy as to how much of the saphenous vein needs to be removed for the best results. The current "teaching" is that removing the entire segment of saphenous vein in the thigh reduces the incidence of recurrence. However, the data for this is very weak. Removal of a very short segment of the proximal saphenous vein and the main tributaries at the sapheno-femoral junction is the alternative procedure and, provided that it is combined with removal of all visible varicosities, the results are very similar to removal of the entire thigh segment of the saphenous vein. The advantage of the latter procedure is the increased preservation of the saphenous vein which, in 50-60% or more of varicose vein patients, is not involved in the varicose vein process and is otherwise normal and hence usable for other procedures (such as a bypass graft in the heart or limbs).

The surgery is performed in the operating room under light general or regional (spinal or epidural) anesthesia. An incision (e.g., 1-2 inch) is made in the groin crease and the veins dissected out and the proximal saphenous vein and tributaries excised. The wound is closed with absorbable sutures from within. Once this is completed, small (e.g., 2-4 mm) stab wounds are made over any unsightly varicose veins (these veins are marked out just prior to the surgery with the patient standing) and the varicose veins are completely removed. The small stab wounds associated with removal of the marked-out veins are generally so small that they typically do not require any stitches to close them. When all the previously marked-out veins are removed, the wounds are cleaned and a dressing applied. The leg is wrapped in elastic bandages (e.g., Ace wraps).

In the post-operative care, the dressings and Ace wraps are usually changed in the doctor's office at the first post-operative visit, typically within 24 hours of the open surgical procedure. The patient and a family member or friend is instructed on proper care of the wounds. A simple dressing is applied to cover the small wounds in the legs for the next 2-3 days. After 2-3 days no further treatment is generally required. Recovery is generally rapid, with the patient returning to work within 5-7 days.

The advantages of open surgery include: (i) varicose veins of both extremities can be done at a single operation, which generally takes 1-2 hours; (ii) the procedure typically does not require hospitalization and is an "out patient" procedure; (iii) the wounds are minimal, with minimal discomfort which is easily managed with oral analgesics (i.e., pain medicine); (iv) the results are generally excellent, with a minimum of recurrence (the results of open surgery remain the "gold standard" against which the sclerotherapy and laser/radio-frequency (RF) venous ablation therapies are compared); (v) recurrent or residual (i.e., those missed at surgery) veins are generally managed with sclerotherapy or phlebectomy under local anesthesia in a doctor's office or in an ambulatory procedure room; and (vi) the saphenous vein, if normal and without varicosities, is preserved and is therefore available for use (e.g., for bypass surgery) in the future if it should be needed.

The disadvantages of open surgery include: (i) it is an open surgical procedure requiring an anesthetic (either general or regional), with its associated discomfort and with its attendant risks (which may depend on the health or age of the patient); and (ii) recovery generally takes 3-5 days.

Thus it will be seen that varicose veins present a significant problem for many patients which must be addressed, and all of the current procedures for treating varicose veins suffer from a number of significant disadvantages.

Accordingly, it would be advantageous to provide new and improved surgical methods and apparatus for the occlusion of blood vessels and the treatment of varicose veins, and/or for occluding other tubular structures and/or for closing openings in structures and/or for securing at least two objects together.

It would also be advantageous to provide new and improved surgical methods and apparatus for fastening mechanical structures to tissues or blood vessels, for example, for drug delivery.

SUMMARY OF THE INVENTION

The present invention provides a new and improved approach for treating varicose veins and other blood vessels.

More particularly, the present invention comprises the provision and use of a novel occluder which is used to occlude a vein (e.g., the proximal saphenous vein, the small saphenous vein, tributaries, the perforator veins, etc.) so as to restrict blood flow through the vein and thereby treat varicose veins below the point of occlusion. Significantly, the novel occluder is configured to be deployed using a minimally-invasive approach (i.e., either percutaneously or endoluminally), with visualization being provided by ultrasound and/or other visualization apparatus (e.g., CT, MRI, X-ray etc.). As a result, the novel treatment can be provided in a doctor's office, with minimal local anesthetic, and effectively no post-operative care.

The present invention also provides new and improved surgical methods and apparatus for occluding other tubular structures and/or for closing openings in structures and/or for securing at least two objects together.

And the present invention provides new and improved surgical methods and apparatus for fastening mechanical structures to tissues or blood vessels, for example, for drug delivery.

Significantly, the present invention may be practiced under direct visualization (e.g., during "open" surgery) or under indirect visualization (e.g., during laparoscopic surgery where visualization is provided through the use of a scope, or during percutaneous surgery where visualization is provided through the use of imaging apparatus such as an ultrasound imager, an X-ray imager, etc.).

In one form of the invention, there is provided apparatus for occluding a blood vessel, the apparatus comprising:

an occluder, the occluder being configured so that at least a portion of the occluder may assume (i) a diametrically-reduced configuration for disposition within the lumen of a tube, and (ii) a diametrically-expanded configuration for disposition adjacent to the blood vessel, such that when said at least a portion of the occluder is in its diametrically-expanded configuration adjacent to the blood vessel, the occluder will cause occlusion of the blood vessel.

In another form of the invention, there is provided a method for occluding a blood vessel, the method comprising:

providing apparatus comprising:

an occluder, the occluder being configured so that at least a portion of the occluder may assume (i) a diametrically-reduced configuration for disposition within the lumen of a tube, and (ii) a diametrically-expanded configuration adjacent to the blood vessel, such that when said at least a portion of the occluder is in its diametrically-expanded configuration adjacent to the blood vessel, the occluder will cause occlusion of the blood vessel; and positioning the occluder adjacent to the blood vessel so as to cause occlusion of the blood vessel.

In another form of the invention, there is provided apparatus for delivering a substance to a location adjacent to a blood vessel, the apparatus comprising:

a carrier, the carrier being configured so that at least a portion of the carrier may assume (i) a diametrically-reduced configuration for disposition within the lumen of a tube, and (ii) a diametrically-expanded configuration for disposition adjacent to the blood vessel, such that when the substance is attached to the carrier and said at least a portion of the carrier is in its diametrically-expanded configuration adjacent to the blood vessel, the substance will be disposed adjacent to the blood vessel.

In another form of the invention, there is provided a method for delivering a substance to a location adjacent to a blood vessel, the method comprising:

providing apparatus comprising:

a carrier, the carrier being configured so that at least a portion of the carrier may assume (i) a diametrically-reduced configuration for disposition within the lumen of a tube, and (ii) a diametrically-expanded configuration for disposition adjacent to the blood vessel, such that when the substance is attached to the carrier and said at least a portion of the carrier is in its diametrically-expanded configuration adjacent to the blood vessel, the substance will be disposed adjacent to the blood vessel; and positioning the carrier adjacent to the blood vessel so that the substance is disposed adjacent to the blood vessel.

In another form of the invention, there is provided apparatus for occluding a space between a first structure and a second structure, said apparatus comprising:

an occluder, said occluder comprising a distal implant and a proximal implant, wherein:

said distal implant comprises a body and a locking shaft mounted to said body, wherein said body of said distal implant comprises a plurality of legs which may assume (i) a diametrically-reduced configuration for disposition within the lumen of a tube, and (ii) a diametrically-expanded configuration for disposition against the first structure, and further wherein said locking shaft comprises a first locking element for selective connection to said proximal implant and a second locking element for selective connection to an inserter for deploying said occluder; and said proximal implant comprises a body having an opening, wherein said body of said proximal implant comprises a plurality of legs which may assume (i) a diametrically-reduced configuration for disposition within the lumen of a tube, and (ii) a diametrically-expanded configuration for disposition against the second structure, and further wherein said body of said proximal implant comprises a third locking element for selective connection to said first locking element of said distal implant; wherein said locking shaft of said distal implant is slidably receivable within said opening in said body of said proximal implant, and further wherein said first locking element of said distal implant and said third locking element of said proximal implant are selectively engagable with one another so as to hold said distal implant and said proximal implant in fixed position relative to one another.

In another form of the invention, there is provided a method for occluding a space between a first structure and a second structure, said method comprising:

providing apparatus comprising:
an occluder, said occluder comprising a distal implant and a proximal implant, wherein:

said distal implant comprises a body and a locking shaft mounted to said body, wherein said body of said distal implant comprises a plurality of legs which may assume (i) a diametrically-reduced configuration for disposition within the lumen of a tube, and (ii) a diametrically-expanded configuration for disposition against the first structure, and further wherein said locking shaft comprises a first locking element for selective connection to said proximal implant and a second locking element for selective connection to an inserter for deploying said occluder; and said proximal implant comprises a body having an opening, wherein said body of said proximal implant comprises a plurality of legs which may assume (i) a diametrically-reduced configuration for disposition within the lumen of a tube, and (ii) a diametrically-expanded configuration for disposition against the second structure, and further wherein said body of said proximal implant comprises a third locking element for selective connection to said first locking element of said distal implant;

wherein said locking shaft of said distal implant is slidably receivable within said opening in said body of said proximal implant, and further wherein said first locking element of said distal implant and said third locking element of said proximal implant are selectively engagable with one another so as to hold said distal implant and said proximal implant in fixed position relative to one another; and positioning said occluder so that said plurality of legs of said distal implant are disposed against the first structure, said plurality of legs of said proximal implant are disposed against the second structure, and said locking shaft extends across the space between the first structure and the second structure.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 6 and 7 are schematic views showing an exemplary syringe-type inserter which may be used to deploy the occluder shown in FIGS. 2-4;

FIGS. 8-10 are schematic views showing an occluder occluding a blood vessel in accordance with another form of the present invention;

FIGS. 18-20 are schematic views showing the occluders of the types shown in FIGS. 15-17 occluding a blood vessel in accordance with yet another form of the present invention;

FIGS. 21-24 are schematic views showing an occluder occluding a blood vessel in accordance with another form of the present invention;

FIGS. 25-27 are schematic views showing an occluder occluding a blood vessel in accordance with still another form of the present invention;

FIGS. 34 and 35 are schematic views showing a drug/cellular delivery body being attached to a blood vessel in accordance with one form of the present invention;

FIGS. 36 and 37 are schematic views showing a drug/cellular delivery body being attached to a blood vessel in accordance with another form of the present invention;

FIGS. 38 and 39 are schematic views showing a drug/cellular delivery body being attached to a blood vessel in accordance with still another form of the present invention;

FIGS. 40 and 41 are schematic views showing a drug/cellular delivery body being attached to a blood vessel in accordance with yet another form of the present invention;

FIGS. 42-48 are schematic views showing a two-part occluder formed in accordance with another form of the present invention;

FIGS. 59-82 are schematic views showing the two-part occluder of FIGS. 42-48 being deployed across a blood vessel using the installation apparatus of FIGS. 49-58;

FIGS. 91-94 are schematic views showing yet another two-part occluder formed in accordance with the present invention;

FIGS. 95-100 are schematic views showing another two-part occluder formed in accordance with the present invention;

FIGS. 101-104 are schematic views showing another two-part occluder formed in accordance with the present invention;

FIGS. 105-113 are schematic views showing an installation apparatus for deploying the two-part occluder shown in FIGS. 101-104;

FIGS. 114-120 are schematic views showing another installation apparatus for deploying the two-part occluder shown in FIGS. 101-104;

FIGS. 124-126 are schematic views showing means for securing the two-part occluder shown in FIGS. 121-123 to an installation apparatus;

DETAILED DESCRIPTION OF THE PREFERRED EMBODIMENTS

The present invention provides a new and improved approach for treating varicose veins and other blood vessels.

More particularly, the present invention comprises the provision and use of a novel occluder which is used to occlude a vein (e.g., the proximal saphenous vein, the small saphenous vein, tributaries, the perforator veins, etc.) so as to restrict blood flow through the vein and thereby treat varicose veins below the point of occlusion. Significantly, the novel occluder is configured to be deployed using a minimally-invasive approach (i.e., either percutaneously or endoluminally), with visualization being provided by ultrasound and/or other visualization apparatus (e.g., CT, MRI, X-ray etc.). As a result, the novel treatment can be provided in a doctor's office, with minimal local anesthetic, and effectively no post-operative care.

The present invention also provides new and improved surgical methods and apparatus for occluding other tubular structures and/or for closing openings in structures and/or for securing at least two objects together.

And the present invention provides new and improved surgical methods and apparatus for fastening mechanical structures to tissues or blood vessels, for example, for drug delivery.

Percutaneous Approach

In the percutaneous approach, the occluder is delivered by percutaneously advancing the occluder through the skin, through intervening tissue and then across some or all of the blood vessel (e.g., the great saphenous vein near the sapheno-femoral junction) so as to occlude the blood vessel. This occlusion (or multiple of these occlusions) will thereby treat varicose veins. In one form of the invention, the occluder is configured to occlude the vein by compressing the vein and closing down its lumen; and in another form of the invention, the occluder is configured to occlude the vein by depositing a mass within the lumen of the vein so as restrict blood flow through the lumen of the vein. The occlusion of the lumen may be complete or partial. If the occlusion is partial, some blood may continue to flow in the vein. Such partial occlusion can act to relieve some of the pressure on the valve, thereby improving its function. In some applications, an occlusion of 70% or greater of the lumen may be desired and realized based on the current invention. In other applications, an occlusion of 80% or greater of the lumen may be desired and realized based on the current invention. In one embodiment, the occlusion pressure applied may be greater than 40 mm of mercury. In another embodiment of the present invention, the occlusion pressure may be greater than the pressure of the typical blood flow in the vein.

Figure 1:
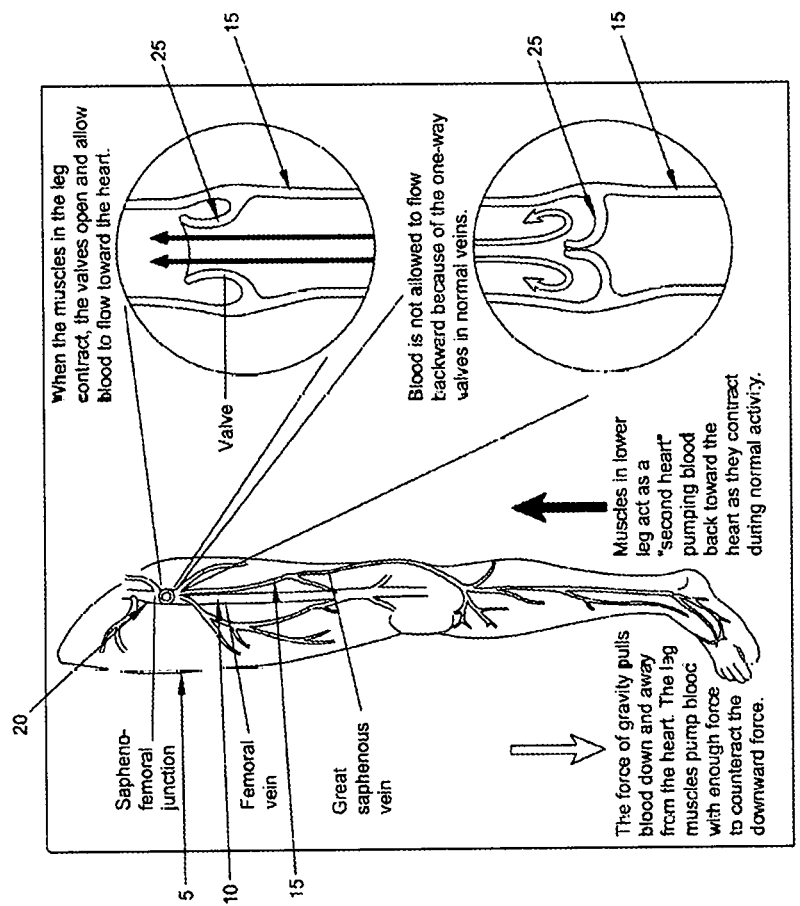
FIG. 1 is a schematic view showing various aspects of the venous system of the leg.
Figure 3:
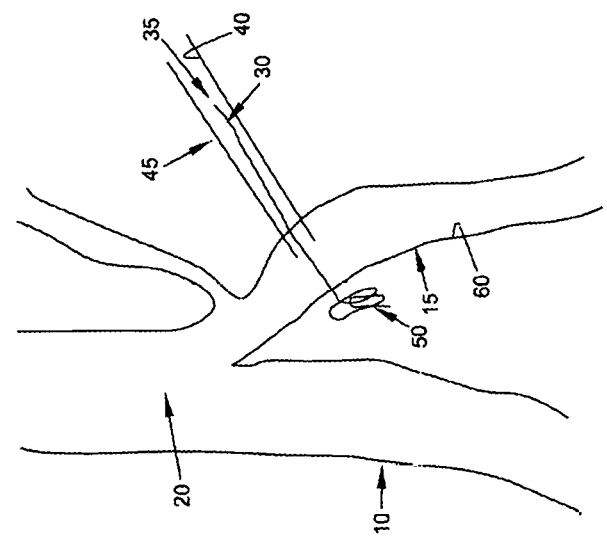
FIGS. 2-4 are schematic views showing an occluder occluding a blood vessel in accordance with one form of the present invention.
Figure 2:
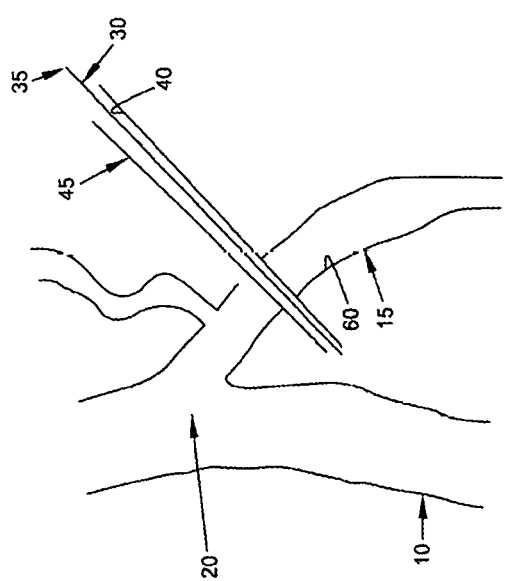
Figure 4:
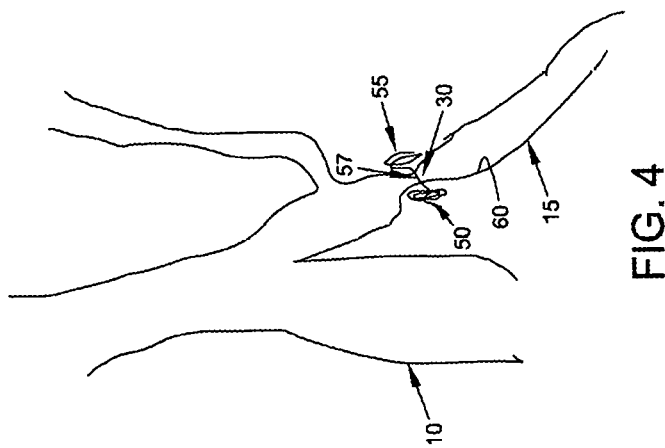
Figure 11:
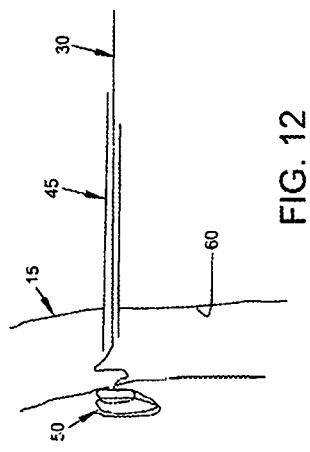
FIGS. 11-14 are schematic views showing an occluder occluding a blood vessel in accordance with still another form of the present invention.
Figure 12:
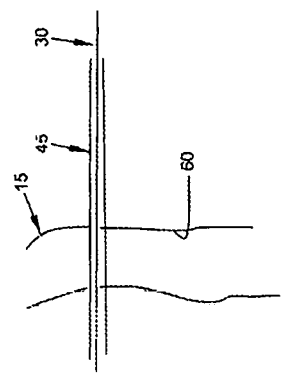
Figure 13:
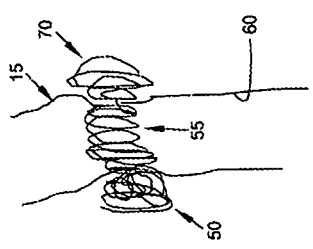

Looking first at FIGS. 2-4, in one form of the invention, there is provided an occluder 30. Occluder 30 comprises an elastic filament 35 which, in an unconstrained condition, comprises a generally non-linear configuration (e.g., a coiled mass) but which, when properly restrained, can maintain a linear configuration (e.g., in the narrow lumen 40 of a needle 45, or where the filament is formed out of a shape memory material, by appropriately controlling its temperature and hence its shape); when the restraint is removed (e.g., the elastic filament 35 is extruded from the constraining lumen 40 of the needle 45, or the temperature of the shape memory material is elevated such as by body heat), elastic filament 35 will return to its generally non-linear configuration, whereby to provide enlarged masses for occluding the vein.

In one form of the invention, the occluder is formed out of a shape memory material (e.g., a shape memory alloy such as Nitinol, or a shape memory polymer), with the shape memory material being configured to provide superelasticity, or temperature-induced shape changes, or both).

In one preferred method of use, the occluder 30 is installed in the narrow lumen 40 of a needle 45 (FIG. 2), the needle is introduced percutaneously and advanced across the vein which is to be occluded (e.g., the great saphenous vein 15), a first length of the occluder is extruded from the needle on the far side of the vein so that a portion of the occluder is restored to a coiled mass configuration 50 on the far side of the vein (FIG. 3), the needle is withdrawn back across the vein, and then the remainder of the occluder is extruded on the near side of the vein (FIG. 4), whereupon the remainder of the occluder is restored to a coiled mass configuration 55, with a portion 57 of the occluder extending across the lumen 60 of the vein 15, and with the portions of the occluder on the far and near sides of the vein (i.e., the coiled masses 50 and 55, respectively) being drawn toward one another under the coiling force inherent in the elastic filament so as to compress the vein there between and occlude its lumen 60, whereby to restrict blood flow through the vein and thereby treat the varicose veins.

As noted above, occluder 30 may be formed out of a shape memory material (e.g., a shape memory alloy such as Nitinol, or a shape memory polymer, etc.), with the shape memory material being configured to provide superelasticity, or temperature-induced shape changes, or both).

Figure 5:
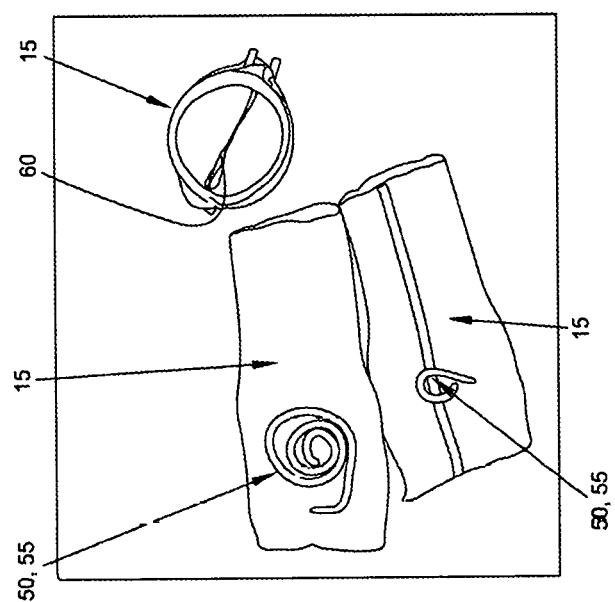
FIG. 5 is a schematic view showing one possible construction for the occluder shown in FIGS. 2-4.

In the form of the invention shown in FIGS. 2-4, occluder 30 is formed out of a single elastic filament 35, and a shape transition (i.e., from substantially linear to a pair of opposing coiled masses 50, 55) is used to cause occlusion of the target blood vessel. In this respect it should be appreciated that the aforementioned coiled masses 50, 55 may comprise substantially random turns of the elastic filament arranged in a substantially three-dimensional structure (i.e., somewhat analogous to a ball of string), or the coiled masses 50, 55 may comprise highly reproducible structures such as loops, coils, etc., and these loops, coils, etc. may or may not assume a substantially planar structure. See, for example, FIG. 5, where coiled masses 50, 55 comprise highly reproducible loops and coils.

FIGS. 6 and 7 show an exemplary syringe-type inserter 65 which may be used to deploy the novel occluder of the present invention. The syringe-type inserter 65 may contain one occluder 30 or multiple pre-loaded occluders 30, e.g., where syringe-type inserter 65 comprises multiple occluders 30, the occluders may be disposed serially within the syringe-type inserter, or they may be disposed parallel to one another within the syringe-type inserter (i.e., in the manner of a "Gatling gun" disposition), etc. When the syringe-type inserter 65 is activated, an occluder 30 is deployed out of the distal end of needle 45.

In FIGS. 2-4, occluder 30 is shown occluding the vein by compressing the vein between the two coiled masses 50, 55, whereby to close down its lumen 60. However, in another form of the invention, the occluder 30 can be used to occlude the vein without compressing the vein. This is done by depositing a coiled mass within the lumen of the vein, whereby to restrict blood flow through the lumen of the vein. More particularly, and looking now at FIGS. 8-10, in this form of the invention, the needle 45 is passed into the interior of the vein 15 and one coiled mass 50 of the occluder 30 is extruded into the lumen 60 of the vein (FIG. 8) so as to occlude the lumen of the vein, the needle 45 is withdrawn to the near side of the vein (FIG. 9), and then another coiled mass 55 is disposed on the near side of the vein (FIG. 10), with the portion 57 of the occluder extending through the side wall of the vein so as to stabilize the occluder relative to the vein (i.e., so as to attach the occluder to the vein and prevent the occluder from moving relative to the vein).

Figure 14:
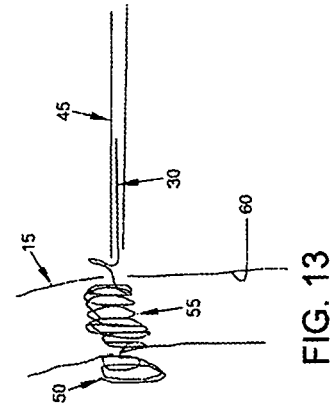

FIGS. 11-14 show another approach where a coiled mass of the occluder 30 is deposited within the interior of the blood vessel so as to obstruct blood flow through the vessel. More particularly, in this form of the invention, the needle 45 is passed completely through the vein (FIG. 11), a coiled mass 50 of the occluder is deposited on the far side of the vein (FIG. 12), the needle is withdrawn into the interior of the vein where another coiled mass 55 of the occluder is deposited (FIG. 13), and then the needle is withdrawn to the near side of the vein where another coiled mass 70 of the occluder 30 is deposited (FIG. 14). In this form of the invention, coiled mass 55 resides within the lumen 60 of the vein and obstructs blood flow while coiled masses 50 and 70 compress the vein inwardly and stabilize the disposition of the intraluminal coiled mass 55.

Figure 15:
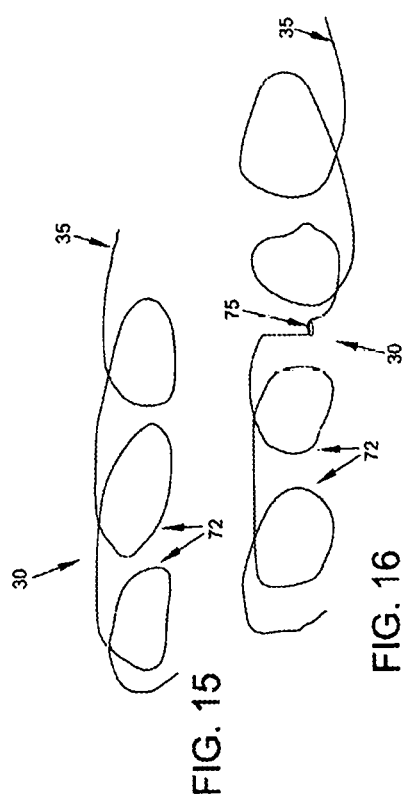
FIGS. 15-17 are schematic views showing other possible constructions for the occluder of the present invention.
Figure 16:
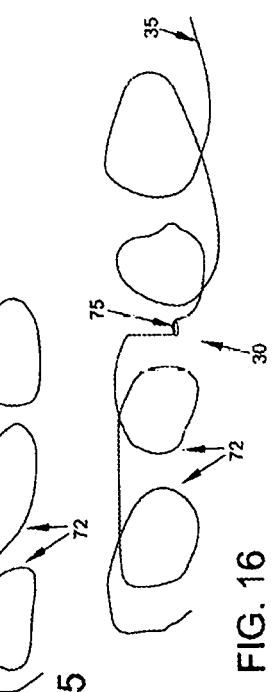

FIGS. 15 and 16 show occluders 30 formed out of a single strand of elastic filament. In FIG. 15, the occluder 30 comprises a relatively ordered coil where the turns 72 of the coil are unidirectional. In FIG. 16, the occluder 30 comprises another relatively ordered coil but where the turns rotate in opposite directions on different sides of a midpoint 75. Of course, it should also be appreciated that the occluder 30 can be constructed so as to form a relatively disordered coil, i.e., where the strand of the filament follows a relatively random pattern (see, for example, the disordered coils illustrated in FIGS. 8-10). Indeed, where it is desired that the mass of the reformed coil itself provide a flow obstruction (e.g., where the reformed coil is disposed intraluminally so as to impede blood flow through the vein), it is generally preferred that the elastic filament reform into a relatively disordered coil having a relatively random disposition, since this can provide a denser filament configuration.

Figure 17:
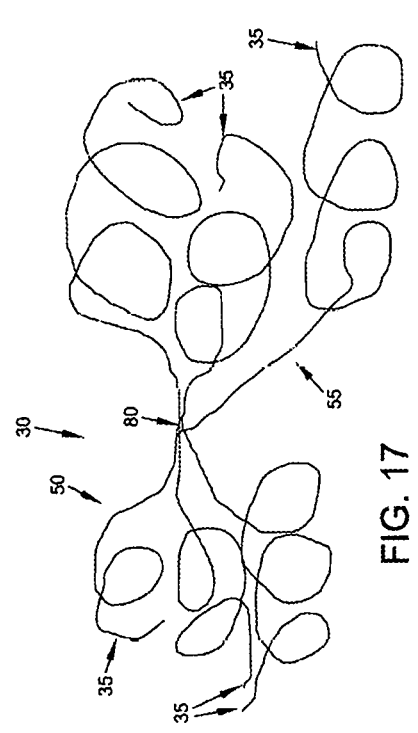

FIG. 17 shows an occluder 30 formed out of multiple strands of elastic filaments 35. In one form of the invention, these multiple strands are joined together at a joinder 80. Again, the coils (e.g., the aforementioned coiled masses 50, 55, 70) formed by these multiple strands can be relatively ordered or relatively disordered. FIGS. 18 and 19 show how the multistrand occluder of FIG. 17 can be used to occlude a vein by forming coiled masses 50, 55 to compress the side wall of the vein inwardly so as to restrict blood flow through the vein. FIG. 20 shows how the multi-strand occluder 30 of FIG. 17 can be used to occlude a vein by depositing a coiled mass 55 within the lumen 60 of the vein, whereby to restrict blood flow through the lumen of the vein. In FIG. 20, a number of the elastic filaments 35 are shown piercing the side wall of the vein so as to hold the coiled mass 55 in position within the lumen of the blood vessel.

FIGS. 21-24 show another form of occluder 30 where the occluder is formed by structures other than a filament. By way of example but not limitation, the occluder 30 may comprise a transluminal section 85, a far side lateral projection 90 and a near side lateral projection 95, with the far side lateral projection 90 and the near side lateral projection 95 being held in opposition to one another so as to close down the lumen 60 of the vein 15. Such an arrangement may be provided by many different types of structures, e.g., such as the "double T-bar" structure shown in FIGS. 25-27 where the transluminal section 85 of the occluder 30 is formed out of an elastic material which draws the two opposing T-bars 90, 95 of the occluder together so as to provide vessel occlusion. Still other arrangements for connecting and drawing together a far side lateral projection 90 and a near side lateral projection 95 will be apparent to those skilled in the art in view of the present disclosure. By way of further example but not limitation, far side lateral projection 90 and near side lateral projection 95 may be connected together by a loop of suture, with the loop of suture being lockable in a reduced size configuration (i.e., so as to maintain occlusion) with a sliding locking knot.

Furthermore, multiple occluders 30 may be used on a single blood vessel or tissue to occlude the blood vessel more completely, or to occlude a blood vessel in multiple regions, or to attach a material (e.g., a drug or cellular delivery element) in multiple places to the blood vessel. The occluders may be coated with a drug-eluting compound, or the occluders may be electrically charged to enhance or prevent clotting or to deliver a desired compound or agent to the blood vessel, etc. If desired, the location of the occluding or attachment element may be precisely controlled to deliver the desired compound or agent at a specific anatomical location.

Endoluminal Approach

In the endoluminal approach, the occluder 30 is delivered to the occlusion site by endoluminally advancing the occluder up the vein using a catheter, and then deploying the occluder in the vein, with the occluder acting to occlude the vein and thereby treat varicose veins. In this form of the invention, the occluder is preferably passed through one or more side walls of the vein so as to stabilize the occluder relative to the vein. In one form of the invention, the occluder is configured to occlude the vein by depositing a mass within the lumen of the vein so as to restrict blood flow through the lumen of the vein; and in another form of the invention, the occluder is configured to occlude the vein by compressing the vein and closing down its lumen.

Figure 29:
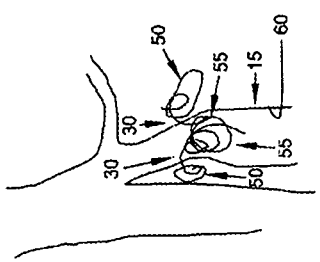
FIGS. 28 and 29 are schematic views showing an occluder occluding a blood vessel in accordance with yet another form of the present invention.
Figure 28:
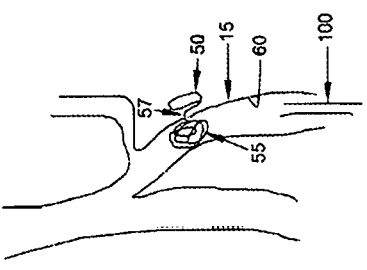

More particularly, and looking now at FIGS. 28 and 29, a catheter 100 is used to endoluminally advance the occluder 30 up the interior of the vein 15 to a deployment site. Then one end of the occluder is passed through the side wall of the vein so as to deposit a coiled mass 50 of the occluder 30 outside the vein, and the remainder of the occluder is deposited as a coiled mass 55 within the lumen 60 of the vein, with a portion 57 of the occluder extending through the side wall of the vein so as to attach the occluder to the side wall of the vein and thereby stabilize the occluder relative to the vein. Thus, in this form of the invention, a coiled mass 55 of the occluder is deposited within the interior of the vein so as to restrict blood flow through the vein and thereby treat varicose veins.

Figure 31:
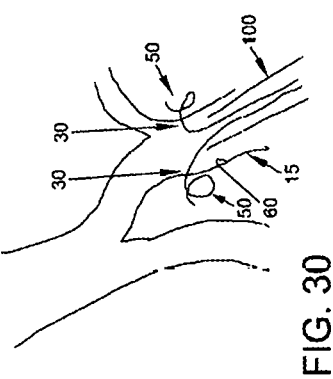
FIGS. 30 and 31 are schematic views showing an occluder occluding a blood vessel in accordance with another form of the present invention.
Figure 30:
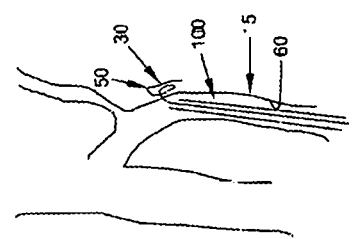

FIGS. 30 and 31 show how two separate occluders 30, each used in the manner shown in FIGS. 28 and 29, can be used to increase the coiled mass of occluder contained within the lumen of the vein, whereby to increase the extent of occlusion of the lumen of the vein.

Figure 33:
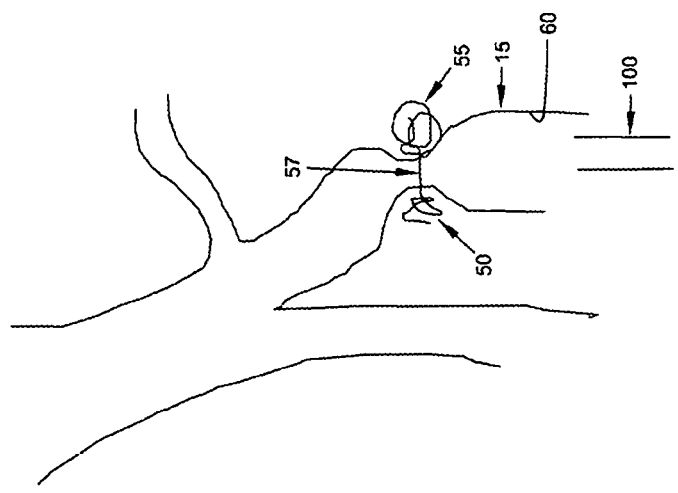
FIGS. 32 and 33 are schematic views showing an occluder occluding a blood vessel in accordance with still another form of the present invention.
Figure 32:
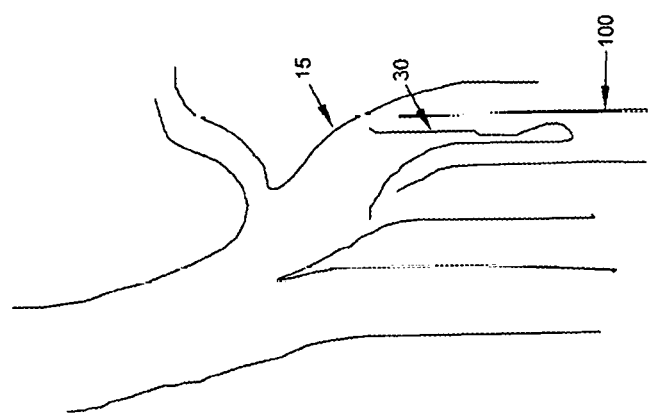

FIGS. 32 and 33 show how an occluder 30 can be delivered endoluminally and used to compress the outer walls of the vein so as to occlude blood flow through the lumen of the vein. More particularly, in this form of the invention, the occluder 30 is advanced endoluminally through the vein to the deployment site, one end of the occluder is passed through one side wall of the vein so as to deposit a coiled mass 50 on one side of the vein and the other end of the occluder is passed through the other side wall of the vein so as to deposit another coiled mass 55 on the other side of the vein, with the two coiled masses being connected together by the intermediate portion 57 of the occluder and with the two coiled masses being drawn toward one another under the coiling force inherent in the elastic filament so as to apply compressive opposing forces on the two sides of the vein, whereby to compress the vein and close down its lumen.

Occlusion in Combination with Phlebectomy

If desired, the novel occluder of the present invention can be used in conjunction with the removal of the large varicose veins (i.e., phlebectomy). The phlebectomy can be done at the same time as the occlusion of the vein or at another time. For this surgical procedure, minimal local anesthetic is needed.

Occluding Tubular Structures for Purposes Other than Treating Varicose Veins

It will be appreciated that the novel occluder of the present invention can also be used to occlude tubular structures for purposes other than treating varicose veins. By way of example but not limitation, the novel occluder of the present invention can be used to occlude other vascular structures (e.g., to occlude arteries so as to control bleeding), or to occlude other tubular structures within the body (e.g., phallopian tubes, so as to induce infertility), etc.

Drug/Cellular Delivery Applications

Furthermore, using the foregoing concept of minimally-invasive hollow tube penetration, and attachment and fixation of the device to the vessel wall, either percutaneously or endoluminally, the occluder 30 may be modified so as to allow drug/cellular delivery at fixed points within or adjacent to the vasculature or other hollow bodily structure. In this form of the invention, the device functions as a drug/cellular delivery stabilizer, and may or may not function as an occluder. See, for example, FIGS. 34 and 35, where an elastic filament 35, having a drug/cellular delivery body 105 attached thereto, is advanced across a blood vessel 110 using a needle 115, with the distal end of the elastic filament forming a coiled mass 120 on the far side of the blood vessel and the drug/cellular delivery body 105 being securely disposed within the lumen 125 of the blood vessel. FIGS. 36 and 37 show a similar arrangement where a catheter 130 is used to deliver the device endoluminally. FIGS. 38 and 39 show another arrangement wherein the device is delivered percutaneously so that the coiled mass is disposed inside lumen 125 of the blood vessel and the drug/cellular delivery body 105 is disposed outside the blood vessel, and FIGS. 40 and 41 show how the device is delivered endoluminally so that the coiled mass is disposed inside lumen 125 of the blood vessel and the drug/cellular delivery body 105 is disposed outside the blood vessel. These drug/cellular delivery devices may be passive or active polymers or silicon-based or micro- and nanotechnology devices, or matrices of materials, etc.

Two-Part Occluder

Figure 42:
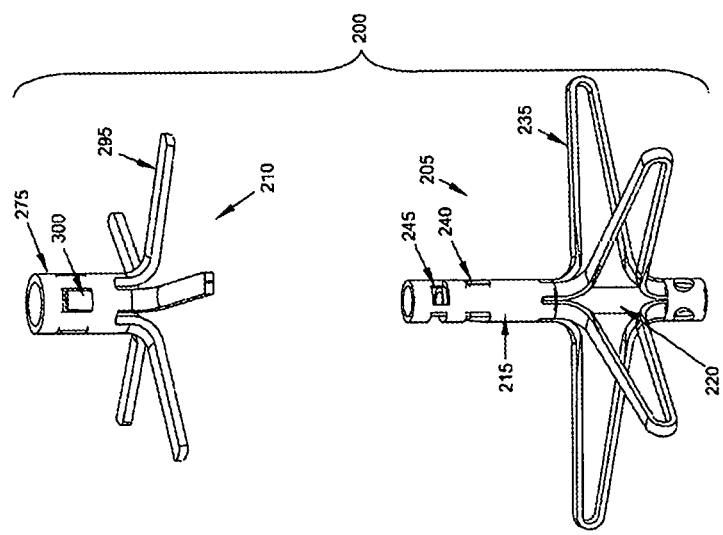

Looking next at FIG. 42, there is shown a two-part occluder 200 formed in accordance with the present invention. Two-part occluder 200 generally comprises a distal implant 205 and a proximal implant 210.

Distal implant 205 is shown in further detail in FIGS. 43-46. Distal implant 205 comprises a distal implant body 215 and a distal implant locking tube 220. Distal implant body 215 comprises a tube 225 having a distal end 226, a proximal end 227, and a lumen 230 extending therebetween. Tube 225 is slit intermediate its length so as to define a plurality of legs 235. A set of inwardly-projecting tangs 240 are formed in tube 225 between legs 235 and proximal end 227. A set of windows 245 are formed in tube 225 between inwardly-projecting tangs 240 and proximal end 227. Distal implant body 215 is preferably formed out of an elastic material (e.g., a shape memory material having superelastic properties such as Nitinol or superelastic polymers, including superelastic plastics) and constructed so that its legs 235 normally project laterally away from the longitudinal axis of tube 225 (e.g., in the manner shown in FIGS. 43 and 44), however, due to the elastic nature of the material used to form distal implant body 215, legs 235 can be constrained inwardly (e.g., within the lumen of a delivery needle, as will hereinafter be discussed) so that distal implant body 215 can assume a substantially linear disposition. See, for example, FIG. 46, which shows legs 235 moved inwardly relative to the position shown in FIGS. 43 and 44. However, when any such constraint is removed, the elastic nature of the material used to form distal implant body 215 causes legs 235 to return to the position shown in FIGS. 43 and 44.

Distal implant locking tube 220 (FIG. 45) comprises a generally tubular structure having a distal end 250, a proximal end 260 and a lumen 262 extending therebetween. A set of windows 265 are formed in the distal implant locking tube 220, with windows 265 being disposed distal to proximal end 260.

Distal implant locking tube 220 is disposed within lumen 230 of distal implant body 215. When distal implant 205 is in its aforementioned substantially linear condition (i.e., with legs 235 restrained in an in-line condition), distal implant locking tube 220 terminates well short of tangs 240 of distal implant body 215, so that the proximal end 227 of distal implant body 215 can move longitudinally relative to distal end 226 of distal implant body 215. However, when the proximal end 227 of distal implant body 215 is moved distally a sufficient distance to allow full radial expansion of legs 235 (see FIG. 42), locking tangs 240 of distal implant body 215 will be received within windows 265 of distal implant locking tube 220, whereby to lock distal implant 205 in its radially-expanded condition (i.e., with legs 235 projecting laterally away from the longitudinal axis of tube 225, e.g., in the manner shown in FIGS. 43 and 44). Spot welds applied via openings 270 formed in the distal end 226 of distal implant body 215 serve to lock distal implant locking tube 220 to distal implant body 215, whereby to form a singular structure (see FIGS. 43 and 46).

Looking next at FIGS. 47 and 48, proximal implant 210 comprises a tube 275 having a distal end 280, a proximal end 285, and a lumen 290 extending therebetween. Tube 275 is slit at its distal end so as to define a plurality of legs 295. A set of inwardly-projecting tangs 300 are formed in tube 275 between legs 295 and proximal end 285. Proximal implant 210 is preferably formed out of an elastic material (e.g., a shape memory material having superelastic properties such as Nitinol) and constructed so that its legs 295 normally project laterally away from the longitudinal axis of tube 275 (e.g., in the manner shown in FIG. 47), however, legs 295 can be constrained inwardly (e.g., within the lumen of a delivery tube, as will hereinafter be discussed) so that proximal implant 210 can assume a substantially linear disposition. See, for example, FIG. 48, which shows legs 295 moved inwardly relative to the position shown in FIG. 47. However, when any such constraint is removed, the elastic nature of the material used to form proximal implant 210 causes legs 295 to return to the position shown in FIG. 47.

As will hereinafter be discussed, distal implant 205 and proximal implant 210 are configured and sized so that tube 225 of distal implant body 215 can be received in lumen 290 of proximal implant 210, with the expanded legs 235 of distal implant 205 opposing the expanded legs 295 of proximal implant 210 (see, for example, FIG. 82), whereby to impose a clamping action on the side wall of a blood vessel (e.g., vein) disposed therebetween and thereby occlude the blood vessel, as will hereinafter be discussed in further detail (or, as an alternative, the opposing expanded legs of the proximal and distal implants could interdigitate to impose the clamping action). Furthermore, distal implant 205 and proximal implant 210 are configured and sized so that they may be locked in this position, inasmuch as inwardly-projecting tangs 300 of proximal implant 210 will project into windows 245 of distal implant 205.

Figure 50:
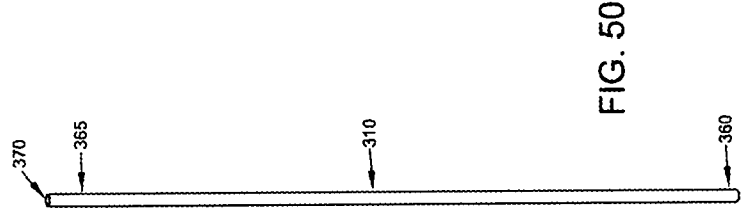
FIGS. 49-58 are schematic views showing installation apparatus which may be used to deploy the two-part occluder of FIGS. 42-48.
Figure 49:
Figures 53, 54:
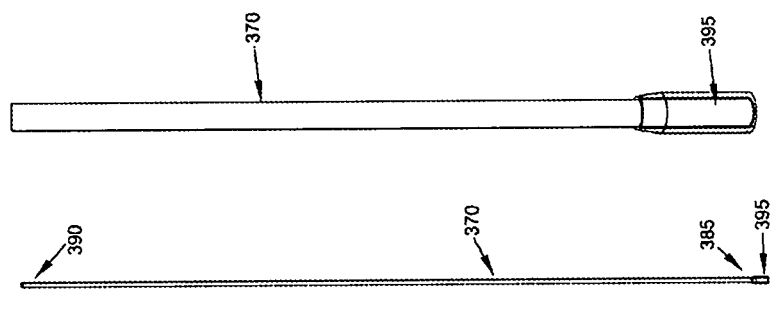
Figure 52:
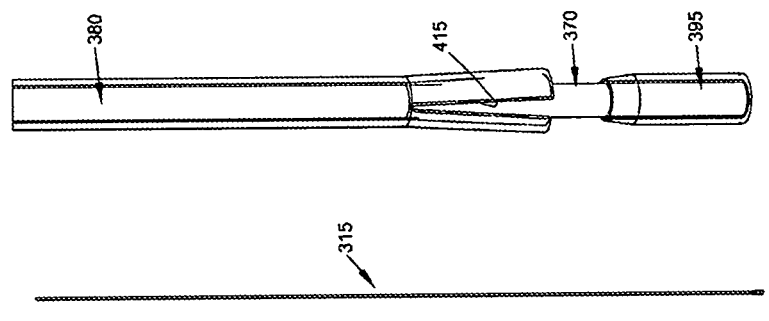
Figure 51:
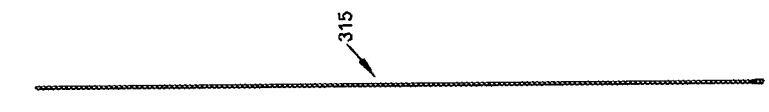
Figure 58:
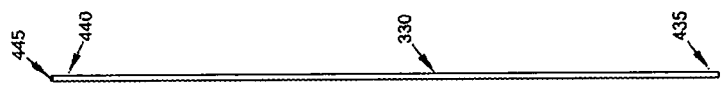
Figure 57:
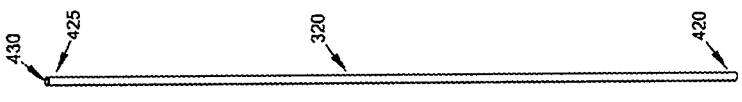
Figure 56:
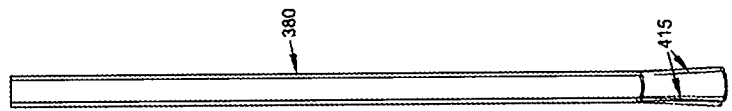
Figure 55:
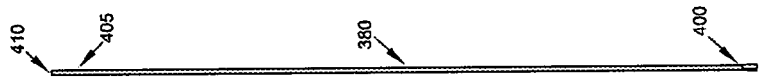

Two-part occluder 200 is intended to be deployed using associated installation apparatus. This associated installation apparatus preferably comprises a hollow needle 305 (FIG. 49) for penetrating tissue, a distal implant delivery tube 310 (FIG. 50) for delivering distal implant 205 through hollow needle 305 to the far side of the blood vessel which is to be occluded, a composite guidewire 315 (FIGS. 51-56) for supplying support to various components during delivery and deployment, a push rod 320 (FIG. 57) for delivering various components over composite guidewire 315, and a proximal implant delivery tube 330 (FIG. 58) for delivering proximal implant 210 for mating with distal implant 205, as will hereinafter be discussed.

Hollow needle 305 (FIG. 49) comprises a distal end 335, a proximal end 340 and a lumen 345 extending therebetween. Distal end 335 terminates in a sharp point 350. In one preferred form of the invention, hollow needle 305 comprises a side port 355 which communicates with lumen 345.

Distal implant delivery tube 310 (FIG. 50) comprises a distal end 360, a proximal end 365 and a lumen 370 extending therebetween.

Composite guidewire 315 (FIGS. 51-56) comprises a guidewire rod 370 and a guidewire sheath 380. Guidewire rod 370 comprises a distal end 385 and a proximal end 390. Distal end 385 terminates in an enlargement 395. Guidewire sheath 380 comprises a distal end 400, a proximal end 405 and a lumen 410 extending therebetween. The distal end 400 of guidewire sheath 380 comprises at least one, and preferably a plurality of, proximally-extending slits 415. Proximally-extending slits 415 open on the distal end of guidewire sheath 380 and allow the distal end of guidewire sheath 380 to radially expand somewhat. As will hereinafter be discussed, guidewire rod 370 and guidewire sheath 380 are configured and sized so that guidewire rod 370 can be received in lumen 410 of guidewire sheath 380.

Furthermore, when guidewire rod 370 is forced proximally relative to guidewire sheath 380, the proximally-extending slits 415 in guidewire sheath 380 allow the distal end of the guidewire sheath 380 to expand somewhat so as to receive at least some of the enlargement 395 formed on the distal end of guidewire rod 370. As this occurs, the distal end of guidewire sheath 380 will expand radially.

Push rod 320 (FIG. 57) comprises a distal end 420, a proximal end 425 and a lumen 430 extending therebetween.

Proximal implant delivery tube 330 (FIG. 58) comprises a distal end 435, a proximal end 440 and a lumen 445 extending therebetween.

Two-part occluder 200 and its associated installation apparatus are preferably used as follows.

Figure 61:
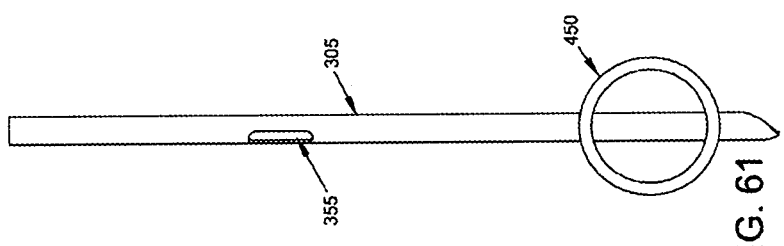
Figure 60:
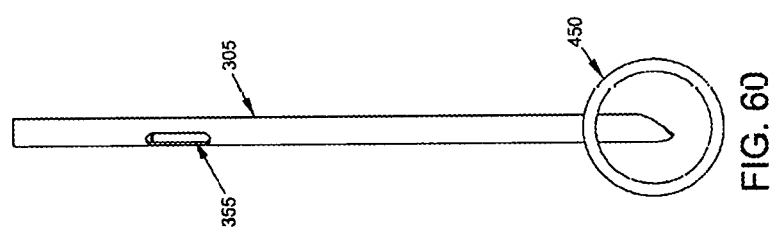
Figure 59:
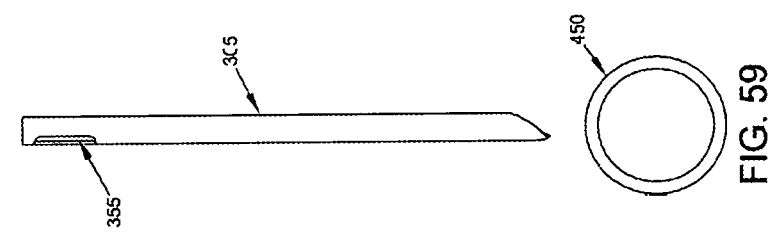

First, hollow needle 305 (carrying distal implant delivery tube 310 therein, which in turn contains the composite guidewire 315 therein, upon which is mounted distal implant 205) is passed through the skin of the patient, through intervening tissue, and across the blood vessel (e.g., vein 450) which is to be occluded. See FIGS. 59-61. As this is done, any blood flowing out side port 355 can be monitored—excessive or pulsatile blood flow can indicate that hollow needle has accidentally struck an artery.

Next, hollow needle 305 is retracted, leaving distal implant delivery tube 310 extending across the blood vessel. See FIG. 62.

Then distal implant delivery tube 310 is retracted somewhat so as to expose the distal ends of composite guidewire, or rod, 315 and distal implant 205. See FIG. 63.

Figure 65:
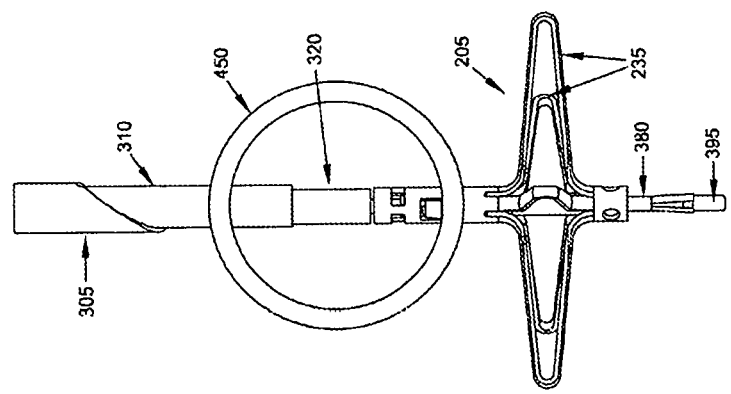

Next, composite guidewire 315, push rod 320 and distal implant 205 are all moved distally, so as to advance the distal ends of composite guidewire 315 and the distal implant 205 out of the distal end of distal implant delivery tube 310. As this occurs, legs 235 of distal implant 205 are released from the constraint of distal implant delivery tube 310 and expand radially. See FIGS. 64 and 65.

Figure 66:
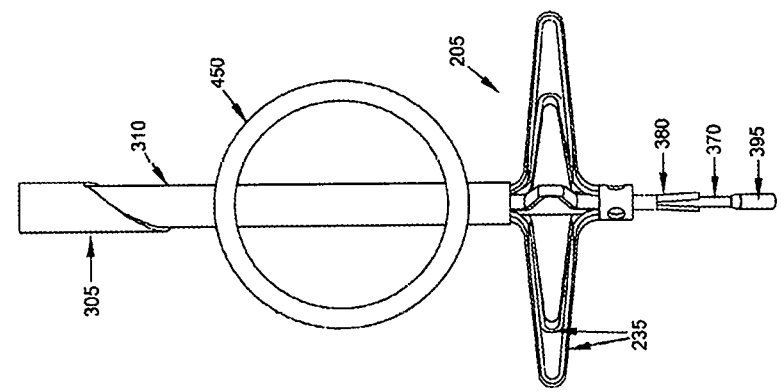
Figure 70:
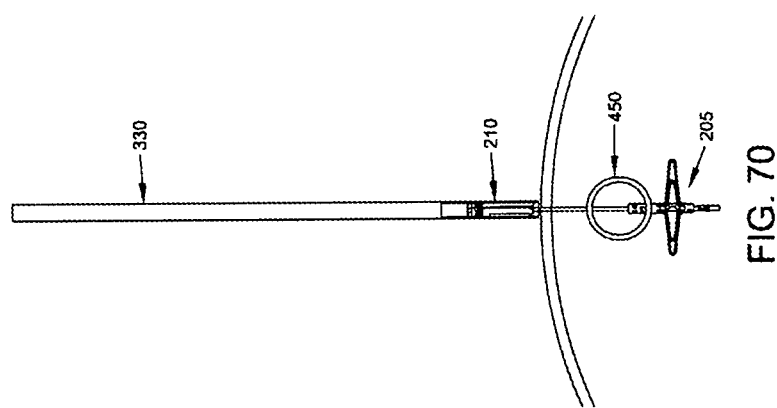
Figure 69:
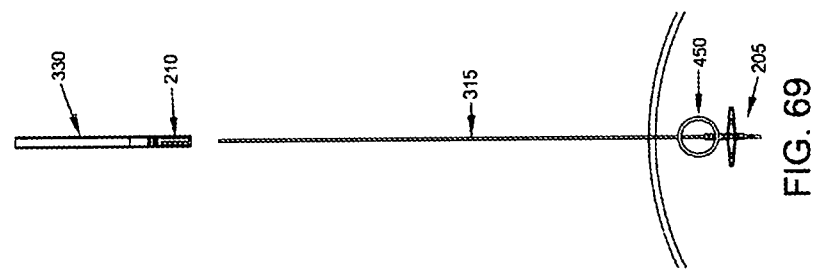
Figure 74:
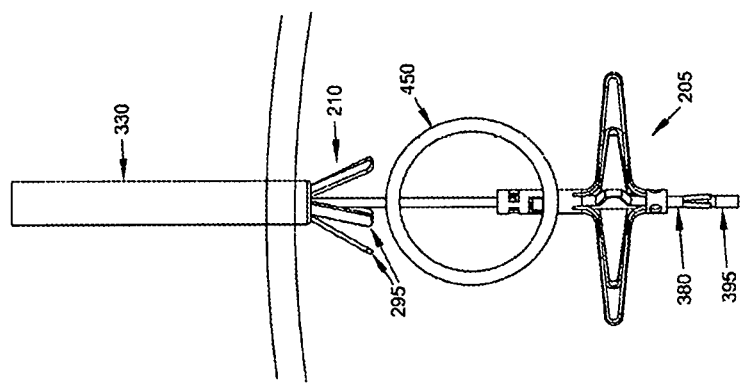
Figure 73:
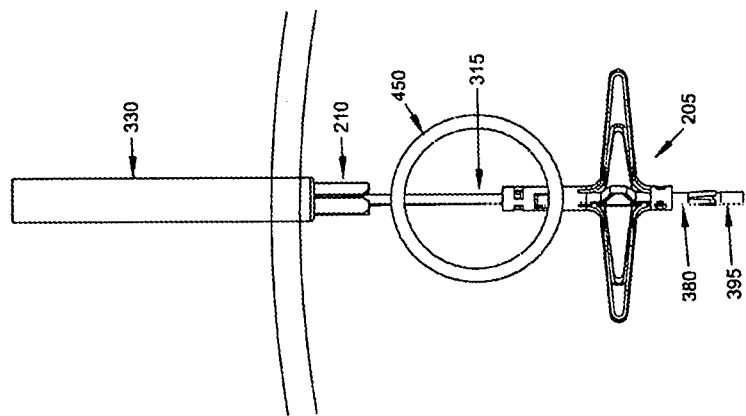

Then, with push rod 320 being held in place against the proximal end of distal implant 205, composite guidewire 315 is pulled proximally so as to bring the distal end of distal implant 205 toward the proximal end of distal implant 205, whereby to cause locking tangs 240 of distal implant body 215 to enter windows 265 of distal implant locking tube 220, whereby to lock legs 235 in their radially-expanded condition (see FIG. 66).

At this point, hollow needle 305, distal implant delivery tube 310 and push rod 320 may be removed (FIG. 67), leaving distal implant 205 mounted on composite guidewire 315, with the legs 235 fully deployed on the far side of the blood vessel and the proximal end of distal implant 205 extending into the interior of the blood vessel (FIG. 68).

Next, proximal implant delivery tube 330 (carrying proximal implant 210 therein) is advanced down composite guidewire 315, until the distal end of proximal implant delivery tube 330 sits just proximal to the blood vessel (FIGS. 69-72).

Then push rod 320 is used to advance the distal end of proximal implant 210 out of the distal end of proximal implant delivery tube 330. As this occurs, legs 295 are released from the constraint of proximal implant delivery tube 330 and open radially. See FIGS. 73-76.

Next, using push rod 320, proximal implant 210 is pushed distally as distal implant 205 is pulled proximally using composite guidewire 315. More particularly, guidewire rod 370 is pulled proximally, which causes enlargement 395 on the distal end of guidewire rod 370 to expand guidewire sheath 380 to a size larger than lumen 262 in distal implant locking tube 220, which causes guidewire sheath 380 to move proximally, which causes proximal movement of distal implant 205. As distal implant 205 and proximal implant 210 move together, their legs 235, 295 compress the blood vessel, thereby occluding the blood vessel. Distal implant 205 and proximal implant 210 continue moving together until inwardly-projecting tangs 300 of proximal implant 210 enter windows 245 of distal implant 205, thereby locking the two members into position relative to one another. See FIG. 77.

At this point push rod 320 and proximal implant delivery tube 330 are removed. See FIG. 78.

Figure 80:
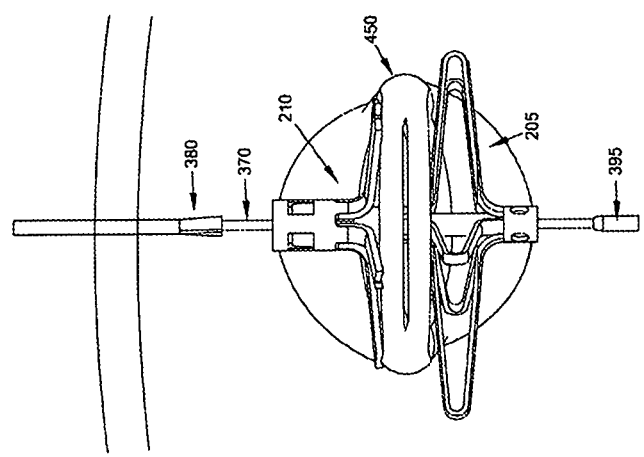
Figure 79:
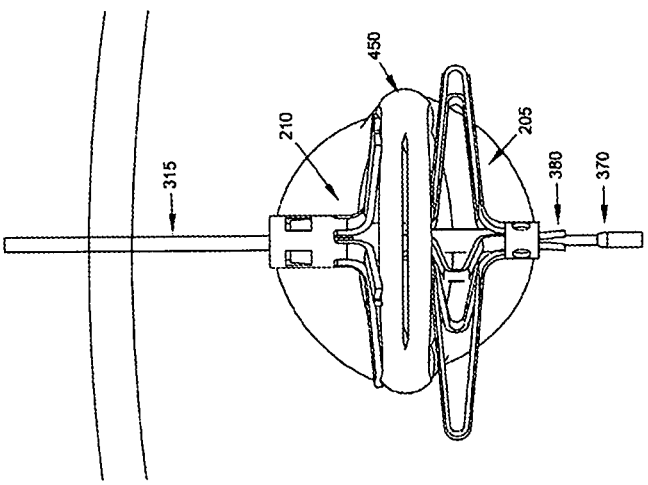
Figure 84:
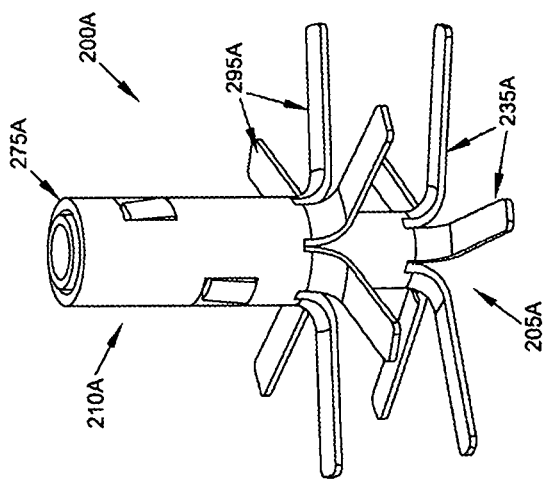
FIGS. 83-86 are schematic views showing another two-part occluder formed in accordance with the present invention.
Figure 83:
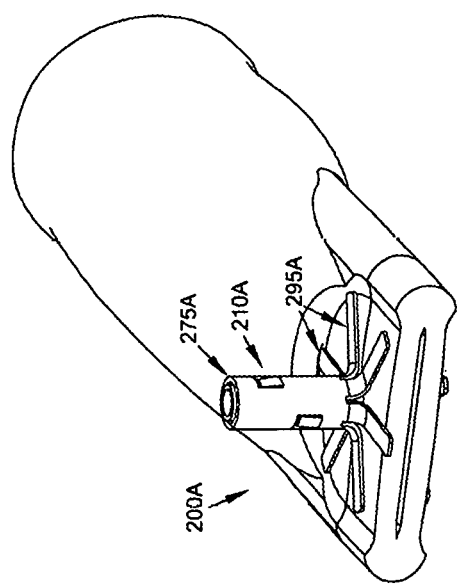
Figure 86:
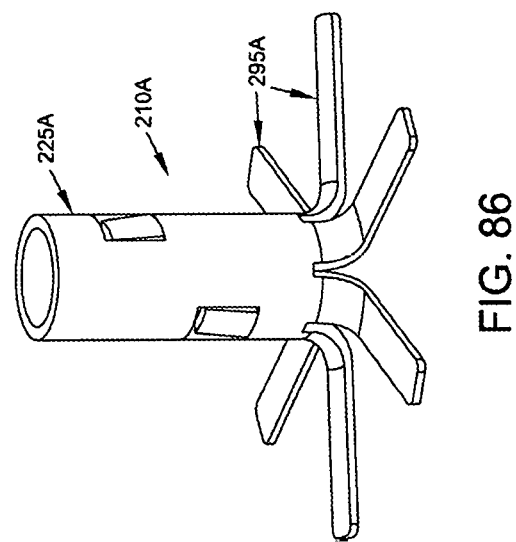
Figure 85:
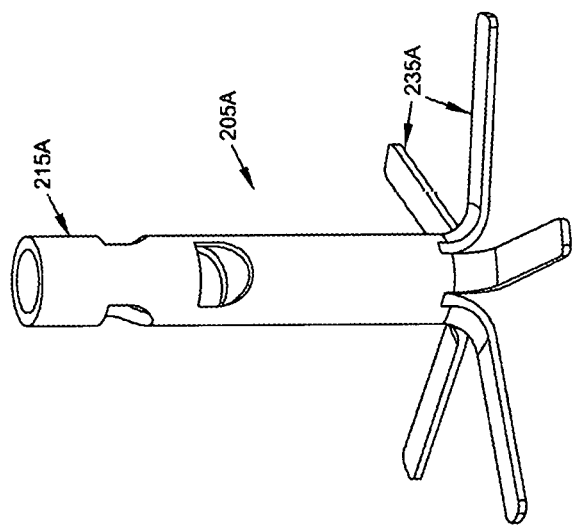
Figure 88:
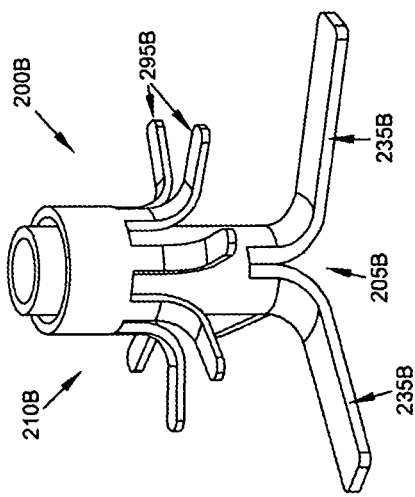
FIGS. 87-90 are schematic views showing still another two-part occluder formed in accordance with the present invention.
Figure 87:
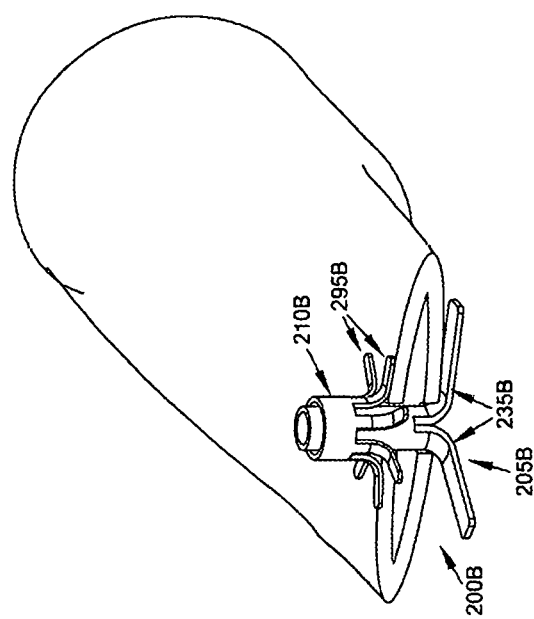
Figure 90:
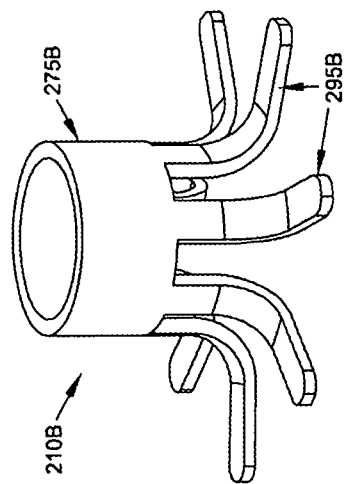
Figure 89:
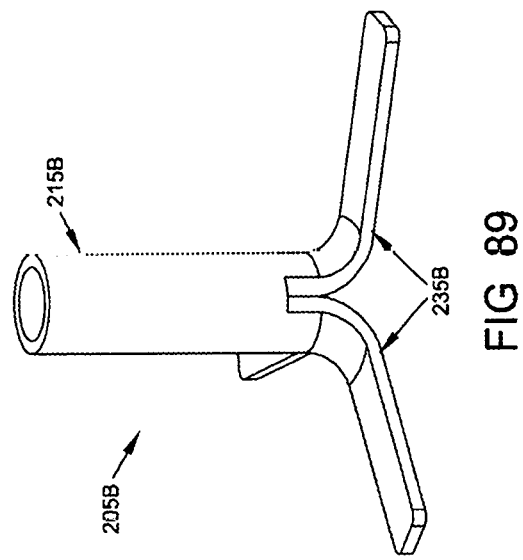
Figure 97:
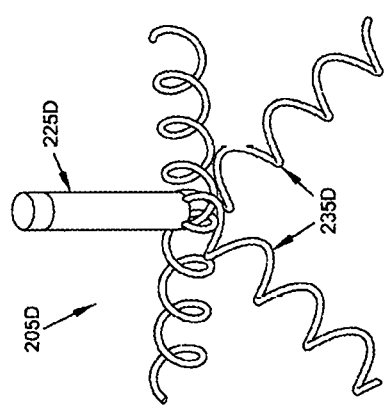
Figure 98:
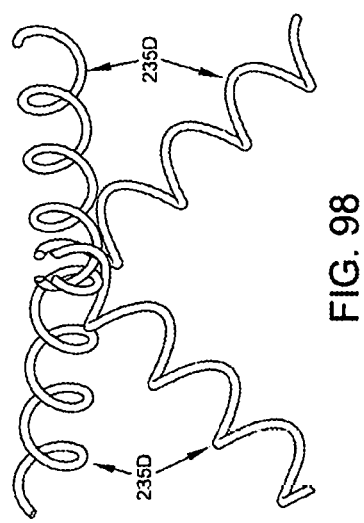
Figure 100:
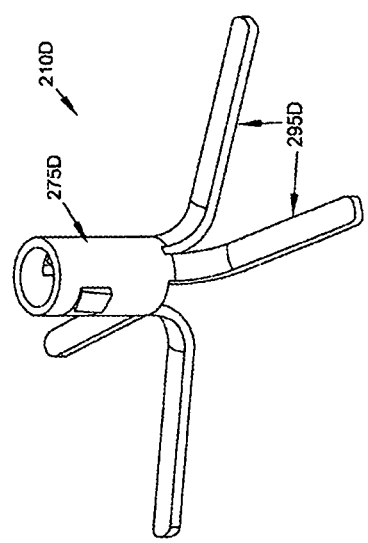
Figure 99:
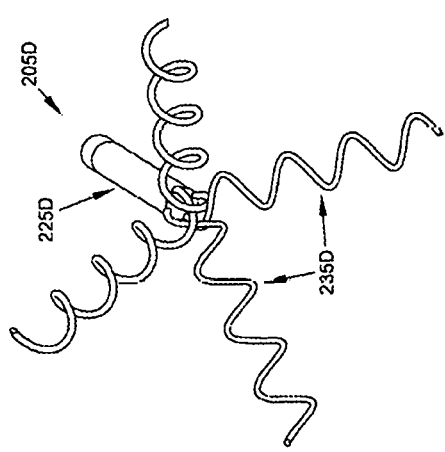

Next, composite guidewire 315 is removed. This is done by first advancing guidewire rod 370 distally (FIG. 79), which allows the distal end of guidewire sheath 380 to relax inwardly, thereby reducing its outer diameter to a size smaller than lumen 262 in distal implant locking tube 220. As a result, guidewire sheath 380 can then be withdrawn proximally through the interior of two-part occluder 200. See FIG. 80. Then guidewire rod 370 can be withdrawn proximally through the interior of two-part occluder 200. See FIG. 81.

The foregoing procedure leaves two-part occluder 200 locked in position across the blood vessel, with the opposing legs 235, 295 compressing the blood vessel, whereby to occlude the blood vessel.

FIGS. 83-86 illustrate another two-part occluder 200A having a distal implant 205A and a proximal implant 210A. Two-part occluder 200A is generally similar to the aforementioned two-part occluder 200, except that distal implant 205A utilizes a unibody construction.

FIGS. 87-90 illustrate another two-part occluder 200B. Two-part occluder 200B is generally similar to the aforementioned two-part occluder 200A, except that distal implant 205B utilizes a friction fit to lock distal implant 205B to proximal implant 210B.

FIGS. 91-94 illustrate another two-part occluder 200C having a distal implant 205C and a proximal implant 210C. Two-part occluder 200C is generally similar to the aforementioned two-part occluder 200, except that distal implant 205C comprises a tube 225C which receives and secures the proximal ends of legs 235C. Legs 235C are preferably elongated elements (e.g., bent wires) formed out of a superelastic shape memory material so as to provide the legs 235C with the desired degree of elasticity.

FIGS. 95-100 illustrate another two-part occluder 200D having a distal implant 205D and a proximal implant 210D. Two-part occluder 200D is generally similar to the aforementioned two-part occluder 200, except that distal implant 205D comprises a tube or rod 225D which receives and secures the proximal ends of legs 235D. Legs 235D are preferably coils formed out of a superelastic shape memory material so as to provide the legs 235D with the desired degree of elasticity.

In the foregoing disclosure, there is a disclosed a composite guidewire 315 for use in delivering distal implant 205 and proximal implant 210 to the anatomy. As noted above, composite guidewire 315 is formed from two parts, i.e., a guidewire rod 370 and a guidewire sheath 380. By providing composite guidewire 315 with this two-part construction, composite guidewire 315 can have its distal diameter enlarged or reduced as desired so as to permit composite guidewire 315 to bind to distal implant 205, or be separable from the distal implant 205, respectively. However, if desired, composite guidewire 315 can be replaced by an alternative guidewire which includes a mechanism for releasably binding the alternative guidewire to distal implant 205. By way of example but not limitation, such an alternative guidewire may include screw threads, and distal implant 205 may include a screw recess, so that the alternative guidewire can be selectively secured to, or released from, the distal implant 205, i.e., by a screwing action.

Looking next at FIGS. 101-104, there is shown a two-part occluder 200E formed in accordance with the present invention. Two-part occluder 200E generally comprises a distal implant 205E and a proximal implant 210E.

Distal implant 205E comprises a distal implant body 215E and a distal implant locking tube 220E. Distal implant body 215E comprises a tube 225E having a distal end and an opposing proximal end. Preferably distal implant 205E has a lumen 230E extending distally from its proximal end. Lumen 230E may extend along the entire length of distal implant body 215E or it may terminate short of the distal end of distal Implant body 215E, By way of example but not limitation, where two-part occluder 200E is to be set over a guidewire, lumen 230E extends along the entire length of distal implant body 215E. Tube 225E is slit intermediate its length so as to define a plurality of legs 235E. Distal implant body 215E is preferably formed at least in part out of an elastic material (e.g., a shape memory material having superelastic properties such as Nitinol or superelastic polymers, including superelastic plastics) and is constructed so that its legs 235E normally project laterally away from the longitudinal axis of tube 225E (e.g., in the manner shown in FIGS. 101-104), however, due to the elastic nature of the material used to form at least the legs 235E of distal implant body 215E, legs 235E can be constrained inwardly (e.g., within the lumen of a delivery needle, as will hereinafter be discussed) so that distal implant body 215E can assume a substantially linear disposition (in which case the distalmost tips of legs 235E converge to form the aforementioned proximal end of distal implant body 215E). However, when any such constraint is removed (e.g., when distal implant body 215 is no longer constrained within a delivery needle), the elastic nature of the material used to form at least the legs 235E of distal implant body 215E causes legs 235E to assume the position shown in FIGS. 101-404.

Figure 101:
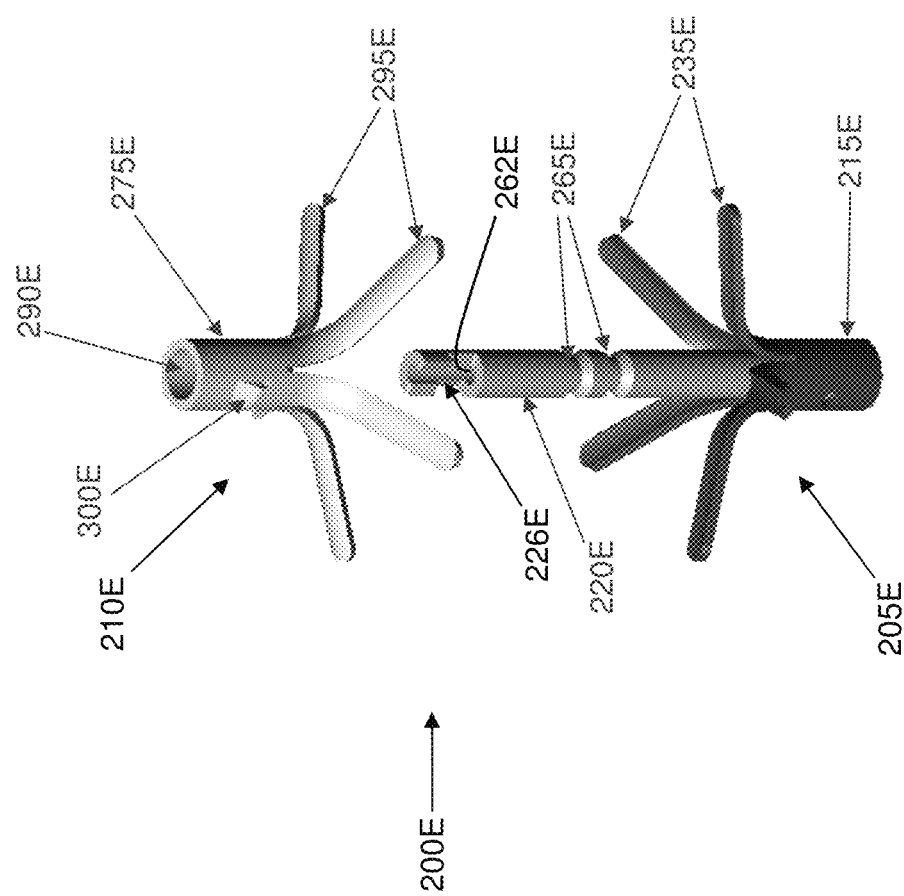
Figure 102:
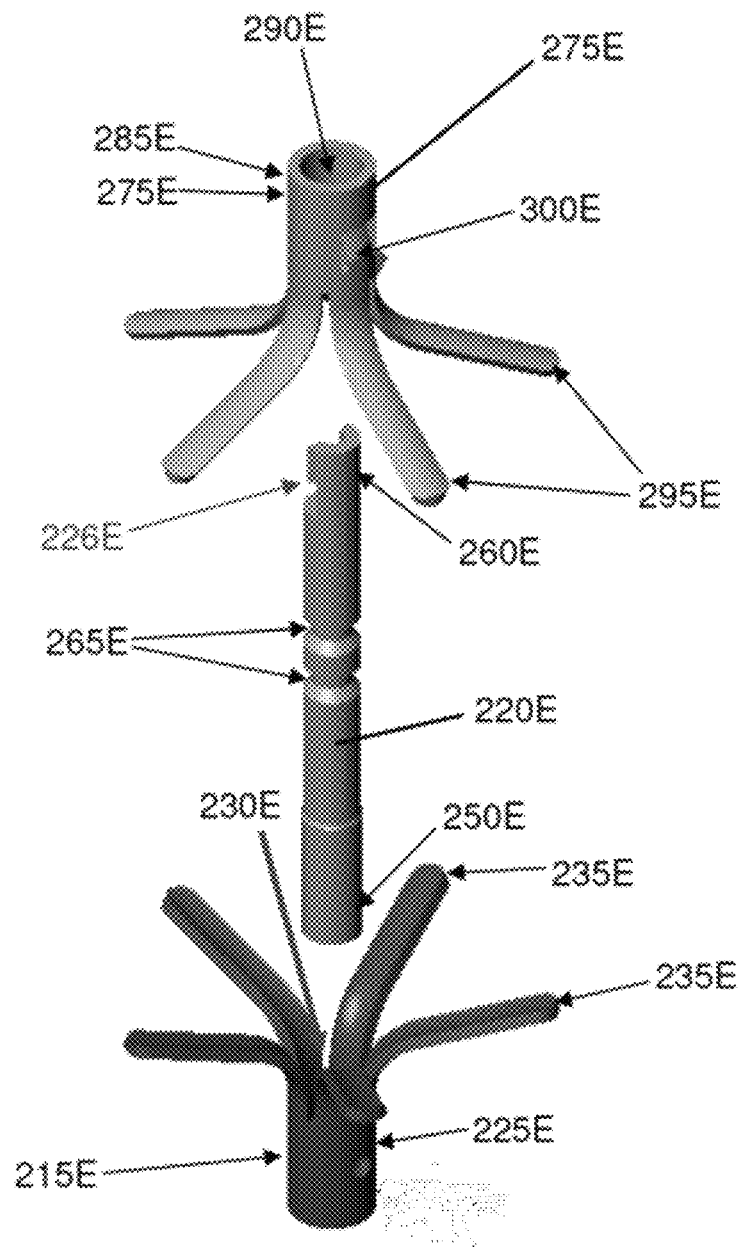
Figure 105:
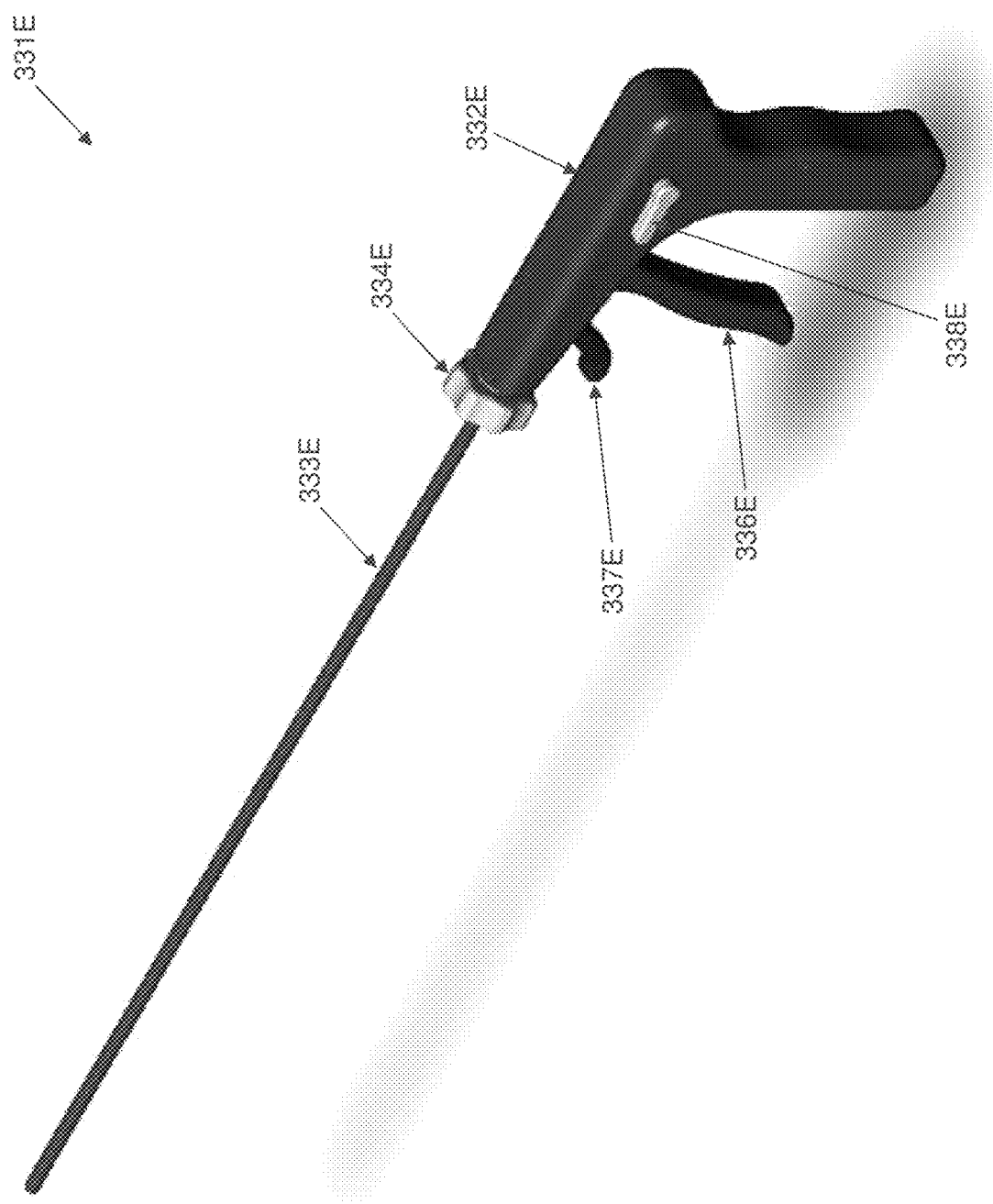
Figure 106:
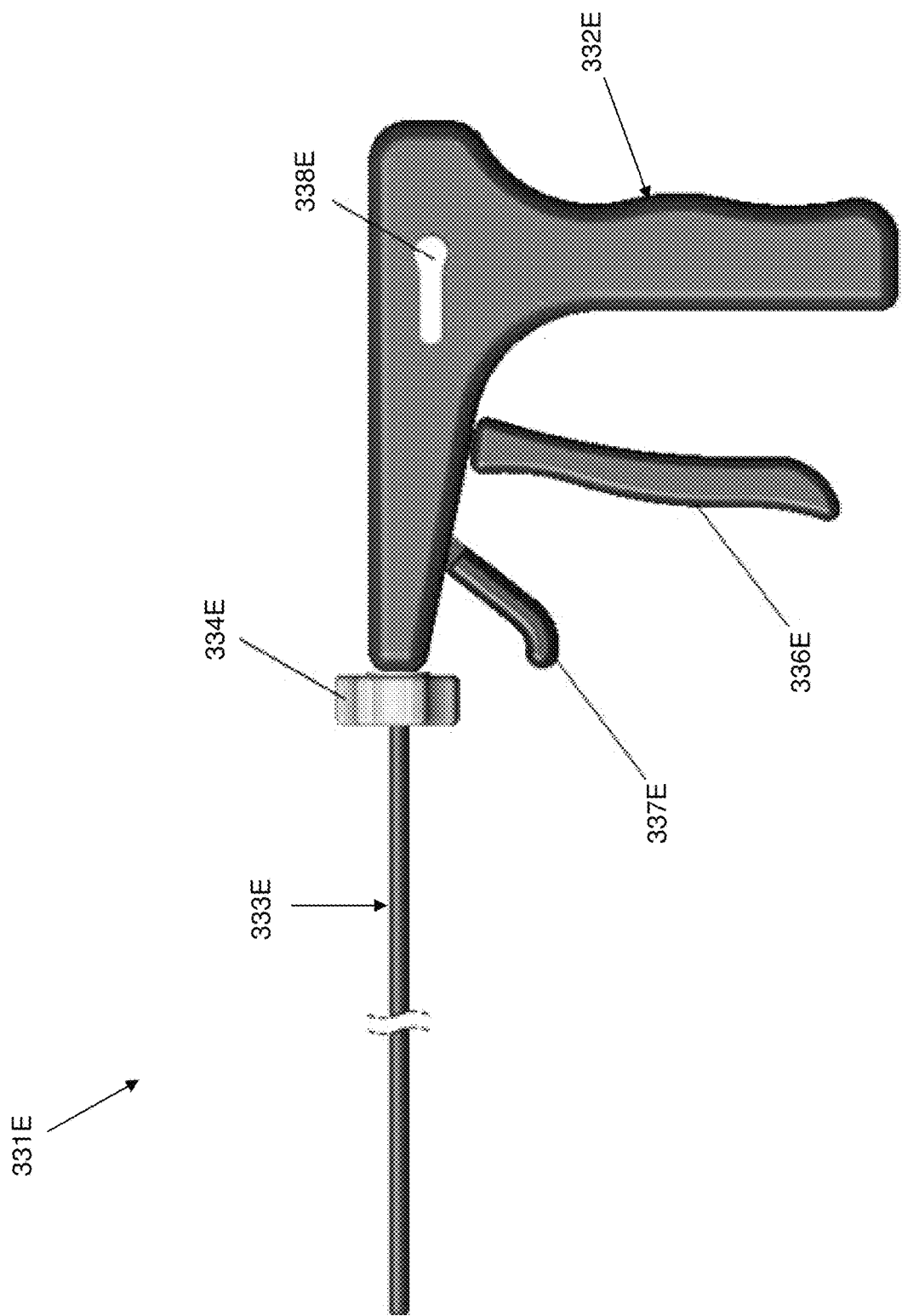
Figure 114:
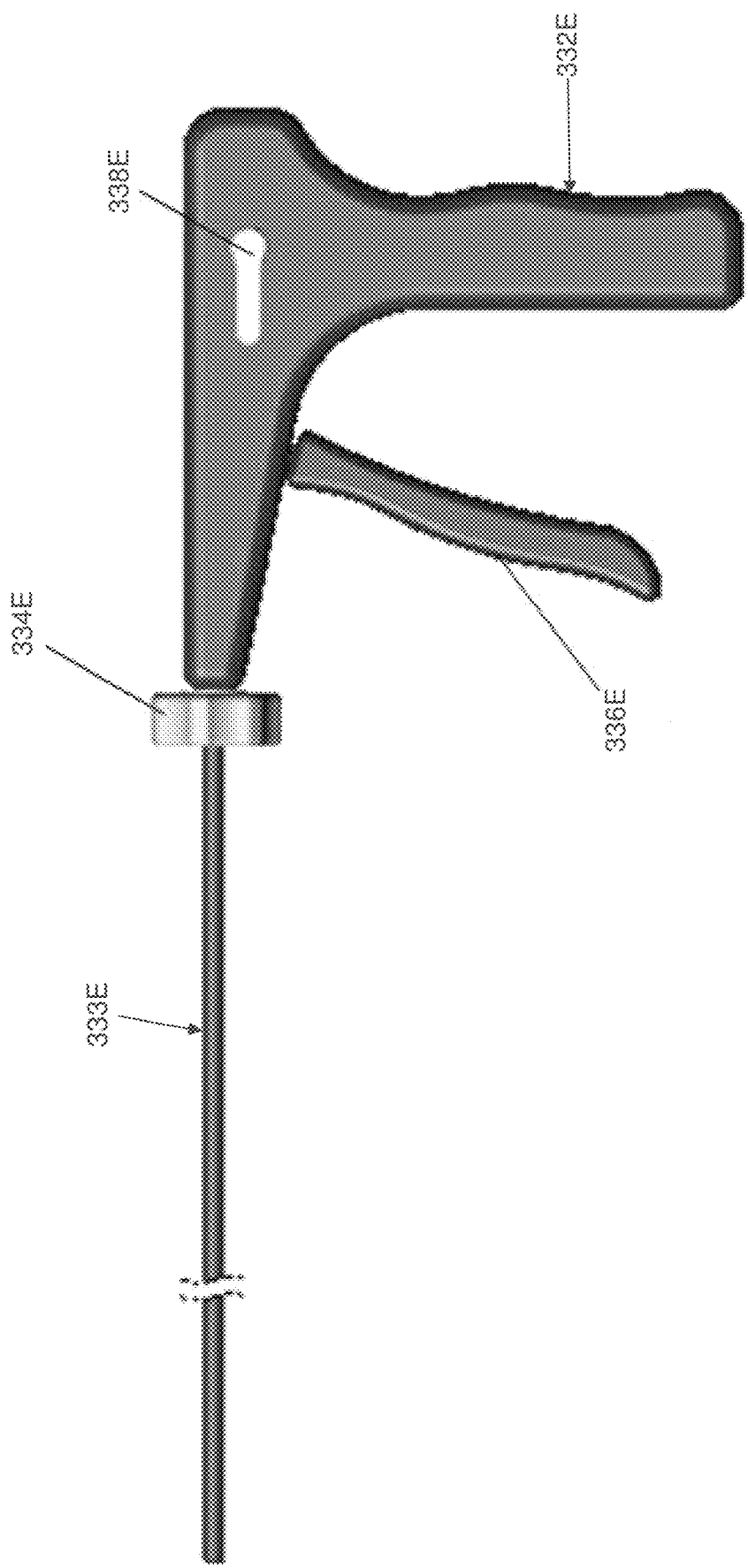

In one preferred form of the invention, and as seen in FIGS. 101-103, legs 235E of distal implant 205E extend at an acute angle to the longitudinal axis of distal implant 205E, such that legs 235E collectively define a concave region 236E.

Distal implant locking tube 220E (FIGS. 101-404) comprises a generally tubular structure having a distal end 250E and a proximal end 260E. Preferably distal implant locking tube 220E has a lumen 262E extending distally from proximal end 260E. Lumen 262E may extend along the entire length of distal implant locking tube 220E or it may terminate short of the distal end of distal implant locking tube 220E. By way of distal implant locking tube 220E has a lumen 262E extending distally from proximal end 260E. Lumen 262E may extend along the entire length of distal implant locking tube 220E or it may terminate short of the distal end of distal implant locking tube 220E, By way of example but not limitation, where two-part occluder 200E is to be set over a guidewire, lumen 262E of distal implant locking tube 220E extends along the entire length of distal implant locking tube 220E. A set of circumferential grooves or recesses 265E are formed in distal implant locking tube 220E, with grooves or recesses 265E being disposed intermediate distal end 250E and proximal end 260E. Distal implant locking tube 220E also comprises a first half 226E of a mechanical interlock for releasably securing distal implant locking tube 220E (and hence distal implant 205E) to a distal implant delivery tube 310E (see below). Distal implant locking tube 220E is preferably formed out of a biocompatible material which is relatively inelastic along its length, whereby to mimic lengthwise stretching, although it may be somewhat flexible, whereby to allow it to be delivered over a curved path. By way of example but not limitation, distal implant locking tube 220E may be formed out of a titanium alloy such as Ti 5 AL-4V.

Distal implant locking tube 220E is disposed within, and extends proximally from, lumen 230E of distal implant body 215E. Distal implant locking tube 220E is secured to distal implant body 215E in ways well known in the art (e.g., by spot welding, adhesives, mechanical interlocks, etc.), whereby to collectively form a singular structure (see FIGS. 101-104). Note that by forming distal implant body 215E out of an elastic material, and by forming distal implant locking tube 220E out of a material which is relatively inelastic along its length, distal implant body 215E is easily deformable (e.g., so that its legs 235E can be constrained within a delivery needle) while distal implant locking tube 220E is fixed in configuration (e.g., so that it can serve to hold proximal implant 210E to distal implant 205E, as will hereinafter be discussed).

Still looking now at FIGS. 101-104, proximal implant 210E comprises a tube 275E having a distal end, a proximal end 285E, and a lumen 290E extending therebetween. Tube 275E is slit at its distal end so as to define a plurality of legs 295E. A set of inwardly-projecting tangs 300E are formed in tube 275E, between legs 295E and proximal end 285E, for engaging the aforementioned grooves or recesses 265E in distal implant locking tube 220E, as will hereinafter be discussed (note that, if desired, the locations and configurations of grooves or recesses 265E and tangs 300E can be reversed, i.e., outwardly-projecting tangs 300E can be provided on distal implant locking tube 220E and grooves or recesses 265E can be provided on the inner side wall of tube 275E, or other means can be provided for connecting tube 275E of proximal implant 210E to distal implant locking tube 220E of distal implant 205E). Proximal implant 210E is preferably formed at least in part out of an elastic material (e.g., a shape memory material having superelastic properties such as Nitinol) and constructed so that its legs 295E normally project laterally away from the longitudinal axis of tube 275E (e.g., in the manner shown in FIGS. 101-104), however, legs 295E can be constrained inwardly (e.g., within the lumen of a delivery needle, as will hereinafter be discussed) so that proximal implant 210E can assume a substantially linear disposition (with the distal ends of legs 295E collectively forming the distal end of proximal implant 210E). However, when any such constraint is removed, the elastic nature of the material used to form at least the legs 295E of proximal implant 210E causes legs 295E to return to the position shown in FIGS. 101-104.

In one preferred form of the invention, and as seen in FIGS. 101-104, legs 295E of proximal implant 210E extend at an obtuse angle to the longitudinal axis of proximal implant 210E, such that legs 295E collectively define a concave region 301E.

Note that the concavity of concave region 236E of distal implant 205E is the reverse of the concavity of concave region 301E of proximal implant 210E (in other words, and as seen in FIGS. 101-104, the concavity of concave region 236E of distal implant 205E faces the concavity of concave region 301E of proximal implant 210E).

As will hereinafter be discussed, distal implant 205E and proximal implant 210E are configured and sized so that distal implant locking tube 220E of distal implant 205E can be received in lumen 290E of proximal implant 210E, with the expanded legs 235E of distal implant 205E opposing the expanded legs 295E of proximal implant 210E (see, for example, FIGS. 103 and 104), whereby to impose a clamping action on the side walls of a blood vessel (e.g., vein) disposed therebetween and thereby occlude the blood vessel, as will hereinafter be discussed in further detail (or, as an alternative, the opposing expanded legs of the proximal and distal implants may interdigitate so as to further enhance the clamping action. Furthermore, distal implant 205E and proximal implant 210E are configured and sized so that they may be locked in this position, inasmuch as inwardly-projecting tangs 300E of proximal implant 210E will project into circumferential grooves or recesses 265E of distal implant locking tube 220E of distal implant 205E, whereby to secure proximal implant 210E to distal implant 205E. Note that the positions of circumferential grooves or recesses 265E of distal implant locking tube 220E and inwardly-projecting tangs 300E of proximal implant 210E are coordinated so that when inwardly-projecting tangs 300E of proximal implant 210E are disposed in circumferential grooves or recesses 265E of distal implant locking tube 220E, legs 235E of distal implant 205E and legs 295E of proximal implant 210E are sufficiently close to ensure adequate clamping of a blood vessel (or other tubular structure) disposed therebetween.

Two-part occluder 200E is intended to be deployed using associated installation apparatus. In one preferred form of the invention, such associated installation apparatus preferably comprises a hollow needle 305E (FIG. 109) for penetrating tissue, a distal implant delivery tube 310E (FIG. 110) for delivering distal implant 205E through hollow needle 305E to the far side of the blood vessel (or other tubular structure) which is to be occluded, and a proximal implant delivery tube 330E (FIG. 110) for delivering proximal implant 210E for mating with distal implant 205E, as will hereinafter be discussed.

If desired, the associated installation apparatus may be provided in the form of a laparoscopic device 331E as shown in FIGS. 105-113. Laparoscopic device 331E comprises a handle 332E, an outer sheath 333E, a knob 334E, a first trigger 336E, a second trigger 337E and a release lever 338E, with the functionality hereinafter described.

More particularly, hollow needle 305E (FIG. 109) comprises a distal end 335E, a proximal end (not shown, but contained within laparoscopic device 331E) and a lumen 345E extending therebetween. Distal end 335E of hollow needle 305E terminates in a sharp point 350E.

Distal implant delivery tube 310E (FIG. 110) comprises a distal end 360E and a proximal end (not shown, but contained within laparoscopic device 331E). Distal end 360E of distal implant delivery tube 310E also comprises a second half 361E of a mechanical interlock for releasably securing the distal end of distal implant delivery tube 310E to the proximal end of distal implant 205E, i.e., by the releasable interconnection of the first half 266E of the mechanical interlock (carried by the proximal end of distal implant locking tube 220E) with the second half 361E of the mechanical interlock (carried by the distal end of distal implant delivery tube 310E).

Proximal implant delivery tube 330E (FIG. 110) comprises a distal end 435E, a proximal end (not shown, but contained within laparoscopic device 331E) and a lumen 445E extending therebetween.

Two-part occluder 200E and its associated installation apparatus (e.g., laparoscopic device 331E) are preferably used as follows.

First, hollow needle 305E is passed to the occlusion site, preferably while needle 305E is contained within sheath 333E of laparoscopic device 331E (FIG. 107). Then sheath 333E is retracted, e.g., by turning knob 334E (FIG. 108), and hollow needle 305E is passed across the blood vessel (e.g., a vein) which is to be occluded (or passed across another tubular structure which is to be occluded, or passed through tissue or objects to be secured to one another, such as a solid organ, or layers of tissue, etc.).

Next, hollow needle 305E is retracted proximally, back across the blood vessel, e.g., via first trigger 336E (FIG. 109). This action allows legs 235E of distal implant 205E to expand radially on the far side of the blood vessel. At this point, distal implant locking tube 220E extends proximally through the blood vessel.

Then, with distal implant delivery tube 310E held in place via distal implant delivery tube 310E and its interlock with distal implant locking tube 220E (and hence distal implant 205), hollow needle 305E is withdrawn further proximally (e.g., via first trigger 336E) until proximal implant 210E is no longer constrained within hollow needle 305E (FIG. 110). As this occurs, legs 295E of proximal implant 210E are released from the constraint of hollow needle 305E and open radially.

Proximal implant delivery tube 330E is then advanced distally, e.g., using second trigger 337E, until proximal implant 210E and distal implant 205E come together (FIG. 111). As distal implant 205E and proximal implant 210E move together, their legs 235E, 295E compress the blood vessel therebetween, thereby occluding the blood vessel. Distal implant 205E and proximal implant 210E continue moving together until inwardly-projecting tangs 300E of proximal implant 210E enter circumferential grooves or recesses 245E of distal implant 205E, thereby locking the two members into position relative to one another.

At this point, proximal implant delivery tube 330E is withdrawn (FIG. 112), distal implant delivery tube 310E is released from distal implant 205E (i.e., by using lever 338E to unlock the second half 361E of the mechanical interlock (carried by the distal end of distal implant delivery tube 310E) from the first half 266E of the mechanical interlock (carried by the proximal end of distal implant locking tube 220E), and then the installation device is withdrawn (FIG. 113).

The foregoing procedure leaves two-part occluder 200E locked in position across the blood vessel, with the opposing legs 235E, 295E compressing the blood vessel therebetween, whereby to occlude the blood vessel.

In the preceding disclosure, two-part occluder 200E is discussed in the context of using the elasticity of its legs 235E, 295E to cause its legs 235E, 295E to reconfigure from a diametrically-reduced configuration (e.g., when constrained within a delivery needle) to a diametrically-expanded configuration (e.g., when released from the constraint of a delivery needle). However, it should also be appreciated that where legs 235E, 295E are formed out of a shape memory material (e.g., Nitinol), a temperature change may be used to reconfigure legs 235E, 295E from a diametrically-reduced configuration to a diametrically-expanded configuration. By way of example but not limitation, in this form of the invention, legs 235E, 295E may be constructed so as to have a diametrically-reduced configuration when maintained at a temperature below body temperature, and legs 235E, 295E may be constructed so as to have a diametrically-expanded configuration when maintained at body temperature. As a result, by cooling two-part occluder 200E to a temperature below body temperature, inserting the two-part occluder into the body, and then allowing the two-part occluder to heat to body temperature, legs 235E, 295E can be caused to reconfigure from their diametrically-reduced configuration to a diametrically-expanded configuration.

FIGS. 114-120 show an alternative form of installation device. More particularly, FIGS. 114-120 show another laparoscopic device 331E. The laparoscopic device 331E shown in FIGS. 114-120 is generally similar to the laparoscopic device 331E shown in FIGS. 105-113, except that second trigger 337E is omitted, and lever 338E is used to both: (i) advance proximal implant delivery tube 330E until proximal implant 210E and distal implant 205E come together (FIG. 119), and (ii) release distal implant 205E from distal implant locking tube 220E (FIG. 120) (i.e., by unlocking the second half 361E of the mechanical interlock (carried by the distal end of distal implant delivery tube 310E) from the first half 266E of the mechanical interlock (carried by the proximal end of distal implant locking tube 220E)).

Figure 121:
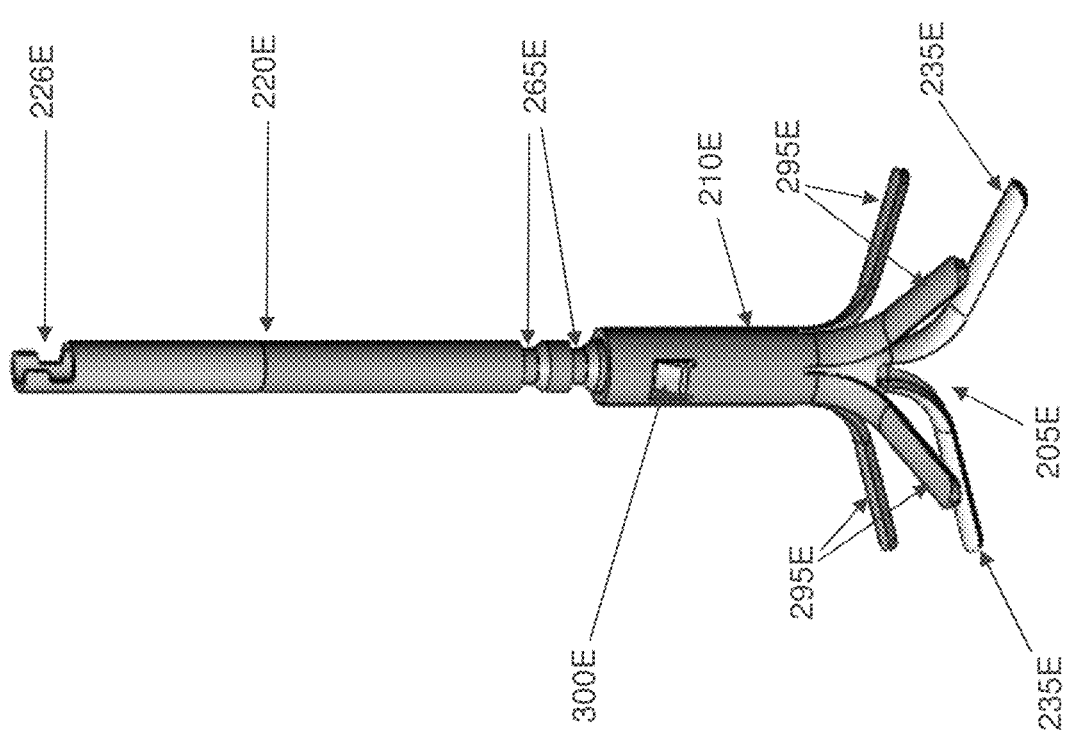
FIGS. 121-123 are schematic views showing another two-part occluder formed in accordance with the present invention.
Figure 123:
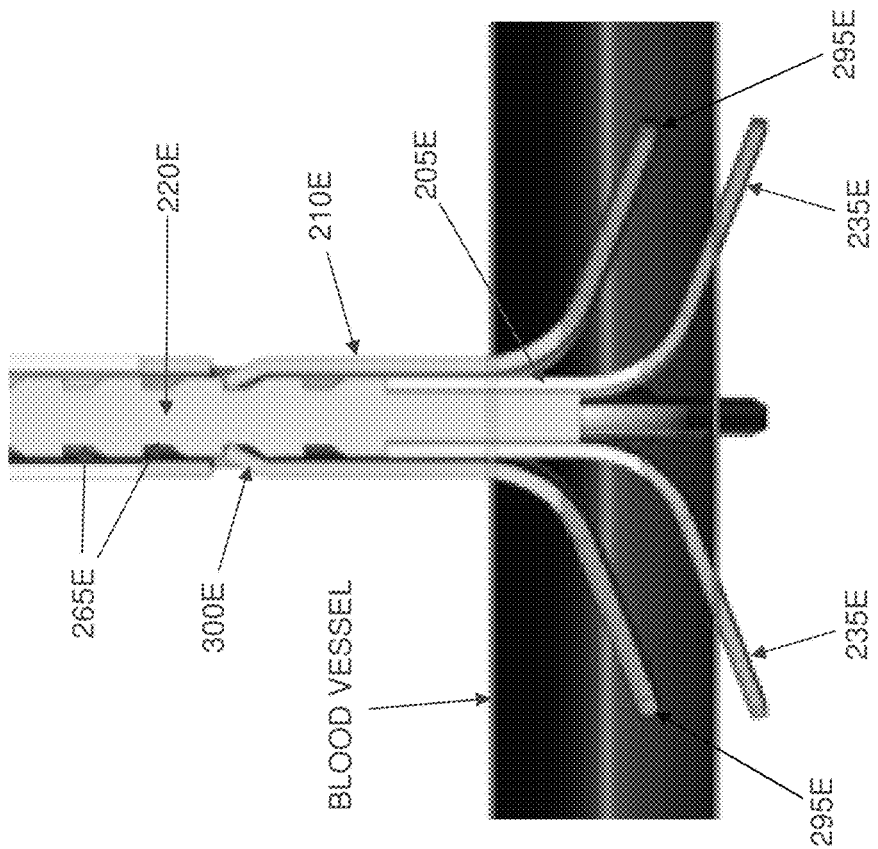
Figure 122:
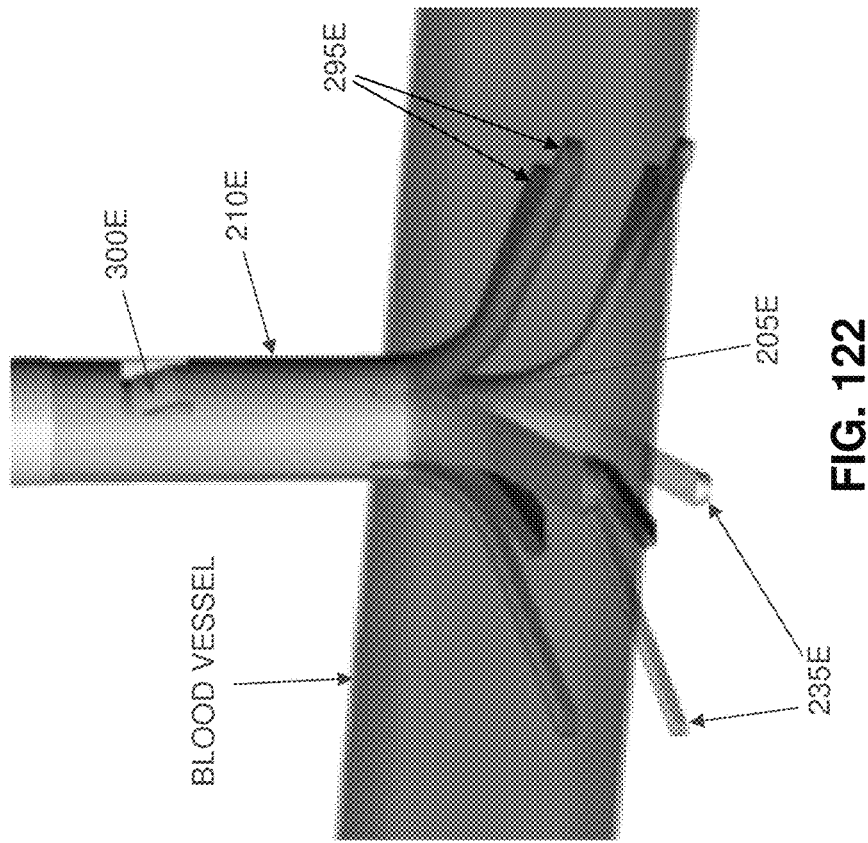
Figure 127:
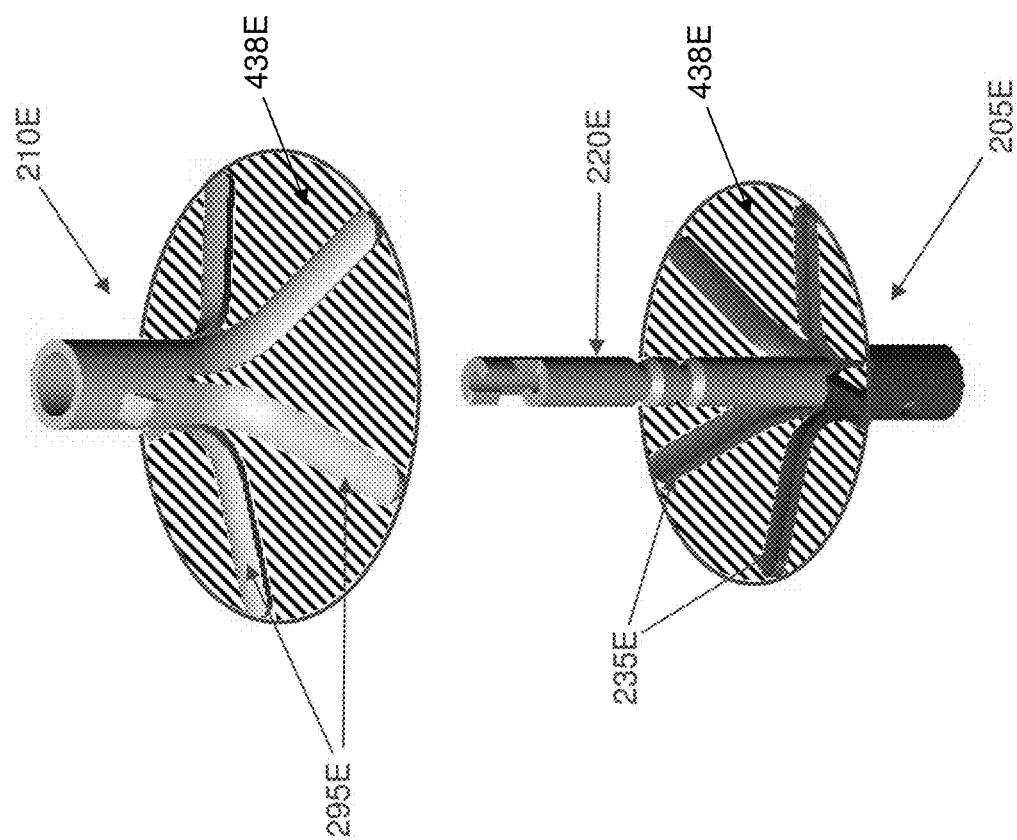
FIG. 127 is a schematic view showing another two-part occluder formed in accordance with the present invention.
Figure 128:
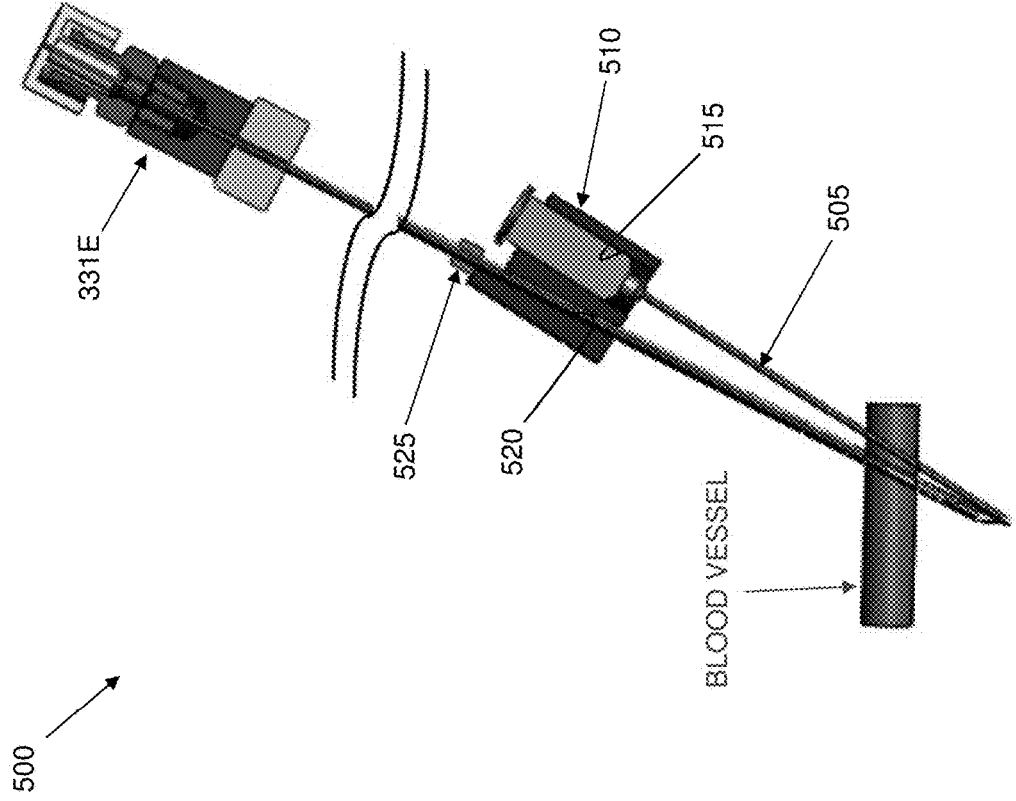
FIGS. 128-133 are schematic views showing a placement device for facilitating proper placement of an occluder so as to occlude a blood vessel (or other hollow tubular body)
Figure 129:
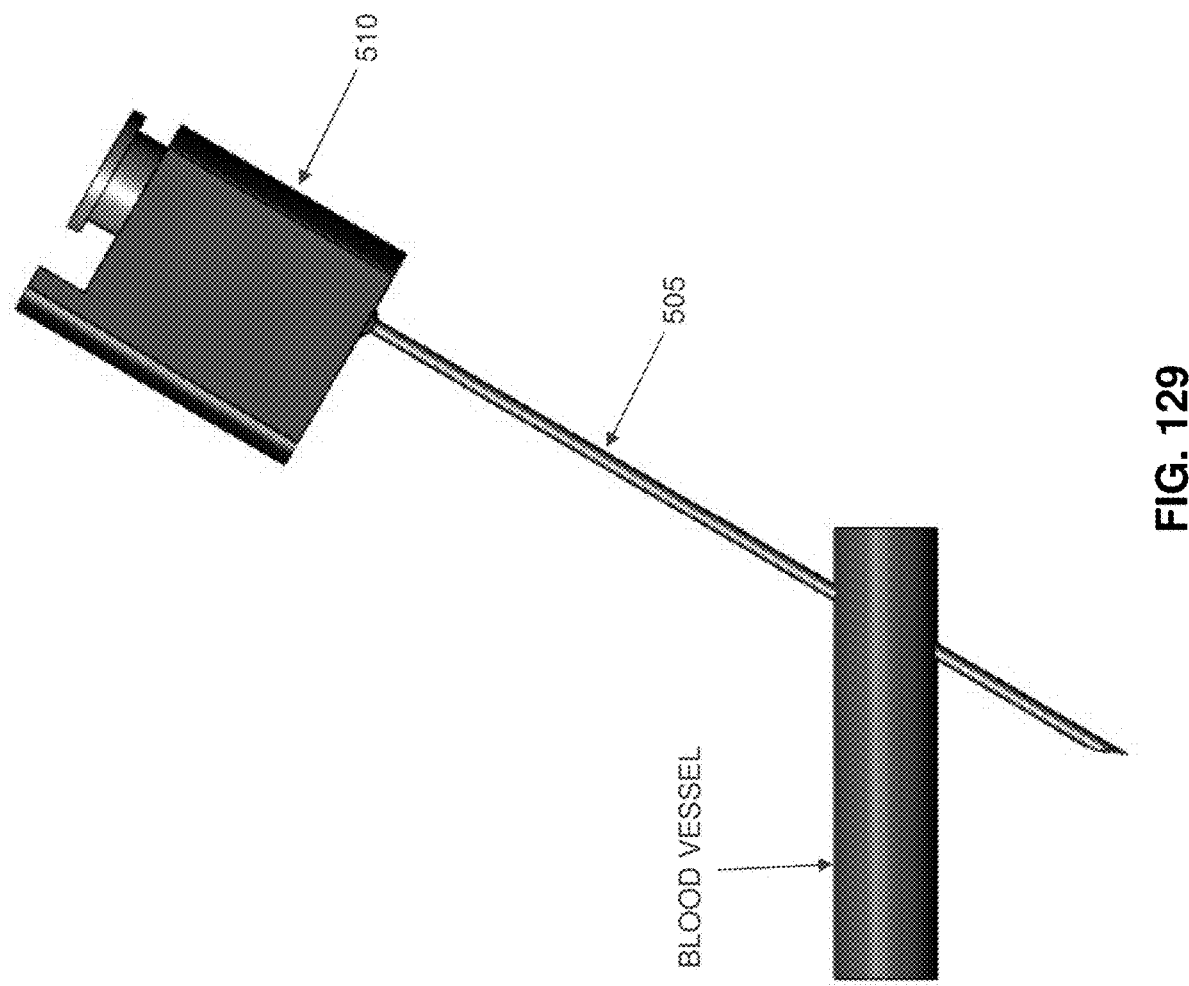
Figure 131:
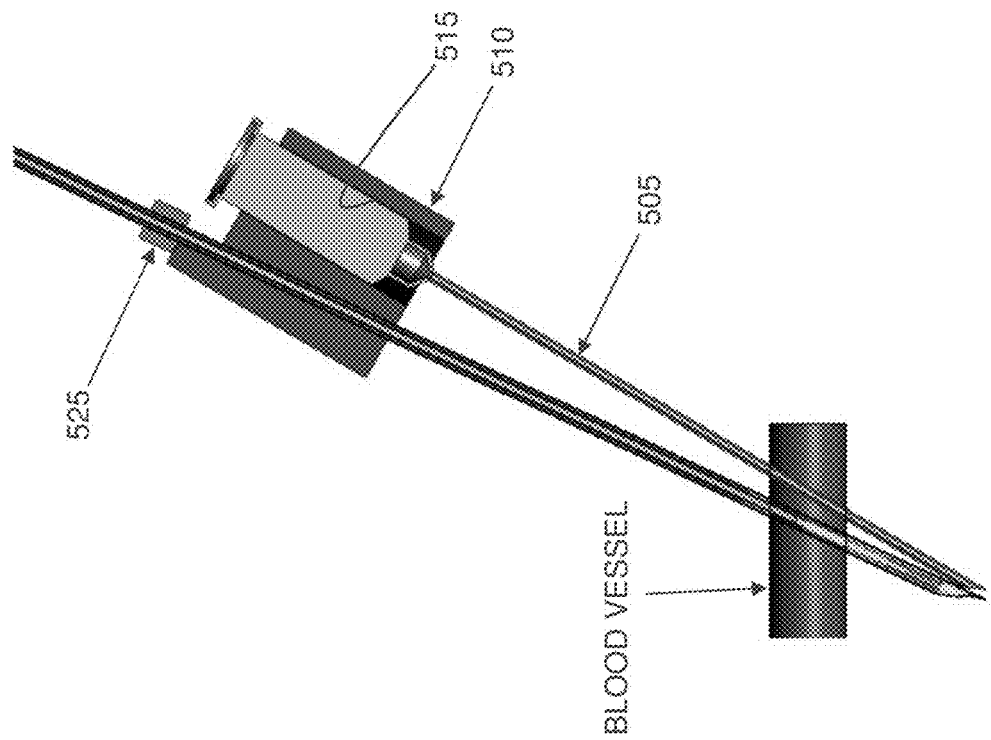
Figure 130:
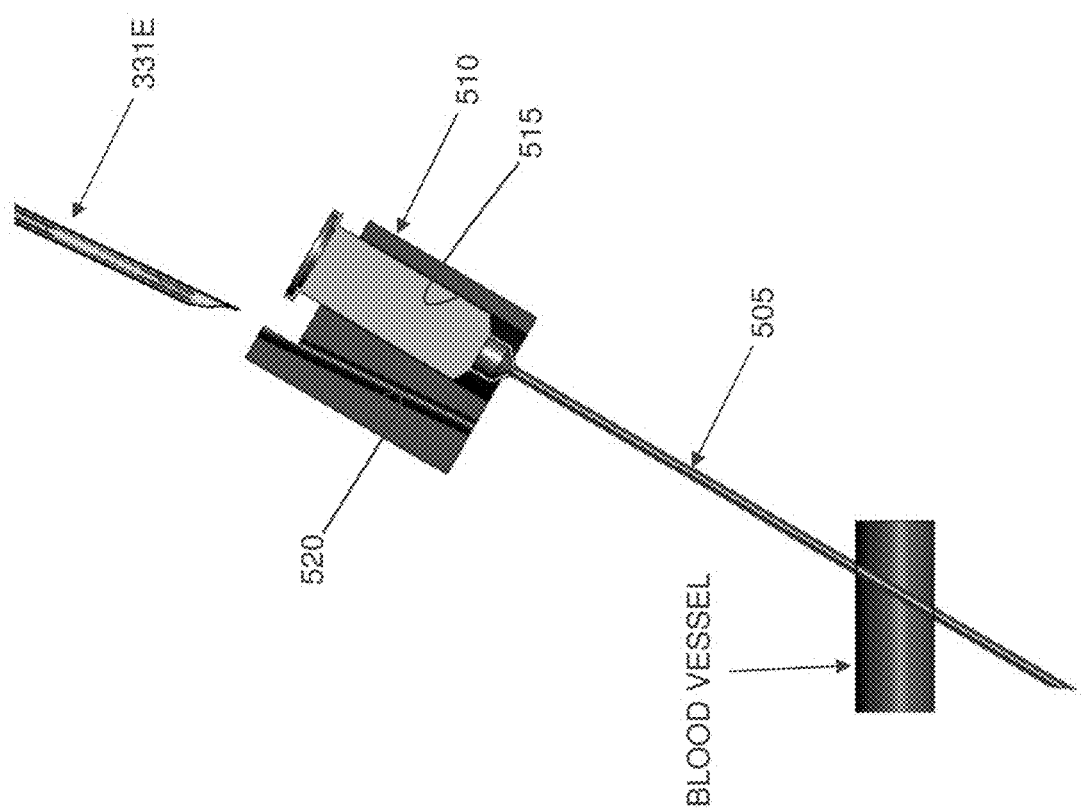
Figure 132:
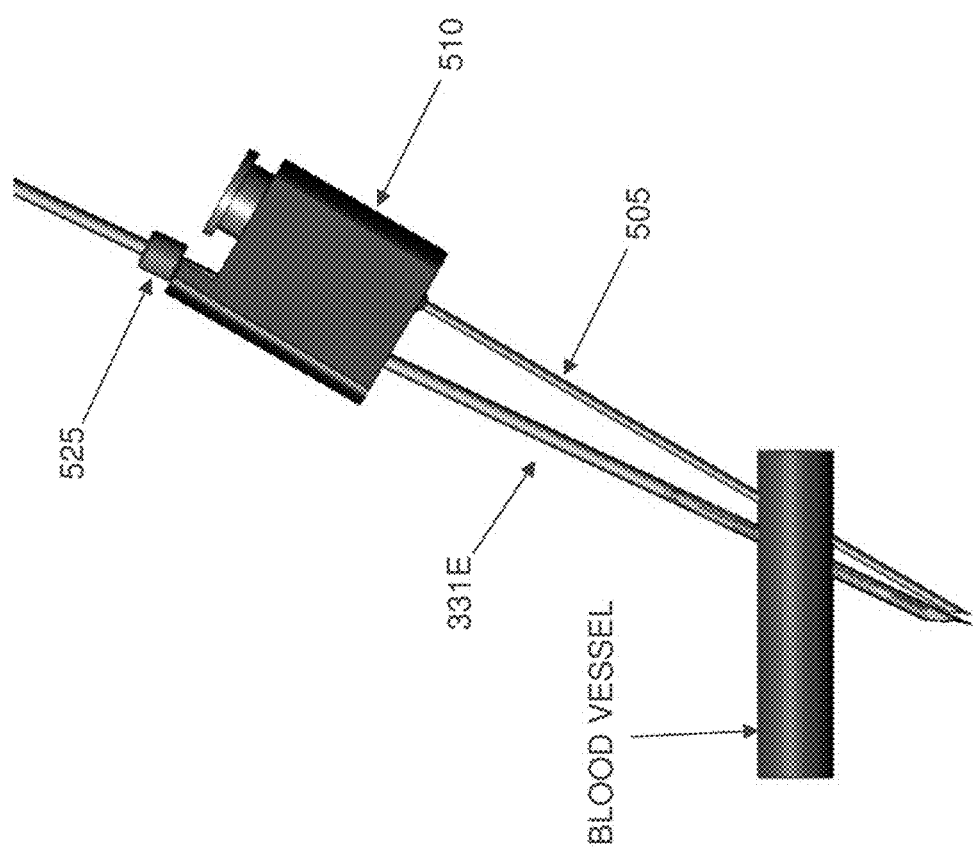
Figure 133:
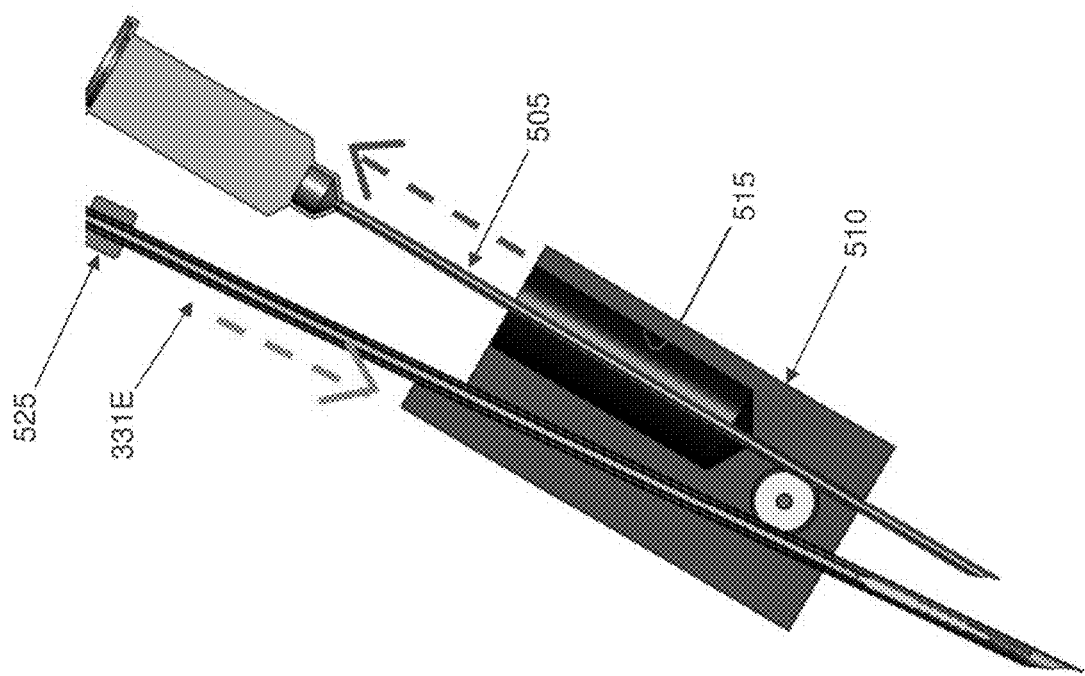
Figure 134:
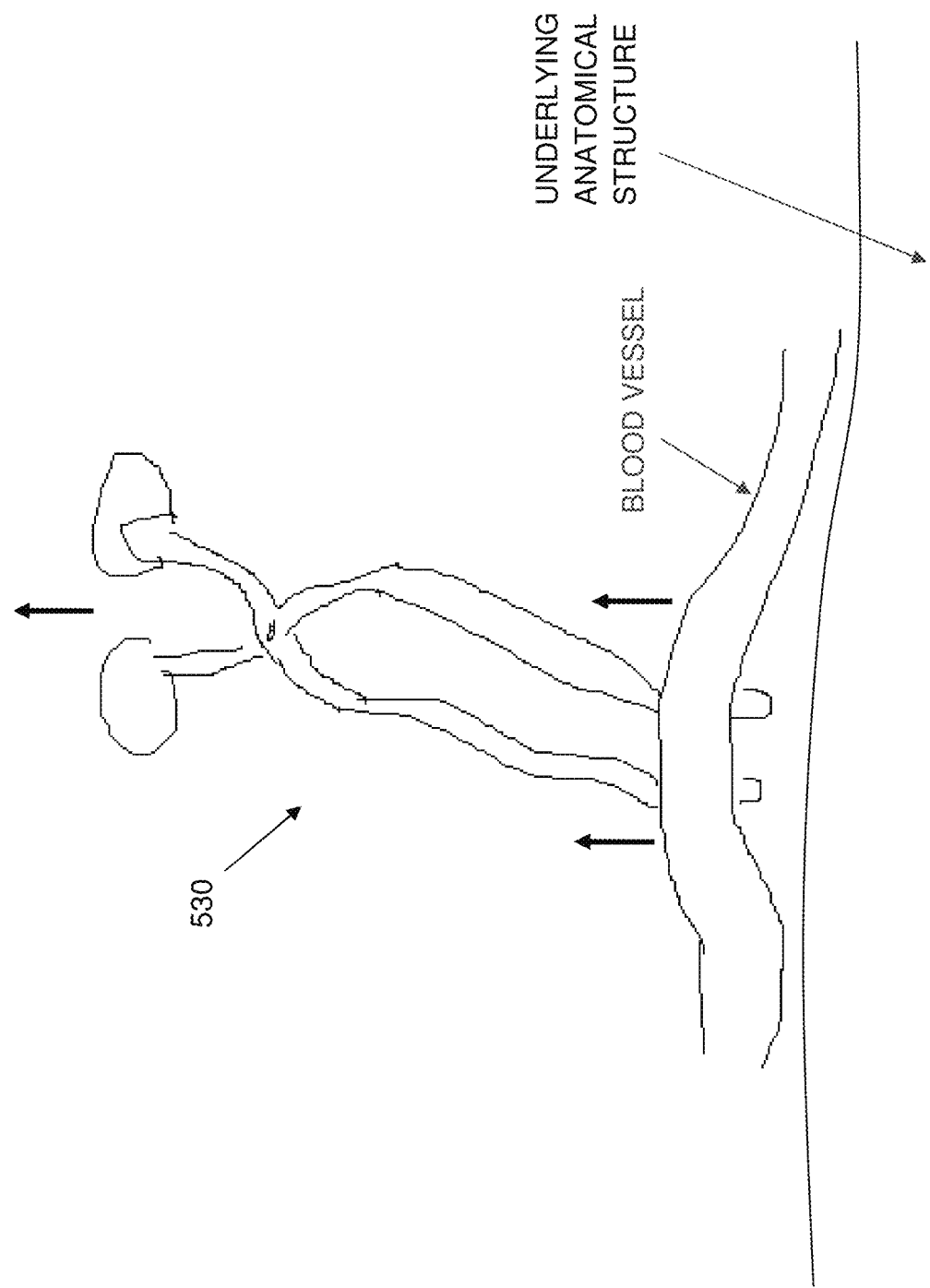
FIG. 134 is a schematic view showing a tool for lifting a blood vessel (or other hollow tubular body) away from an underlying anatomical structure so as to facilitate proper placement of an occluder.

FIGS. 121-123 show another two-part occluder 200E also formed in accordance with the present invention. The occluder 200E shown in FIGS. 121-123 is substantially the same as the occluder 200E shown in FIGS. 101-120, except that legs 235E of distal implant 205E, and legs 295E of proximal implant 210E, have their concavity directed in the same direction, so that legs 235E, 295E nest with one another rather than confront one another. In addition, as seen in FIGS. 121-123, tube 225E of distal implant 205E is partially received in lumen 290E of proximal implant 210E.

FIGS. 124-126 show one preferred construction for releasably securing distal implant 205E of the two-part occluder 200E of FIGS. 121-123 to distal implant delivery tube 310E. More particularly, in this form of the invention, and looking now at FIGS. 124-126, the first half 266E of the mechanical interlock (carried by the proximal end of distal implant locking tube 220E) comprises a stepped configuration 433E, and the second half 361E of the mechanical interlock (carried by the distal end of distal implant delivery tube 360E) comprises another stepped configuration 434E, wherein stepped configuration 433E and stepped configuration 434E are inverses of one another so as to mate together. After the second half 361E of the mechanical interlock (carried by the distal end of distal implant delivery tube 310E) has been secured to the first half 266E of the mechanical interlock (carried by the proximal end of distal implant locking tube 220E), the connection between distal implant delivery tube 310E and distal implant 205E can be enhanced, e.g., by telescopically projecting a locking rod 436E out of a central lumen 437E of distal implant delivery tube 310E and into lumen 262E of implant locking tube 220E. In this form of the invention, the installation device (e.g., laparoscopic device 331E of FIGS. 105-113, or laparoscopic device 331E of FIGS. 114-120) include appropriate control means (e.g., release lever 338E) for telescopically moving locking rod 436E out of central lumen 437E of distal implant delivery tube 310E and into lumen 262E of implant locking tube 220E. Alternatively, in another form of the invention, internal locking rod 436E may be replaced by an overtube (not shown) which telescopically projects over distal implant delivery tube 310E and distal implant locking tube 220E of distal implant 205E, whereby to enhance the connection between the members.

It should also be appreciated that other forms of mechanical interlocks may be used for releasably securing distal implant 205E of the two-part occluder 200E of FIGS. 121-123 to distal implant delivery tube 310E. By way of example but not limitation, a screw interlock may be used, e.g., the first half 266E of the mechanical interlock (carried by the proximal end of distal implant locking tube 220E) may comprise a threaded bore, and the second half 361E of the mechanical interlock (carried by the distal end of distal implant delivery tube 360E) may comprise a threaded post, wherein the threaded post carried by the distal end of distal implant delivery tube 360E may be received in the threaded bore of distal implant locking tube 220E. Alternatively, other configurations of a screw interlock may be used, or other forms of mechanical interlocks may be used.

In the constructions shown in FIGS. 101-143, a mechanical interlock (e.g., a first half 266E carried by the proximal end of distal implant locking tube 220E and a second half 361E carried by the distal end of distal implant delivery tube 310E) is used to connect distal implant locking tube 220E (and hence distal implant 205E) to distal implant delivery tube 310E. Alternatively, if desired, distal implant locking tube 220E can be formed integral with distal implant delivery tube 310E, with a weakened section disposed at their intersection, and the two members separated by a mechanical breaking action.

It will be appreciated that, in certain circumstances, it may be desirable to increase the surface area of those portions of the occluder which contact the tubular structure, in order to better distribute the load applied to the tissue. In this situation, it can be helpful to increase the width of the legs (e.g., legs 235E and/or legs 295E of two-part occluder 205E, etc.), and/or to provide flexible material in the zone between adjacent legs (e.g., in the manner of an umbrella) so that the flexible material can also carry load (i.e., essentially increasing the effective width of legs 235E and/or legs 295E). See, for example, FIG. 127, which shows flexible material 438E extending between legs 235E and legs 295E.

FIGS. 128-133 show a placement device 500 for the facilitating proper placement of the occluder (e.g., the two-part occluder 200E) so as to occlude a blood vessel (or other hollow tubular body). Placement device 500 generally comprises a blood vessel locator needle 505, which is a needle of relatively small diameter (e.g., 21 gauge or smaller), and a guiding component 510 (which may be manufactured from an inexpensive material such as plastic). Guiding component 510 includes a seat 515 for receiving blood vessel locator needle 505, and an opening 520 for slidably accommodating the shaft of an installation device for setting the occluder (e.g., laparoscopic device 331E of FIGS. 105-113, or laparoscopic device 331E of FIGS. 114-120, etc.).

In use, blood vessel locator needle 505 is positioned in seat 515 of guiding component 510, and then the blood vessel locator needle 505 is advanced through the target blood vessel (e.g., under ultrasound guidance). See FIG. 129. Proper placement of blood vessel locator needle 505 is confirmed as blood begins to flow out the proximal end of blood vessel locator needle 505. Next, the shaft of the installation device for setting the occluder (e.g., laparoscopic device 331E of FIGS. 105-113, or laparoscopic device 331E of FIGS. 114-120, etc.) is advanced through opening 520 of guiding component 510. See FIG. 130. Advancement occurs until a stop 525 on the shaft of the installation device engages the proximal end of guiding component 510. See FIG. 131. When stop 525 on the shaft of the installation device engages the proximal end of guiding component 510, the distal end of the shaft of the installation device will have passed through the target blood vessel. See FIG. 132. At this point, blood vessel locator needle 505 is withdrawn (see FIG. 133) and deployment of the occluder proceeds as previously discussed.

It will be appreciated that, in certain circumstances, the blood vessel (or other tubular structure) to be occluded may be positioned close to an underlying anatomical structure, e.g., an organ, a nerve, another tubular structure, etc. In this situation, it may be helpful to lift the blood vessel (or other tubular structure) upward, away from the underlying anatomical structure, so that the sharp distal tip of the deployment needle does not engage the underlying anatomical structure, and so that the distal end of the occluder (e.g., distal implant 205E of two-part occluder 200E) does not engage the underlying anatomical structure, since any such engagement with the underlying anatomical structure could cause trauma to the underlying anatomical structure. To that end, and looking now at FIG. 134, clamping forceps 530 (or other tool having a bifurcated distal end) may be placed between the blood vessel (or other tubular structure) and the underlying anatomical structure, and then pulled upwardly, away from the underlying anatomical structure, so as to separate the target blood vessel (or other tubular structure or tissue) from the underlying anatomical structure. The occluder (e.g., two-part occluder 200E) may then be safely passed through the target blood vessel (or other tubular structure), passing between the bifurcated distal end of the tool, and deployed as previously discussed.

Using the Occluder to Occlude Tubular Structures Other than Blood Vessels

It will be appreciated that the occluder of the present invention can also be used to occlude tubular structures other than blood vessels. By way of example but not limitation, the temporary occluder of the present invention can be used to occlude other structures within the body (e.g., tubes such as fallopian tubes and/or vas deferens for temporary or permanent sterilization, ducts such as bile ducts and cystic ducts for cholecystectomy, lymphatic vessels, including the thoracic duct, fistula tracts, etc.).

Using the Occluder to Close Openings in Structures and/or for Securing at Least Two Objects Together In the foregoing disclosure, the occluder is discussed in the context of occluding a tubular structure (e.g., a blood vessel, fallopian tubes, lymphatic vessels, etc.) by clamping together opposing side walls of the tubular structure in order to occlude the tubular structure. In such an application, the occluder effectively secures one side wall of the tubular structure to the opposing side wall of the tubular structure. However, it should also be appreciated that the occluder of the present invention may be used to close openings in structures and/or to secure two or more objects together for other applications.

By way of example but not limitation, the occluder of the present invention may be used to secure two or more portions of tissue together so as to close an incision.

By way of further example but not limitation, the occluder of the present invention may be used in a "stomach stapling" procedure to bring together opposing side walls of the stomach in order to reduce the size of the stomach.

Furthermore, the occluder of the present invention may be used in an organ resection (e.g., a liver resection), so as to seal the periphery of the resected organ.

Figure 135:
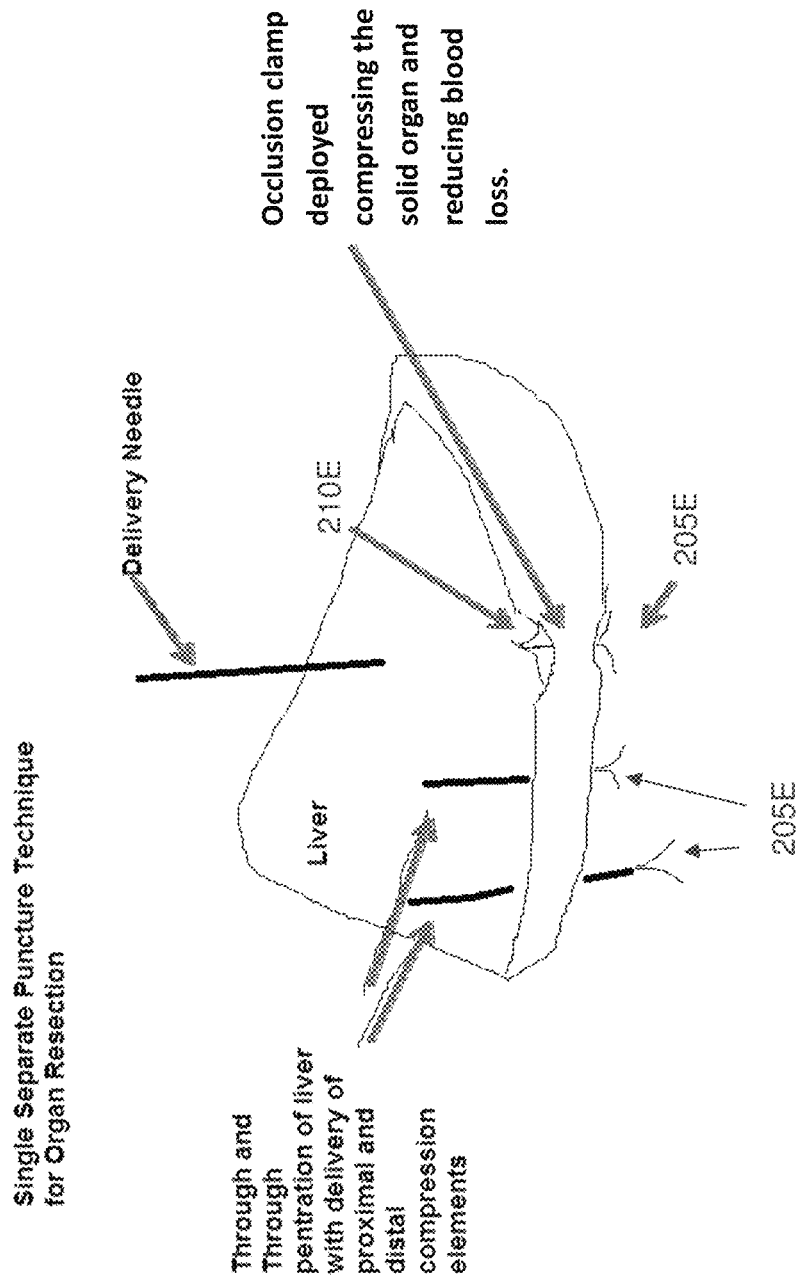
FIGS. 135-137 are schematic views showing use of an occluder for closing off an organ.
Figure 136:
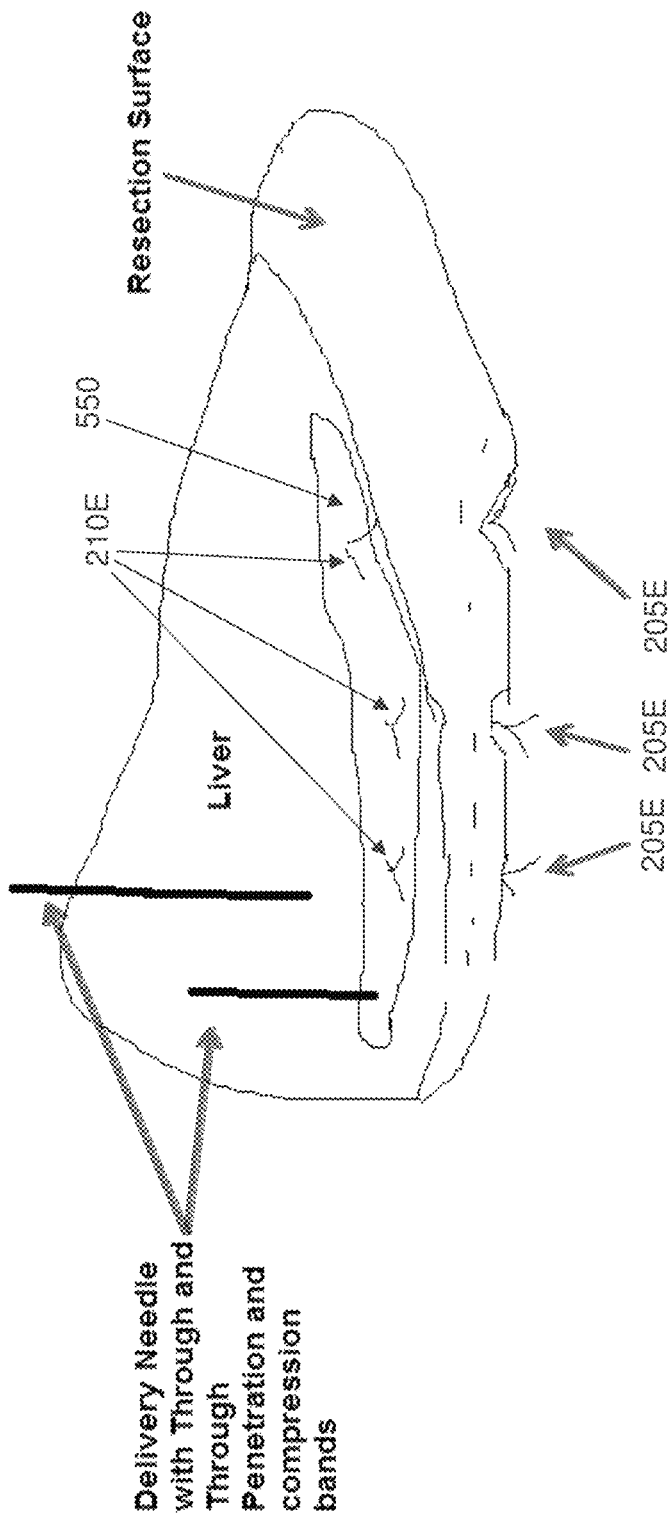
Figure 137:
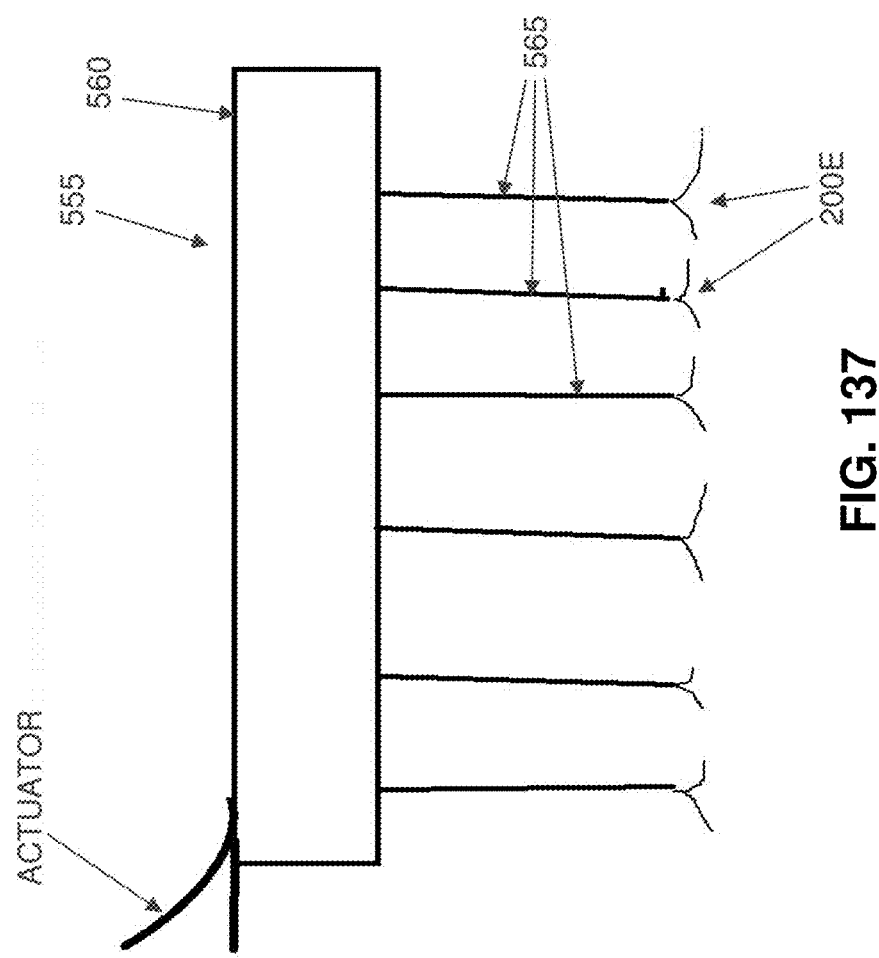

By way of further example but not limitation, and looking now at FIGS. 135-137, the occluder of the present invention can be used for selectively clamping or occluding regions of solid organs so as to selectively stop blood flow or blood loss in various regions through tissue compression. The occluder may be used in solid organ resection of the kidney or liver or other organs. Blood loss and secretion leakage (e.g., bile, urine, etc.) can be problematic in existing solid organ resection procedures. Average blood loss for a liver resection is 700-1200 ml. By clamping desired regions of the solid organ with the occluder of the present invention, it is possible to significantly reduce the amount of undesirable fluid loss (blood loss, secretion leakage, etc.). The occluder of the present invention, can be used to apply pressure selectively to broad areas of the organ and, additionally, may also be used to close off selective tubular structures and vessels connecting the organ with other regions of the body. In one embodiment and method, multiple discrete occluder elements may be individually, selectively deployed across regions of the organ. See, for example, FIG. 135, which shows multiple, single, separate puncture placements of the occluder for closing off a resected liver. Note that where multiple, single, separate puncture placements of the occluder are used, different regions of the solid organ may be compressed to different and controllable degrees.

In a novel embodiment of the present invention, the length of distal implant locking tube 220E (of distal implant 205E) remaining in the body can be determined once clamping of the occluder has been effected, by providing distal implant locking tube 220E and/or distal implant delivery tube 310E with weakened (e.g., frangible) sections, and by breaking off distal implant locking tube 220E from distal implant delivery tube 310E at a region above proximal implant 210E. This break can be achieved by incorporating selective weakened regions into the distal implant locking tube 220E and/or distal implant delivery tube 310E, so that when a selective weakened region is subjected to twists, or torques, or bending, or pulling, or selective other strains or stresses or the like, distal implant locking tube 220E will separate from distal implant delivery tube 310E at a location proximal to proximal implant 210E. Because clamping is effected across the tissue, distal implant locking tube 220E connecting distal implant body 215 and proximal implant 210E will not move, while distal implant delivery tube 310E will disconnect from distal implant locking tube 220E. Distal implant locking tube 220E, which connects distal implant body 215E and proximal implant 210E, may be solid or flexible.

In other embodiments of the present invention, distal implant locking tube 220E may be composed of multiple interlocking sections, and constrained by an encasing sheath, or once deployed, by the surrounding tissue. Once clamping of the tissue is achieved, the sheath can be retracted beyond the proximal implant, exposing an interlocking region between the distal implant locking tube 220E sections and then, with a twist, or appropriate unlocking mechanism, enable the occluder to be disconnected from the distal implant delivery tube 310E.

This construction enables the clamping distance between distal implant 205E and proximal implant 210E to be controllable, and allows for significant tissue thicknesses to be clamped.

In the embodiment shown in FIG. 136, the occluders are delivered in conjunction with single or multiple compression bands 550, which may be polymers, or other tissue material or metals or other commonly used materials known in the art. The compression bands 550 may be rolled into the delivery needle or sheath and unfurled prior to delivery of the occluders. The compression bands 550 extend the pressure across a broader region of the organ or tissue which receives the occluders of the present invention.

In other embodiments, the legs of the occluder may have a thin metallic or polymeric mesh or film that is flexible, yet connects between the fingers, to enable further distribution of pressure on a clamped tissue, vessel, organ or the like.

In the embodiment of FIG. 137, multiple occluders can be delivered in parallel to an organ, tissue, tubular structure or the like. In this form of the invention, an installation device 555, comprising a body 560 having a plurality of deployment needles 565 extending therefrom, can be used for setting the multiple occluders. Installation device 555 can deliver either single occluders deployed one at a time, but in a spatially-constrained way, with a pre-defined spacing between the occluders (determined by the predefined spacing between deployment needles 565), or can deliver a plurality of occluders all at the same time, with a single activation control. This construction can reduce the amount of time required for a procedure such as a resection, by providing for simultaneous occluder deployments.

In other embodiments of the present invention, the occluders can be deployed across multiple tissues, or multiple folds of the same tissue, organ or tubular structure. In certain embodiments of the present invention, the distal implant locking tube 220E may be elastic, allowing for some movement of the clamped tissue, while still maintaining a desired clamping force or pressure on the tissue.

The occluders of the above invention may also be used for bariatric surgery, or to reduce or plicate the stomach, or to create a gastrostomy sleeve.

In another embodiment of the present invention, the unreleased distal implant 205E can be used as the retractor, and retract the tissue away from any organs or tissues or major blood vessel beneath, enabling subsequent deployment of other occluders to be placed in a manner that may enable reduction of the size of an organ, joining organs together, closing a tear in the bowel or the like. Once the other desired occluders have been deployed, the deployment of the first occluder (i.e., unification of the proximal implant 210E with the distal occluder 205E) can be completed.

Use of the Invention Under Direct Visualization and/or Indirect Visualization

Significantly, the present invention may be practiced under direct visualization (e.g., during "open" surgery) or under indirect visualization (e.g., during laparoscopic surgery where visualization is provided through the use of a scope, or during percutaneous surgery where visualization is provided through the use of imaging apparatus such as an ultrasound imager, an X-ray imager, etc.).

Modifications of the Preferred Embodiments

It should be understood that many additional changes in the details, materials (e.g., shape memory polymers that are permanent or that dissolve over time, or carbon nanotube based), steps and arrangements of parts, which have been herein described and illustrated in order to explain the nature of the present invention, may be made by those skilled in the art while still remaining within the principles and scope of the invention.

The invention claimed is:

1. An apparatus for securing a tissue layer to another tissue or non-tissue layer comprising:
   a distal implant comprising a distal body and a plurality of legs extending from the distal body and which may assume (i) a diametrically-reduced delivery configuration in which it can be passed through the layers and (ii) a diametrically-expanded deployed configuration in which the legs are extended radially of the distal body; and
   a proximal implant, separate from the distal implant, the proximal implant comprising a proximal body and a plurality of legs extending from the body, the legs being configured to assume (i) a diametrically-reduced delivery configuration and (ii) a diametrically-expanded deployed configuration in which the legs are extended radially of the proximal body;
   the implants being connectible to each other, wherein the radially extended configuration of the legs are constructed and arranged so that when the implants are connected together, legs of the proximal and distal implants are interdigitated in the absence of tissue between the implants.

2. The apparatus of claim 1 wherein the proximal and distal implants are deployable separately and independently of each other.

3. The apparatus of claim 1, wherein the apparatus comprises a super-elastic material such as nitinol and where the legs of each of the implants self-expand upon release of each implant from its delivery configuration.

4. The apparatus of claim 1, wherein the distal implant legs together form a concave configuration when diametrically expanded, and the proximal implant legs together form a concave configuration when diametrically expanded.

5. The apparatus of claim 4 wherein the implants are arranged so that their concavities face towards each other.

6. The apparatus of claim 1, wherein the layers comprise the opposed walls of a mammalian body lumen.

7. The apparatus of claim 6, wherein when secured together, at least one of the proximal body and the distal body transfixes the layers at a transfixion site.

8. The apparatus of claim 7, wherein the plurality of legs of the distal implant and the plurality of legs of the proximal implant together create an area of compression that circumscribes the transfixion site.

9. The apparatus of claim 1, further comprising a delivery tube comprising a needle or a catheter having a distal outlet opening, wherein the delivery tube contains the distal implant in its diametrically-reduced configuration and the proximal implant in its diametrically-reduced configuration in readiness to be ejected serially from the delivery tube.

10. The apparatus of claim 9, wherein the delivery tube is configured to advance the distal implant in its diametrically-reduced configuration through at least two layers before the distal implant is ejected from the tube.

11. The apparatus of claim 10, further comprising a mechanism for maintaining the position of the distal implant after ejection out of the delivery tube, thereby to enable the delivery tube to be withdrawn proximally to deploy the proximal implant.

12. The apparatus of claim 11 further comprising a push rod engageable with the proximal end of the proximal implant to maintain the position of the proximal implant proximally of the tissue layers while the delivery tube is withdrawn to deploy the proximal implant and wherein the mechanism for maintaining the position of the distal implant comprises a retention member configured to selectively engage with the distal implant to hold the distal implant whereby the retention member and the push rod can be manipulated to draw the deployed proximal and distal implants toward each other to connect them together.

13. The apparatus of claim 11 wherein the mechanism for maintaining the position of the distal implant comprises the proximal end of the distal implant having a first portion of an interlock mechanism;
a distal implant retention shaft having proximal and distal ends with a second portion of the interlock mechanism at the distal end, the first and second portions of the interlock mechanism being mateable to releasably connect with each other, the proximal end of the distal implant retention shaft being receivable through and extending proximally of the body of the proximal implant, the interlock mechanism enabling the position of the distal implant to be maintained while the delivery tube is withdrawn proximally.

14. The apparatus of claim 13 where the first and second portions of the interlock mechanism are complementary and separable from each other.

15. The apparatus of claim 14 further comprising a supplemental lock for the interlock mechanism to temporarily prevent separation of the portions of the interlock mechanism.

16. The apparatus of claim 15 wherein the distal implant delivery shaft and the retention shaft are tubular, each having a lumen, and wherein the supplemental lock comprises an elongate wire removably disposed in the lumen of the distal implant delivery shaft and passing through the interlock mechanism to engage the interlock mechanism and prevent separation of the portions of the interlock mechanism.

17. The apparatus of claim 11, wherein the mechanism comprises a retention member configured to selectively engage with the distal implant to hold the distal implant in place when deployed.

18. The apparatus of claim 17, wherein the retention member is configured to fit axially through a lumen in the distal body, and further comprises a selectively expandable locking region configured to interfere with the lumen of the distal body lumen to maintain the position of the distal implant, the locking region being selectively configurable to a low profile to release the distal implant and enable removal of the retention member through the hymen of the distal body.

19. The apparatus of claim 17 further comprising a push rod engageable with the proximal end of the proximal implant to maintain the position of the proximal implant proximally of the tissue layers while the delivery tube is withdrawn to deploy the proximal implant.

20. The apparatus of claim 1 further comprising:
the proximal implant comprising a proximal tube having proximal and distal ends, the distal end of the proximal tube having a plurality of longitudinally extending slits extending through the distal end of the proximal tube and defining a plurality of distally extending legs having free distal ends, the proximal tube being formed from a material having a shape memory in which the legs extend radially outward about the proximal tube axis, the legs being confinable into a tubular shape within a delivery tube in readiness to self-expand when released from the delivery tube, the proximal portion of the proximal tube having a locking element.

21. The apparatus of claim 20 further comprising:
the distal implant comprising a distal tube having proximal and distal ends, the proximal end of the distal tube having a plurality of longitudinally extending slits extending through the proximal end of the distal tube and defining a plurality of proximally extending legs having free proximal ends, the distal tube being formed from a material having a shape memory in which the legs extend radially outward about the distal tube axis, the legs being confinable into a tubular shape within a delivery tube in readiness to self-expand when released, the distal body having a proximal portion having a locking element engageable with the locking element of the proximal implant to lock the proximal and distal implants together.

22. The apparatus of claim 1 wherein the legs have free ends and, when deployed, the legs can engage the layers substantially along the length of the legs.

23. The apparatus of claim 1 wherein the bodies of the implants are telescopically connectible and are secured to each other by locking elements disposed on the implant bodies and are independent of the legs.

24. The apparatus of claim 1 wherein the proximal implant is deployable only after the distal implant has been deployed.

25. The apparatus of claim 1 wherein the distal implant can be deployed externally on the distal side of the layers and the proximal implant can be deployed externally on the proximal side of the layers.

26. The apparatus of claim 1 wherein the bodies of the implants are less than about 18 gauge.

27. The apparatus of claim 1 wherein the bodies of the proximal and distal implants are telescopically connectable and are secured by a friction fit.

* * * * *